US010570200B2

(12) United States Patent
Hay et al.

(10) Patent No.: US 10,570,200 B2
(45) Date of Patent: Feb. 25, 2020

(54) ANTIBODY-MEDIATED IMMUNOCONTRACEPTION

(71) Applicant: CALIFORNIA INSTITUTE OF TECHNOLOGY, Pasadena, CA (US)

(72) Inventors: Bruce A. Hay, Pasadena, CA (US); Juan Li, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 361 days.

(21) Appl. No.: 14/170,118

(22) Filed: Jan. 31, 2014

(65) Prior Publication Data

US 2014/0223591 A1      Aug. 7, 2014

Related U.S. Application Data

(60) Provisional application No. 61/759,788, filed on Feb. 1, 2013.

(51) Int. Cl.
C07K 16/26         (2006.01)

(52) U.S. Cl.
CPC .................. *C07K 16/26* (2013.01)

(58) Field of Classification Search
CPC ............... C12N 2800/90; C12N 15/85; C12N 2800/107; C12N 2830/008; C12N 2501/39; C12N 2501/392
See application file for complete search history.

(56) References Cited

U.S. PATENT DOCUMENTS

| 4,676,981 | A | † | 6/1987 | Silversides |
|---|---|---|---|---|
| 4,879,112 | A | | 11/1989 | Silversides et al. |
| 4,946,778 | A | | 8/1990 | Ladner et al. |
| 4,980,286 | A | | 12/1990 | Morgan et al. |
| 5,139,941 | A | | 8/1992 | Muzyczka et al. |
| 5,173,414 | A | | 12/1992 | Lebkowski et al. |
| 5,354,678 | A | | 10/1994 | Lebkowski et al. |
| 5,436,146 | A | | 7/1995 | Shenk et al. |
| 5,474,935 | A | | 12/1995 | Chatterjee |
| 5,478,745 | A | | 12/1995 | Samulski et al. |
| 5,580,859 | A | | 12/1996 | Felgner et al. |
| 5,589,377 | A | | 12/1996 | Lebkowski et al. |
| 5,589,466 | A | | 12/1996 | Felgner et al. |
| 5,593,972 | A | | 1/1997 | Weiner et al. |
| 5,641,870 | A | | 6/1997 | Rinderknecht et al. |
| 5,652,224 | A | | 7/1997 | Wilson et al. |
| 5,801,030 | A | | 9/1998 | McVey et al. |
| 6,013,770 | A | | 1/2000 | Reeves et al. |
| 6,284,733 | B1 | | 9/2001 | Meloen et al. |
| 7,731,939 | B2 | | 6/2010 | Miller et al. |
| 2005/0032171 | A1 | | 2/2005 | Saxena et al. |
| 2010/0186103 | A1* | | 7/2010 | Gao .................. C12N 15/111 800/13 |
| 2010/0233249 | A1* | | 9/2010 | Sutovsky ............. A61K 38/06 424/450 |
| 2011/0113497 | A1 | | 5/2011 | Lee |
| 2012/0266264 | A1 | | 10/2012 | Lee |
| 2014/0283155 | A1 | | 9/2014 | Akbari et al. |
| 2015/0010578 | A1† | | 1/2015 | Balazs |
| 2015/0230430 | A1* | | 8/2015 | Wilson .................. A01K 21/00 514/44 R |
| 2015/0237838 | A1 | | 8/2015 | Hay et al. |
| 2016/0060358 | A1 | | 3/2016 | Hay |
| 2016/0345556 | A1 | | 12/2016 | Hay et al. |
| 2018/0320164 | A1 | | 11/2018 | Hay |

FOREIGN PATENT DOCUMENTS

| JP | 63126482 A * | 5/1988 |
|---|---|---|
| JP | 2544120 B2 | 10/1996 |
| WO | WO 90/11092 | 10/1990 |
| WO | WO 92/06180 | 4/1992 |
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 94/08598 | 4/1994 |
| WO | WO 94/12649 | 6/1994 |
| WO | WO 1999/065520 A1 | 12/1999 |
| WO | WO 2001/007083 A1 | 2/2001 |
| WO | WO 2005/095458 A1 | 10/2005 |
| WO | WO 2008/009960 A2 | 1/2008 |
| WO | WO 2010/049777 A1 | 5/2010 |
| WO | WO 2012/143401 A1 | 10/2012 |
| WO | WO 2014/052693 A2 | 4/2014 |
| WO | WO 2014/120975 A1 | 8/2014 |
| WO | WO 2014/120975 A8 | 8/2014 |
| WO | WO 2018/204722 A1 | 11/2018 |

OTHER PUBLICATIONS

Ohlsson et al., BMC Gastroenterology,10: 48, 2010.*
Poulsen et al., Journal of Immunology, 187:4229-4235, 2011.*
Wakchaure et al., IJETAE 5(11), 210-213, 2015.*
Cao et al., J. of Exp. Zoo., 311A: 368-376, 2009.*
Brevini et al., Theriogenology, 74: 544-550, 2010.*
Paris et al., Theriogenology, 74: 516-524, 2010.*
Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Graham et al., Genome Biology, 16:260, 2014.*
Niemann, Transgenic Research, 7: 73-75 (1998).*
Clark et al. Nature Reviews: 4: 825-833, 2003.*
Eurogentec, "Gonadotrophin-Releasing Hormone (LHRH) (SMI 41) Monoclonal Antibody" from Eurogentec Price List of Covance Antibodies, 2011.*

(Continued)

*Primary Examiner* — Thaian N. Ton

(74) *Attorney, Agent, or Firm* — Knobbe, Martens, Olson & Bear, LLP

(57) ABSTRACT

The present disclosure generally relates to methods and compositions for contraception. In some embodiments, vector based approaches for contraception are provided.

21 Claims, 22 Drawing Sheets

Specification includes a Sequence Listing.

(56) References Cited

OTHER PUBLICATIONS

U.S. Appl. No. 61/707,900, publically available and downloaded from http://www.wipo.int/portal/en/index.html on Sep. 15, 2018.*
A Phase 1, Randomized, Blinded, Dose-escalation Study of rAAV1-PG9DP Recombinant AAV Vector Coding for PG9 Antibody in Healthy Male Adults (ClinicalTrials.gov Identifier: NCT01937455.
Alhakamy, N.A. et al. "Noncovalently associated cell-penetrating peptides for gene delivery applications," Therapeutic delivery 4: 741-757, Jun. 2013.
Aluwe et al. "Effect of surgical castration, immunocastration and chicory-diet on the meat quality and palatability of boars," Meat Science 94: 402-407, Jul. 2013.
Amatayakul-Chantler, S. et al. "Effects on performance and carcass and meat quality attributes following immunocastration with the gonadotropin releasing factor vaccine Bopriva or surgical castration of Bos indicus bulls raised on pasture in Brazil," Meat Science 95: 78-84, Sep. 2013.
Amatayakul-Chantler, S. et al. "Immunocastration of Bos indicus × Brown Swiss bulls in feedlot with gonadotropin-releasing hormone vaccine Bopriva provides improved performance and meat quality," Journal of animal science 90: 3718-3728, 2012.
An, G. et al. "In Vitro and in Vivo Studies Evaluating Recombinant Plasmid Pcxn2-mlzumo as a Potential Immunocontraceptive Antigen," Am J Reprod Immunol 61: 227-235, 2009.
Arimura, A. et al. "Production of Antiserum to LH-Releasing Hormone (LH-RH) Associated with Gonadal Atrophy in Rabbits: Development of Radioimmunoassays for LH-RH," Endocrinology 93: 1092-1103, 1973.
Ausubel et al., eds., Current Protocols in Molecular Biology, John Wiley & Sons, NY, 1998.
Avella, M.A. et al. "The molecular basis of gamete recognition in mice and humans," Molecular utei reproduction 19:279-289, Jan. 17, 2013.
Balazs, A.B. et al. "Antibody-based protection against HIV infection by vectored immunoprophylaxis," Nature 481, 81-84, 2012.
Balazs, A.B. et al. "Broad protection against influenza infection by vectored immunoprophylaxis in mice," Nat Biotechnol 31: 647-652, Jun. 2, 2013.
Barfield, J.P. et al. "Fertility control in wildlife: humans as a model," Contraception 73: 6-22, 2006.
Batorek et al., "Meta-analysis of the effect of immunocastration on production performance, reproductive organs and boar taint compounds in pigs" Animal 6(8):1330-1338, 2012.
Belldegrun et al. "Human Renal Carcinoma Line Transfected With Interleukin-2 and/or Interferon α Gene(s): Implications for Live Cancer Vaccines," J Natl Cancer Inst 85: 207-216, 1993.
Benavides Valades, G. et al. "Non-invasive assessment of the reproductive cycle in free-ranging female African elephants (*Loxodonta uteiniz*) treated with a gonadotropin-releasing hormone (GnRH) Vaccine for inducing anoestrus," Reproductive biology and endocrinology 10: 63, 2012.
Bird, "Single-chain antigen-binding proteins," Science 242: 423-442, 1988.
Bleil, J.D. et al, "Identification of a ZP3-binding protein on acrosome-intact mouse sperm by photoaffinity crosslinking," Proc Natl Acad Sci USA 87: 5563-5567, 1990.
Boesen et al. "Circumvention of chemotherapy-induced myelosuppression by transfer of themdr1 gene," Biotherapy 6: 291-302, 1993.
Bonneau et al., "The Effects of Immunization Against Luteinizing Hormone-Releasing Hormone on Performance, Sexual Development, and Levels of Boar Taint-Related Compounds in Intact Male Pigs," Journal of Animal Science 72:14-20, 1994.
Boue, F. et al. "Cases of Human Infertility Are Associated with the Absence of P34H, an Epididymal Sperm Antigen'," Biol Reprod 54: 1018-1024, 1996.
Bout et al. "Lung Gene Therapy: In Vivo Adenovirus-Mediated Gene Transfer to Rhesus Monkey Airway Epithelium," Human Gene Therapy 5: 3-10, 1994.

Buchlis, G. et al. "Factor IX expression in skeletal muscle of a severe hemophilia B patient 10 years after AAV-mediated gene transfer," Blood 119: 3038-3041, 2012.
Burkart, A.D. et al. "Ovastacin, a cortical granule protease, cleaves ZP2 in the zona pellucida to prevent polyspermy" J Cell Biol 197, 37-44, 2012.
Calcedo, R. et al. "Adeno-associated virus antibody profiles in newborns, children, and adolescents," Clinical and Vaccine Immunology : CVI 18, 1586-1588, 2011.
Calcedo, R. et al. "Worldwide epidemiology of neutralizing antibodies to adeno-associated viruses," The Journal of Infectious Diseases 199, 381-390, 2009.
Chen, S.-J., et al. "Enhancing the Utility of Adeno-Associated Virus Gene Transfer through Inducible Tissue-Specific Expression," Hum Gene Ther Methods. 24: 270-278, Aug. 20, 2013.
Chen, Y. et al. "Construction of sperm-specific lactate dehydrogenase DNA vaccine and experimental study of its immuno-contraceptive effect on mice," Science in China Series C, Life sciences / Chinese Academy of Sciences 51: 308-316, 2008.
Chothia et al. "Structural determinants in the sequences of immunoglobulin variable domain," J Mol Biol 278: 457-479, 1998.
Ciciliot, S. et al. "Regeneration of mammalian skeletal muscle. Basic mechanisms and clinical implications," Curr Pharm Des 16, 906-914, 2010.
Clarke, I.J. "Two decades of measuring GnRH secretion," Reproduction Supplement 59: 1-13, 2002.
Clarke, I.J. et al. "Active immunization of ewes against luteinizing hormone releasing hormone, and its effects on ovulation and gonadotrophin, prolactin and ovarian steroid secretion," The Journal of endocrinology 78: 39-47, 1978.
Cline "Perspectives for gene therapy: Inserting new genetic information into mammalian cells by physical techniques and viral vectors," Pharmac Ther 29: 69-92, 1985.
Clowes et al. "Long-Term Biological Response of Injured Rat Carotid Artery Seeded with Smooth Muscle Cells Expressing Retrovirally Introduced Human Genes," J Clin Invest 93: 644-651, 1994.
Contraceptive Technology, Edited by Robert A. Hatcher, James Trussell and Anita L. Nelson. PDR Network, 19th edition, 2008.
Cooper, D.W. et al. "Immunocontraception of mammalian wildlife: ecological and immunogenetic issues," Reproduction 132: 821-828, 2006.
Cotten et al. "Receptor-mediated transport of DNA into eukaryotic cells," Meth Enzymol 217: 618-644, 1993.
Cox, J. et al. "Andromeda: a peptide search engine integrated into the MaxQuant environment," J Proteome Res 10, 1794-1805, 2011.
Cox, J. et al. "MaxQuant enables high peptide identification rates, individualized p.p.b.-range mass accuracies and proteome-wide protein quantification," Nat Biotechnol 26, 1367-1372, 2008.
D'Occhio et al., "Sustained testicular atrophy in bulls actively immunized against GnRH: potential to control carcase characteristics," Animal Reproduction Science 66: 47-58, 2001.
Darroch, J.E. et al. "Trends in contraceptive need and use in developing countries in 2003, 2008, and 2012: an analysis of national surveys," Lancet 381, 1756-1762, May 2013.
Davies, B. et al. "Targeted Deletion of the Epididymal Receptor HE6 Results in Fluid Dysregulation and Male Infertility," Mol Cell Biol 24: 8642-8648, 2004.
De la Cruz, A. et al. "Effect of Administration of Anti-Serum to Luteinizing Hormone-Releasing Hormone on Gonadal Function During the Estrous Cycle in the Hamster," Endocrinology 98: 490-497, 1976.
De Nys, H.M. et al. "Vaccination against GnRH may suppress aggressive uteiniz and musth in African elephant (*Loxodonta uteiniz*) bulls—a pilot study," Journal of the South African Veterinary Association 81: 8-15, 2010.
Desjarlais, J.R. et al. "Modulation of antibody effector function," Exp Cell Res 317: 1278-1285, 2011.
Diekman, A.B. et al. "Evidence for a unique N-linked glycan associated with human infertility on sperm CD52: a candidate contraceptive vaccinogen," Immunological reviews 171: 203-211, 1999.

(56) References Cited

OTHER PUBLICATIONS

Diekman, A.B. et al. "N-linked glycan of a sperm CD52 glycoform associated with human infertility," FASEB J 13: 1303-1313, 1999.
Dong,Y. et al. "An in vitro approach for production of non-scar minicircle DNA vectors," Journal of biotechnology 166: 84-87, Jul. 10, 2013.
Donovan, C. et al. "Physiologic responses following gonadotropin-releasing hormone immunization in intact male dogs," Reproduction in Domestic Animals = Zuchthygiene 47 (Suppl 6): 403-405, 2012.
Dorman, E. et al. "Demand for male contraception," Expert Review of Pharmacoeconomics & Outcomes Research 12, 605-613, 2012.
Druce, H.C. et al. "How Immunocontraception Can Contribute to Elephant Management in Small, Enclosed Reserves: Munyawana Population as a Case Study," PloS One 6: e27952, 2011.
Dunshea, F.R. et al. "Vaccination of boars with a GnRH vaccine (Improvac) eliminates boar taint and increases growth performance," Journal of Animal Science 79: 2524-2535, 2001.
East, I.J. et al. "Monoclonal antibodies to the major protein of the murine zona pellucida: Effects on fertilization and early development," Dev Biol 104: 49-56, 1984.
East, I.J. et al. "Monoclonal antibodies to the murine zona pellucida protein with sperm receptor activity: Effects on fertilization and early development," Dev Biol 109: 268-273, 1985.
Engelhardt et al. "Adenovirus-Mediated Transfer of the CFTR Gene to Lung of Nonhuman Primates: Biological Efficacy Study," Human Genet Ther 4: 759-769, 1993.
Ferrantini et al. "IFN-alpha 1 gene expression into a metastatic murine adenocarcinoma (TS/A) results in CD8+ T cell-mediated tumor rejection and development of antitumor immunity. Comparative studies with IFN-gamma-producing TS/A cells," J Immunology 153: 4604-4615, 1994.
Ferrantini et al. "α-Interferon Gene Transfer into Metastatic Friend Leukemia Cells Abrogated Tumorigenicity in Immunocompetent Mice: Antitumor Therapy by Means of Interferon-producing Cells," Cancer Research 53: 1107-1112, 1993.
Found-animals-foundation. http://www.foundanimals.org/pet-spay-neuter/la-lowcost-free-neuter-spay; Original publication date unknown; Version printed on Mar. 22, 2016.
Fraker, M.A. et al. "Long-Lasting, Single-Dose Immunocontraception of Feral Fallow Deer in British Columbia ," Journal of Wildlife Management 66: 1141-1147, 2002.
Fraser, H.M. "Effect of active immunization to luteinizing hormone releasing hormone on gonadotrophin levels in ovariectomized rats," The Journal of endocrinology 64: 191-192, 1975.
Fraser, H.M. et al. "Changes in the ovaries of rats after immunization against luteinizing hormone releasing hormone ," The Journal of endocrinology 77: 85-93, 1978.
Fraser, H.M. et al. "Effect of active immunization to luteinizing hormone releasing hormone on serum and pituitary gonadotropins, testes and accessory sex organs in male rat," The Journal of endocrinology 63: 399-406, 1974.
Fraser, H.M. et al. "Effects of Antibodies to Luteinizing Hormone—Releasing Hormone in the Male Rabbit and on the Rat Oestrous Cycle," Nature 244: 160-161, 1973.
Fraser, H.M. et al. "Gonadotrophin release by a highly active analogue of luteinizing hormone releasing hormone in rats immunized against luteinizing hormone releasing hormone," The Journal of endocrinology 74: 291-296, 1977.
Fu, J. et al. "Anti-ACTL7a antibodies: a cause of infertility," Fertility and sterility 97: 1226-1233, 2012.
Gaj, T. et al. "ZFN, TALEN, and CRISPR/Cas-based methods for genome engineering," Trends Biotechnol. 3 1: 397-405, Jul. 2013.
Galli, R.A. et al. "Evaluation of the accuracy and ease of use of a rapid HIV-1 Antibody Test performed by untrained operators at the point of care," Journal of Clinical Virology 58 Suppl 1, e65-69, Dec. 2013.
Geary, T.W. et al "Use of recombinant gonadotropin-releasing hormone antigens for immunosterilization of beef heifers," Journal of animal science 84: 343-350, 2006.

Gledhill, B. et al. "Effect of passive immunization against LH-RH on gonadotrophin secretion in the ferret," J Reprod Fertil 64: 19-23, 1982.
Gobello, C. "Effects of GnRH antagonists vs agonists in domestic carnivores, a review," Reproduction in Domestic Animals 47 Suppl 6, 373-376, 2012.
Godfrey, S.I. et al. "Immunisation of goat bucks against GnRH to prevent seasonal reproductive and agonistic uteiniz,"Animal Reprod. Sci. 44: 41-54, 1996.
Goldberg, E. "Developmental expression of lactate dehydrogenase isozymes during spermatogenesis," Progress in clinical and biological research 344: 49-52, 1990.
Goodman, R.L. et al. "Kisspeptin neurons from mice to men: similarities and differences," Endocrinology 153, 5105-5118, 2012.
Gracey Maniar, L.E. et al. "Minicircle DNA Vectors Achieve Sustained Expression Reflected by Active Chromatin and Transcriptional Level," Molecular therapy: the journal of the American Society of Gene Therapy 21:131-138, Nov. 27, 2013.
Grandy, J.W. et al. "An animal welfare view of wildlife contraception," Reprod Suppl 60, 1-7, 2002.
Green et al. "Analysis of human tonsil and cancer DNAs and RNAs for DNA sequences of group C (serotypes 1, 2, 5, and 6) human adenoviruses," Proc Natl Acad Sci USA 76: 6606-6610, 1979.
Greenhouse, S. et al. "Antibodies to human ZP3 induce reversible contraception in transgenic mice with 'humanized' zonae pellucidae," Hum Reprod 14: 593-600, 1999.
Griffiths, E.C. et al. "Mechanisms of inactivation of hypothalamic regulatory hormones," Molecular and Cellular Endocrinology 14, 3-17, 1979.
Grossman et al. "Retroviruses: delivery vehicle to the liver," Curr Opin in Genetics and Devel 3: 110-114, 1993.
Gupta et al. "Milestones in contraceptive vaccines development and hurdles in their application," Human Vaccines and immunotherapeutics 10(4): 911-925, 2014; Epub Nov. 21, 2013.
Gupta SK et al. Contraceptive vaccines based on the zone pellucida glycoproteins for dogs and other wildlife population management. Am J Reprod Immunol; 66: 51-62, 2011.
Gupta, S.K. et al. "Vaccines for immunological control of fertility," Reprod Med Biol 9(2): 61-71, 2010.
Gupta, S.K. et al. "Zona pellucida-based contraceptive vaccines for human and animal utility," Journal of reproductive immunology 88: 240-246, 2011.
Hao, M. et al. "Expression of a recombinant bifunctional protein from a chimera of human lutropin receptor and human chorionic gonadotropin β-subunit," Journal of reproductive immunology 63: 123-135, 2004.
Hardy, C.M. et al. "Biological control of vertebrate pests using virally vectored immunocontraception," Journal of Reproductive Immunology 71, 102-111, 2006.
Hearn , J .P. "Immunization against Pregnancy," Proc R Soc Lond B Biol Sci 195: 149-160, 1976.
Heid and Hamm, "Animal welfare versus food quality: Factors influencing organic consumers' preferences for alternatives to piglet castration without anaesthesia," Meat Science 95: 203-211, Oct. 2013.
Herlyn, H. et al. "The molecular evolution of sperm zonadhesin," The International journal of developmental biology 52: 781-790, 2008.
Herr, J.C. et al. "Identification of Human Acrosomal Antigen SP-10 in Primates and Pigs," Biol Reprod 42: 377-382, 1990.
Hicks, M.J. et al. "AAV-Directed Persistent Expression of a Gene Encoding Anti-Nicotine Antibody for Smoking Cessation," Sci Transl Med 4: 140ra87, 2012.
Hodges, J.K. et al. "Effects of immunisation against luteinizing hormone releasing hormone on reproduction of the marmoset monkey *Callithrix jacchus*," Nature 265: 746-748, 1977.
Humane-society. http://www.humanesociety.org/issues/pet_overpopulation/facts/pet_ownership_statistics.html; Original publication date unknown; Version printed on Mar. 22, 2016.
Huston et al. "Protein engineering of antibody binding sites: Recovery of specific activity in an anti-digoxin single-chain Fv analogue produced in *Escherichia coli*," Proc Natl Acad Sci USA 85: 5879-5883, 1988.

(56) References Cited

OTHER PUBLICATIONS

International Search Report and Written Opinion dated Apr. 25, 2014 in PCT Application PCT/US2014/013943.

Isojima, S. et al. "Establishment and characterization of a human hybridoma secreting monoclonal antibody with high titers of sperm immobilizing and agglutinating activities against human seminal plasma," Journal of reproductive immunology 10: 67-78, 1987.

Isojima, S. et al. "Further studies on sperm-immobilizing antibody found in sera of unexplained cases of sterility in women," Am J Obstet Gynecol 112: 199-207, 1972.

Jackson, R.J. et al. "Infertility in mice induced by a recombinant ectromelia virus expressing mouse zona pellucida glycoprotein 3," Biol Reprod 58, 152-159, 1998.

Jagadish, N. et al. "Characterization of immune response in mice to plasmid DNA encoding human sperm associated antigen 9 (SPAG9)," Vaccine 24: 3695-3703, 2006.

Janett, F. et al. "Effect of vaccination against gonadotropin-releasing factor (GnRF) with Bopriva® in the prepubertal bull calf," Animal reproduction science 131: 72-80, 2012.

Janett, F. et al. "Suppression of testicular function and sexual behavior by vaccination against GnRH (EquityTM) in the adult stallion," Animal reproduction science 115: 88-102, 2009.

Janett. F. et al. "Vaccination against gonadotropin-releasing factor (GnRF) with Bopriva significantly decreases testicular development, serum testosterone levels and physical activity in pubertal bulls," Theriogenology 78: 182-188, 2012.

Jang, Y.C. et al. "Skeletal Muscle Stem Cells: Effects of Aging and Metabolism on Muscle Regenerative Function," Cold Spring harb Symp Quant Biol. 76: 101-111, 2011.

Jeffcoate, I.A. et al. "Effect of active immunisation of ewes against synthetic luteinizing hormone releasing hormone," Theriogenology 10: 323-335, 1978.

Jeffcoate, S.L. et al. "Preparation and specificity of antibodies to the decapeptide, luteinizing hormone-releasing hormone (LH-RH)," Immunochemistry 11:75-77, 1974.

Johnson, P.R. et al. "Vector-mediated gene transfer engenders long-lived neutralizing activity and protection against SIV infection in monkeys," Nat Med 15: 901-906, 2009.

Jones et al., "Replacing the complementarity-determining regions in a human antibody with those from a mouse," Nature 321:522-525, 1986.

Jones, B.S. et al. "Improving the safety of cell therapy products by suicide gene transfer," Frontiers in Pharmacology 5, 254, 1-8, 2014.

Kaido, T., et al. "IFN-α1 gene transfection completely abolishes the tumorigenicity of murine B16 melanoma cells in allogeneic DBA/2 mice and decreases their tumorigenicity in syngeneic C57BL/6 mice," Int J Cancer 60: 221-229, 1995.

Kalli, A. et al. "Evaluation and optimization of mass spectrometric settings during data-dependent acquisition mode: focus on LTQ-Orbitrap mass analyzers," J Proteome Res 12, 3071-3086, May 5, 2013.

Kaneda et al. "Increased expression of DNA cointroduced with nuclear protein in adult rat liver," Science 243: 375, 1989.

Kay, M.A. "State-of-the-art gene-based therapies: the road ahead," Nat Rev Genet 12, 316-328, 2011.

Kay, M.A. et al. "A robust system for production of minicircle DNA vectors," Nat Biotechnol 28: 1287-1289, 2010.

Keene, J.L. et al. "Recombinant deglycosylated human FSH is an antagonist of human FSH action in cultured granulosa cells," Endocrine Journal 2, 175-180, 1994.

Kiem et al. "Retrovirus-Mediated Gene Transduction Into Canine Peripheral Blood Repopulating Cells," Blood 83: 1467-1473, 1994.

Kim, Y.H. et al. "Compartmentalization of a Unique ADP/ATP Carrier Protein SFEC (Sperm Flagellar Energy Carrier, AAC4) with Glycolytic Enzymes in the Fibrous Sheath of the Human Sperm Flagellar Principal Piece," Dev Biol 302: 463-476, 2007.

Kirchhoff, C. and Hale, G. "Cell-to-cell transfer of glycosylphosphatidylinositol-anchored membrane proteins during sperm maturation," Molecular human reproduction 2(3): 177-184, 1996.

Kirkpatrick, J.F. et al. "Contraceptive Vaccines for Wildlife: A Review," Am J Reprod Immunol 66: 40-50, 2011.

Kirkpatrick, J.F. et al. "The practical side of immunocontraception: zona proteins and wildlife," Journal of reproductive immunology 83: 151-157, 2009.

Knapp, R.J. et al. "High affinity monoclonal antibodies to luteinizing hormone-releasing hormone. Preparation and binding studies," J Neuroimmunol 6, 361-371, 1984.

Koch, Y. et al. "Suppression of gonadotropin secretion and prevention of ovulation in the rat by antiserum to synthetic gonadotropin-releasing hormone," Biochem Biophys Res Commun 55: 623-629, 1973.

Koller et al. "Inactivating the $\beta_2$-microglobulin locus in mouse embryonic stem cells by homologous recombination," Proc Natl Acad Sci USA 86: 8932-8935, 1989.

Komori, S. et al. "Production of heavy-chain class-switch variants of human monoclonal antibody by recombinant DNA technology," Clinical and experimental immunology 71: 508-516, 1988.

Kormann, M.S. et al. "Expression of therapeutic proteins after delivery of chemically modified mRNA in mice," Nat Biotechnol 29, 154-157, 2011.

Kozarsky and Wilson "Gene therapy: adenovirus vectors," Current Opinion in Genetics and Development 3: 499-503, 1993.

Krause, W.K.H. and Naz, R.K., eds. in Immune Infertility (Berlin, Germany: Springer-Verlag), 2009.

Krutskikh, A. et al. "Epididymal protein Rnase10 is required for posttesticular sperm maturation and male fertility," FASEB J 26: 4198-4209, 2012.

Kumar, P. et al. "Gonadotropin-releasing hormone analogs: Understanding advantages and limitations," Journal of Human Reproductive Sciences 7, 170-174, 2014.

Kurosawa, N. et al. "Rapid production of antigen-specific monoclonal antibodies from a variety of animals," BMC biology 10: 80, 2012.

Kurosawa, N. et al. "Target-selective homologous recombination cloning for high-throughput generation of monoclonal antibodies from single plasma cells," BMC biotechnology 11: 39, 2011.

Kutmeier et al. "Assembly of humanized antibody genes from synthetic oligonucleotides using a single-round PCR," BioTechniques 17: 242, 1994.

Kutzler, M. and Wood, A. "Non-surgical methods of contraception and sterilization," Theriogenology 66: 514-525, 2006.

Lea, I.A. et al. "Autoimmunogenicity of the human sperm protein Sp17 in vasectomized men and identification of linear B cell epitopes," Fertility and sterility 67: 355-361, 1997.

Lee, E.C. et al. "Complete humanization of the mouse immunoglobulin loci enables efficient therapeutic antibody discovery," Nat Biotechnol 32, 356-363, 2014.

Lefevre, A. et al. "Characterization and isolation of SOB2, a human sperm protein with a potential role in oocyte membrane binding," Molecular human reproduction 3: 507-516, 1997.

Leone, P. et al. "Long-term follow-up after gene therapy for canavan disease," Sci Transl Med 4, 165ra163, 2012.

Levy, J. K. "Contraceptive Vaccines for the Humane Control of Community Cat Populations," Am J Reprod Immunol 66: 63-70, 2011.

Levy, J.K. et al. "Long-term fertility control in female cats with GonaCon™, a GnRH immunocontraceptive," Theriogenology 76: 1517-1525, 2011.

Li, J. et al. "Vectored antibody gene delivery mediates long-term contraception," Current Biology 25: R811-R826, 2015.

Li, L. et al. "Production and characterization of novel recombinant adeno-associated virus replicative-form genomes: a eukaryotic source of DNA for gene transfer," PloS One 8: e69879, Aug. 1, 2013a.

Li, W. et al. "Tex101 is essential for male fertility by affecting sperm migration into the oviduct in mice," Journal of molecular cell biology 5:345-347, Aug. 22, 2013.

Li., J. et al. Supplemental Information for "Vectored antibody gene delivery mediates long-term contraception," 2015.

Limberis, M.P. et al. "Intranasal Antibody Gene Transfer in Mice and Ferrets Elicits Broad Protection Against Pandemic Influenza," Sci Transl Med 5: 187ra72, May 29, 2013.

(56) References Cited

OTHER PUBLICATIONS

Lincoln, G.A. et al. "Blockade of Episodic Secretion of Luteinizing Hormone in the Ram by the Administration of Antibodies to Luteinizing Hormone Releasing Hormone," Biol Reprod 21:1239-1245, 1979.
Lishko, P.V. et al. "The Control of Male Fertility by Spermatozoan Ion Channels," Annual review of physiology 74: 453-475, 2012.
Lloyd, M.L. et al. "Immunocontraception is induced in BALB/c mice inoculated with murine cytomegalovirus expressing mouse zona pellucida 3," Biol Reprod 68, 2024-2032, 2003.
Locke. S.L. et al. "Effectiveness of Spayvac® for Reducing White-tailed Deer Fertility," Journal of wildlife diseases 43: 726-730, 2007.
Loeffler and Behr "Gene transfer into primary and established mammalian cell lines with lipopolyamine-coated DNA," Meth Enzymol 217: 599-618, 1993.
Ishino, T. et al. "Engineering a Monomeric Fc Domain Modality by N-Glycosylation for the Half-life Extension of Biotherapeutics," J Bid Chem. 288: 16529-37, Apr. 24, 2013.
Isojima, S. et al. "Immunologic analysis of sperm-immobilizing factor found in sera of women with unexplained sterility," Am J Obstet Gynecol 101 : 677-683, 1968.
Lucas, X. "Clinical use of deslorelin (GnRH agonist) in companion animals: a review," Reproduction in Domestic Animals 49 Suppl 4, 64-71, 2014.
Macdonald, L.E. et al. "Precise and in situ genetic humanization of 6 Mb of mouse immunoglobulin genes," Proc Natl Acad Sci U S A 111, 5147-5152, 2014.
Mackenzie, S.M. et al. "Immunocontraceptive effects on female rabbits infected with recombinant myxoma virus expressing rabbit ZP2 or ZP3," Biol Reprod 74, 511-521, 2006.
Majowicz et at. "Mir-142-3p target sequences reduce transgene-directed immunogenicity following intramuscular adeno-associated virus 1 vector-mediated gene delivery," Journal of Gene medicine. 15: 219-232, Jul. 16, 2013.
Majumdar, R. et al. "Docking and free energy simulations to predict conformational domains involved in Hcg-LH receptor interactions using recombinant antibodies," Proteins 79: 3108-3122, 2011.
Mastrangeli et al. "Diversity of airway epithelial cell targets for in vivo recombinant adenovirus-mediated gene transfer," J Clinical Invest 91: 225-234, 1993.
Matzuk, M.M. et al. "Site specificity of the chorionic gonadotropin N-linked oligosaccharides in signal transduction," J Biol Chem 264, 2409-2414, 1989.
McCormack, J.T. et al. "The Effect of Luteinizing Hormone Releasing Hormone (LHRH) Antiserum Administrationon Gonadotropin Secretion in the Rhesus Monkey," Endocrinology 100: 663-667, 1977.
McLaughlin, E.A. et al. "Cloning and sequence analysis of rat fertilin alpha and beta-developmental expression, processing and immunolocalization," Molecular human reproduction 3: 801-809, 1997.
McLaughlin, E.A. et al. "Is there a role for immunocontraception?," Molecular and cellular endocrinology 335: 78-88, 2011.
Meloen et al., "Efficient immunocastration of male piglets by immunoneutralization of GnRH using a new GnRH-like peptide," Vaccine 12:741-746, 1994.
Midgley Jr. A.R., et al. "Nonclassical secretory dynamics of LH revealed by hypothalamo-hypophyseal portal sampling of sheep," Endocrine 6: 133-143, 1997.
Miller et al. "Use of retroviral vectors for gene transfer and expression," Meth Enzymol 217: 581-599, 1993.
Miller, L.A. et al. "Twenty years of immunocontraceptive research: lessons learned," Journal of Zoo and Wildlife Medicine 44, S84-96, Dec. 2013.
Miller, L.A. et al. "The Single-Shot GnRH Immunocontraceptive Vaccine (GonaCon™) in White-Tailed Deer: Comparison of Several GnRH Preparations," Am J Reprod Immunol 60: 214-223, 2008.

Mingozzi, F. "Immune responses to AAV vectors: overcoming barriers to successful gene therapy," Blood 122, 23-36, Jul. 4, 2013.
Mingozzi, F. et al. "Overcoming preexisting humoral immunity to AAV using capsid decoys," Sci Transl Med 5, 194ra192, Jul. 17, 2013.
Morrison et al. "Chimeric human antibody molecules: Mouse antigen-binding domains with human constant region domains," Proc Natl Acad Sci 81(21): 6851-6855, 1984.
Munks, M.W. "Progress in Development of Immunocontraceptive Vaccines for Permanent Non-surgical Sterilization of Cats and Dogs," Reproduction in Domestic Animals 47 (Suppl 4): 223-227, 2012.
Murphy, A.J. et al. "Mice with megabase humanization of their immunoglobulin genes generate antibodies as efficiently as normal mice," Proc Natl Acad Sci U S A 111, 5153-5158, 2014.
Muzyczka "Use of adeno-associated virus as a general transduction vector for mammalian cells," Curr Topics in Microbial Immunol 158: 97, 1992.
Nafissi, N. et al. "Construction and Characterization of an in-vivo Linear Covalently Closed DNA Vector Production System," Microbial cell factories 11: 154, 2012.
Nath, Richa. "Generation and characterisation of plant produced recombinant antibodies specific to LHRH for treatment of sex hormone dependent diseases," Doctor of Natural Sciences Dissertation for RWTH Aachen University, 2003.
Nathwani, A.C. et al. "Adenovirus-Associated Virus Vector-Mediated Gene Transfer in Hemophilia B," The New England journal of medicine 365: 2357-2365, 2011.
Naz et al. "Antibodies to sperm-specific human FA-1 inhibit in vitro fertilization in rhesus monkeys: development of a simian model for testing of anti-FA-1 contraceptive vaccine," Journal of reproductive immunology 27: 111-121, 1994.
Naz et al. "Passive Immunization for Immunocontraception: Lessons Learned from Infections Diseases," Frontiers in Bioscience 9:2457-2465, 2004.
Naz, R.K. "Recent progress toward development of vaccines against conception," Expert Review of Vaccines 13, 145-154, 2014.
Naz, R.K. et al. "Recent advances in contraceptive vaccine development: a mini-review," Hum Reprod 20: 3271-3283, 2005.
Neuberger et al. "Recombinant antibodies possessing novel effector functions," Nature 312: 604-608, 1984.
Nimmerjahn, F. "Fcgamma receptors as regulators of immune responses," Nature Rev Immunology 8, 34-47, 2008.
O. Vafa et al. "An engineered Fc variant of an IgG eliminates all immune effector functions via structural perturbations," Methods 65: 114-26, 2014.
Ogura et al. "Implantation of Genetically Manipulated Fibroblasts into Mice as Antitumor a-Interferon Therapy," Cancer Research 50: 5102-5106, 1990.
Oi, V.T. et al. "Correlation between segmental flexibility and effector function of antibodies," Nature 307, 136-140, 1984.
O'Rand, M. G. "Reversible Immunocontraception in Male Monkeys Immunized with Eppin," Science 306: 1189-1190, 2004.
Oxfordpets.com. http://www.oxfordpets.com/index.php?option=com_content&view=article&id=61.
Pai, M. et al. "Immunocontraception in Eastern Gray Squirrels (*Sciurus carolinensis*): Morphologic Changes in Reproductive Organs," Journal of zoo and wildlife medicine: official publication of the American Association of Zoo Veterinarhms 42: 718-722, 2011.
Pasadena-humane-society. http://www.pasadenahumane.org/site/PageServer?pagename=services_snip_faq; Original publication date unknown; Version printed on Mar. 22, 2016.
Pausch et al. "A Nonsense Mutation in TMEM95 Encoding a Nondescript Transmembrane Protein Causes Idiopathic Male Subfertility in Cattle," PLoS Genet. 10(1):e1004044, 2014.
Pickard, A.R. and Holt, W.V. "Contraception in wildlife," The journal of family planning and reproductive health care / Faculty of Family Planning & Reproductive Health Care, Royal College of Obstetricians & Gynaecologists 33: 48-52, 2007.
Pittelkow and Scott "New Techniques for the In Vitro Culture of Human Skin Keratinocytes and Perspectives on Their Use for Grafting of Patients With Extensive Burns," Mayo Clinic Proc 61: 771, 1986.

(56) References Cited

OTHER PUBLICATIONS

Powers, J.G. et al. "Effects of Gonadotropin-Releasing Hormone Immunization on Reproductive Function and Behavior in Captive Female Rocky Mountain Elk (*Cereus elaphus* nelsoni)," Biol Reprod 85: 1152-1160, 2011.
Presta, L.G. "Engineering of therapeutic antibodies to minimize immunogenicity and optimize function," Advanced Drug Delivery Reviews 58: 640-656, 2006.
Price, E.O. et al. "Aggressive behavior is reduced in bulls actively immunized against gonadotropin-releasing hormone," Journal of animal science 81: 411-415, 2003.
Primakoff, P. et al. "Fully effective contraception in male and female guinea pigs immunized with the sperm protein PH-20," Nature 335: 543-546, 1988.
Rankin, T.L. et al. "Human ZP3 restores fertility in Zp3 null mice without affecting order-specific sperm binding," Development 125: 2415-2424, 1998.
Reichmann et al., "Reshaping human antibodies for therapy," Nature 332:323-327, 1988.
Reubel, G.H. et al. "Experimental inoculation of European red foxes with recombinant vaccinia virus expressing zona pellucida C proteins," Vaccine 23, 4417-4426, 2005.
Rheinwald "Serial cultivation of normal human epidermal keratinocytes," Meth Cell Bio 21A: 229-254, 1980.
Robbins, S.C. et al. "Assessment of the immunological and biological efficacy of two different doses of a recombinant GnRH vaccine in domestic male and female cats (*Fells catus*)," Journal of reproductive immunology 64: 107-119, 2004.
Roberts, K.P. et al. "Inhibition of Capacitation-Associated Tyrosine Phosphorylation Signaling in Rat Sperm by Epididymal Protein Crisp-1," Biol Reprod 69: 572-581, 2003.
Robertson, I.S. et al. The Veterinary record 105: 556-557, 1979.
Robertson, I.S. et al. The Veterinary record 108: 381-382, 1981.
Robertson, I.S. et al. The Veterinary record 111: 529-531, 1982.
Ronald, J.A. et al. "Development and Validation of Non-Integrative, Self-Limited, and Replicating Minicircles for Safe Reporter Gene Imaging of Cell-Based Therapies," PLoS One e73138. doi: 10.1371/journal.pone.0073138, Aug. 28, 2013.
Rosenberg, J.B. et al. "AAVrh.10-Mediated Expression of an Anti-Cocaine Antibody Mediates Persistent Passive Immunization That Suppresses Cocaine-Induced Behavior," Hum Gene Ther 23: 451-459, 2012.
Rosenfeld et al. "Adenovirus-mediated transfer of a recombinant alpha 1-antitrypsin gene to the lung epithelium in vivo," Science 252: 431-434, 1991.
Rosenfeld et al. "In vivo transfer of the human cystic fibrosis transmembrane conductance regulator gene to the airway epithelium," Cell 68: 143-155, 1992.
Saint Louis Zoo. http://www.stlzoo.org/animals/scienceresearch/contraceptioncenter/contraceptionrecommendatio/contraceptionmethods/; Original publication date unknown; Version printed on Mar. 22, 2016.
Salmons et al. "Targeting of Retroviral Vectors for Gene Therapy," Human Gene Therapy 4: 129-141, 1993.
Sambrook et al., Molecular Cloning, A Laboratory Manual, 2nd Ed., Cold Spring Harbor Laboratory, Cold Spring Harbor, N.Y., 1989.
Samoylov, A. et al. Zuchthygiene 47 (Suppl 6):406-411, 2012.
Samuel, A.S. et al. "Isolation of human single chain variable fragment antibodies against specific sperm antigens for immunocontraceptive development," Hum Reprod 23, 1324-1337, 2008.
Samulski, R.J. et al. "AAV-mediated gene therapy for research and therapeutic purposes," Annu. Rev. Virol. 1, 427-451, 2014.
Santodonato, et al. "Cure of Mice with Established Metastatic Friend Leukemia Cell Tumors by a Combined Therapy with Tumor Cells Expressing Both Interferon-α1 and Herpes Simplex Thymidine Kinase Followed by Ganciclovir," Human Gene Therapy 7: 1-10, 1996.
Santodonato, et al. "Local and systemic antitumor response after combined therapy of mouse metastatic tumors with tumor cells expressing IFN-a and HSVtk: perspectives for the generation of cancer vaccines," Gene Therapy 4: 1246-1255, 1997.
Saunders, A. et al. "Novel recombinant adeno-associated viruses for Cre activated and inactivated transgene expression in neurons," Frontiers in neural circuits 6: 47, 2012.
Sawai, H. et al. "Direct Production of the Fab Fragment Derived From the Sperm Immobilizing Antibody Using Polymerase Chain Reaction and cDNA Expression Vectors," Am J Reprod immunology 34: 26-34, 1995.
Schakowski, F. et al. "Minimal Size MIDGE Vectors Improve Transgene Expression In Vivo," In Vivo 21 : 17-23, 2007.
Schneider, F. et al. "Gonadotropin-releasing hormone (GnRH) and its natural analogues: A review," Theriogenology 66: 691-709, 2006.
Schnepp, B.C. et al. "Vector-mediated antibody gene transfer for infectious diseases," Adv Exp Med Biol 848, 149-167, 2015.
Schulz, M.H. et al. "Oases: robust de novo TNA-seq assembly across the dynamic range of expression levels," Bioinformatics 28, 1086-92, 2012.
Schwartz et al. "Clinical Evaluation of Live, Oral Types 1, 2, and 5 Adenovirus Vaccines," Am Rev Respir Dis 109: 233-238, 1974.
Sen, D. "Improving clinical efficacy of adeno associated vectors by rational capsid bioengineering," Journal of Biomedical Science 21, 103, 2014.
Shore, N.D. "Experience with degarelix in the treatment of prostate cancer," Therapeutic Advances in Urology 5, 11-24, Jan. 16, 2013.
Short, R.V. et al. "Influence of passive immunization against GnRH on pregnancy and parturition in the tammar wallaby, *Macropus eugenii*," J Reprod Fertil 75: 567-575, 1985.
Silversides, D.W. et al. "Monoclonal antibodies against LHRH: development and immunoactivity in vivo and in vitro," Journal of reproductive immunology 7: 171-184, 1985.
Simms, M.S. et al. "Anti-GnRH antibodies can induce castrate levels of testosterone in patients with advanced prostate cancer," British Journal of Cancer 83, 443-446, 2000.
Singh, M. et al. "Regain of Fertility and Normality of Progeny Born During Below Protective Threshold Antibody Titers in Women Immunized With the HSD-hCG Vaccine," Am J Reprod Immunology 39: 395-398, 1998.
Skerra et al. "Assembly of a functional immunoglobulin Fv fragment in *Escherichia coli*," Science 240: 1038-1041, 1988.
Smith, K. "Rapid generation of fully human monoclonal antibodies specific to a vaccinating antigen," Nature protocols 4: 372-384, 2009.
Stemple et al. "Isolation of a stem cell for neurons and glia from the mammalian neural crest ," Cell 71 : 973-985, 1992.
Stevenson, T.J. et al. "Gonadotropin-releasing hormone plasticity: a comparative perspective," Frontiers in Neuroendocrinology 33, 287-300, 2012.
Stribling et al. "Aerosol gene delivery in vivo," Proc Natl Acad Sci USA 189: 11277-11281, 1992.
Strive, T. et al. "Development of canine herpesvirus based antifertility vaccines for foxes using bacterial artificial chromosomes," Vaccine 24, 980-988, 2006.
Swann, P.G. et al. "Considerations for the development of therapeutic monoclonal antibodies," Current opinion in immunology 20: 493-499, 2008.
Takahashi , M. et al. "Active Immunization of Female Rats with Luteinizing Hormone Releasing Hormone (LHRH)," Biol Reprod 18: 754-761, 1978.
Takeda et al. "Construction of chimaeric processed immunoglobulin genes containing mouse variable and human constant region sequences," Nature 314: 452-454, 1985.
Talwar, G.P. "A unique vaccine for control of fertility and therapy of advanced-stage terminal cancers ectopically expressing human chorionic gonadotropin," Ann NY Acad Sci 1283: 50-56, Apr. 2013.
Talwar, G.P. "Fertility regulating and immunotherapeutic vaccines reaching human trials stage," Human reproduction update 3: 301-310, 1997.
Talwar, G.P. et al. "A vaccine that prevents pregnancy in women," Proc Natl Acad Sci USA 91: 8532-8536, 1994.

(56) References Cited

OTHER PUBLICATIONS

Talwar, G.P. et al. "Gonadotropin-releasing hormone/human chorionic gonadotropin based recombinant antibodies and vaccines," Journal of reproductive immunology 83: 158-163, 2009.
Talwar, G.P. et al. "The HSD-hCG Vaccine Prevents Pregnancy in Women: Feasibility Study of a Reversible Safe Contraceptive Vaccine," Am J Reprod Immunol 37: 153-160, 1997.
Theubet, G. et al. Schweizer Archiv fur Tierheilkunde 152: 459-469, 2010.
Thompson "Immunization against GnRH in male species (comparative aspects)," Animal Reproduction Science 60-61: 459-469, 2000.
Thornton, P. et al. "Review of outcomes after cessation of gonadotropin-releasing hormone agonist treatment of girls with precocious puberty," Pediatric Endocrinology Reviews 11, 306-317, 2014.
Tollner, T.L. et al. "Macaque sperm coating protein DEFB126 facilitates sperm penetration of cervical mucus," Hum Reprod 23: 2523-2534, 2008.
Tzioufas, A.G. et al. "Idiotype, anti-idiotype network of autoantibodies: pathogenetic considerations and clinical application," Autoimmunity Reviews 9, 631-633, 2010.
Van Der Lende, T. "Generation and applications of monoclonal antibodies for livestock production," Biotechnology advances 12: 71-87, 1994.
Vargas-Pino, F. et al. "Concomitant administration of GonaConTMand rabies vaccine infemale dogs (*Canis familiaris*) in Mexico," Vaccine 31: 4442-4447, Jul. 16, 2013.
Verhoeyen et al. "Reshaping human antibodies: grafting an antilysozyme activity," Science, 239: 1534-1536, 1988.
Vidal, A. et al. "A Dynamical Model for the Control of the Gonadotrophin-Releasing Hormone Neurosecretory System," J. Neuroendocrinology 22: 1251-1266, 2010.
Vulin, A. et al. "Muscle Function Recovery in Golden Retriever Muscular Dystrophy After AAV1-U7 Exon Skipping," The journal of the American Society of Gene Therapy 20: 2120-2133, 2012.
Walker, J. et al. "Totally synthetic peptide-based immunocontraceptive vaccines show activity in dogs of different breeds," Vaccine 25: 7111-7119, 2007.
Walsh et al. "Gene therapy for human hemoglobinopathies," Proc Soc Exp Biol Med 204: 289-300, 1993.
Walsh, G. "Biopharmaceutical benchmarks 2014," Nat Biotechnol 32, 992-1000, 2014.
Wang D.G. et al. "Investigation of Recombinant Mouse Sperm Protein Izumo as a Potential Immunocontraceptive Antigen," Am J Reprod Immunol 59:225-234, 2008.
Wang, et al. "A packaging cell line for propagation of recombinant adenovirus vectors containing two lethal gene-region deletions," Gene Therapy 2: 775-783, 1995.
Wang, M. et al. "Immunocontraceptive potential of the Ig-like domain of Izumo," Molecular reproduction and development 76: 794-801, 2009.
Ward et al. "Binding activities of a repertoire of single immunoglobulin variable domains secreted from *Escherichia coli*," Nature 341: 544-54, 1989.
Weiner, G.J. "Building better monoclonal antibody-based therapeutics," Nat Rev Cancer 15, 361-370, 2015.
Wenzinger, B. et al. "The use of a GnRH vaccine in mares and stallions to influence undesirable behavior: a retrospective study of 31 cases," Schweizer Archiv fur Tierheilkunde 152: 373-377, 2010.
Wilkinson, I.C. et al. "Monovalent IgG4 molecules," mAbs 5:406-417, Apr. 8, 2013.
Wilson et al. "Vehicles for gene therapy," Nature 365: 691-692, 1993.
Winter, G. and Harris, W.J. "Humanized antibodies," Immunology today 14: 243-246, 1993.
Wong, S.P. et al. "Genetic modification of dividing cells using episomally maintained S/MAR DNA vectors," Molecular Therapy—Nucleic Acids 2, e115; doi: 10.1038/mtna.2013.40, Aug. 13, 2013.
Wu et al. "Receptor-mediated in Vitro Gene Transformation by a Soluble DNA Carrier System," J Biol Chem 262: 4429-4432, 1987.
Wu, X. et al. "Development of combined vaccines for rabies and immunocontraception ,"Vaccine 27: 7202-7209, 2009.
Yamasaki, N. et al. "Complementary DNA for a human subgroup IV immunoglobulin λ-chain," Molecular Immunology 24: 981-985, 1987.
Yanagimachi , R. et al, "Immunological block to mammalian fertilization: Survival and organ distribution of immunoglobulin which inhibits fertilization in vivo," Proc Natl Acad Sci USA 73: 2405-2408, 1976.
Yang et al. "Inactivation of E2a in recombinant adenoviruses improves the prospect for gene therapy in cystic fibrosis," Nature Genet 7: 362-369, 1994.
Yin, H. et al. "Non-viral vectors for gene-based therapy," Nat Rev Genet 15, 541-555, 2014.
Yin, L. et al. "Therapeutic outcomes, assessments, risk factors and mitigation efforts of immunogenicity of therapeutic protein products," Cellular Immunology 295, 118-126, 2015.
Yoder, C.A. et al. "Effect of GonaConTM vaccine on black-tailed prairie dogs: Immune response and health effects," Vaccine 29: 233-239, 2010.
Yoo, J. et al. "Conversion of lysine 91 to methionine or glutamic acid in human choriogonadotropin alpha results in the loss of cAMP inducibility," J Biol Chem 266, 17741-17743, 1991.
Yudin, A.I. et al. "ESP13.2, a Member of the β-Defensin Family, Is a Macaque Sperm Surface-Coating Protein Involved in the Capacitation Process," Biol Reprod 69: 1118-1128, 2003.
Zeltins, A. "Construction and characterization of virus-like particles: a review," Molecular biotechnology 53: 92-107, Jan. 2013.
Zeng, H. et al. "Lys91 and His90 of the alpha-subunit are crucial for receptor binding and hormone action of follicle-stimulating hormone (FSH) and play hormone-specific roles in FSH and human chorionic gonadotropin," Endocrinology 136, 2948-2953, 1995.
Zhang, et al. "Treatment of a human breast cancer xenograft with an adenovirus vector containing an interferon gene results in rapid regression due to viral oncolysis and gene therapy," Cancer Gene Therapy 3: 31-38, 1996.
Zijlstra et al. "Germ-line transmission of a disrupted β 2microglobulin gene produced by homologous recombination in embryonic stem cells," Nature 342: 435-438, 1989.
Zuris, J.A. et al. "Cationic lipidmediateddelivery of proteins enables efficient protein-based genome editing in vitro and in vivo," Nat Biotechnol 33, 73-80, 2015.
ASPCA. http://www.aspca.org/about-us/faci/pet-statistics.aspx. This document is not available. It is noted that the document appears to have been publicly available prior to Feb. 1, 2013. ASPCA; http://www.aspca.org/animal-homelessness/shelter-intake-and-surrender/pet-statistics is submitted herewith in place of this. The original publication date of http://www.aspca.org/animal-homelessness/shelter-intake-and-surrender/pet-statistics is unknown. The present version was printed on Aug. 5, 2016; 11 pages.
Chamley, L.W. et al., "Antisperm antibodies and conception," Seminars in Immunopathology, vol. 29, pp. 169-184, 2007.
Carson et al., "Production and biological activity of murine monoclonal antibodies against GnRH," Theriogenology, vol. 48, No. 2, pp. 193-207, 1997.
Chien, W.M. et al., "Genomic DNA recombination with cell-penetrating peptide-tagged cre protein in mouse skeletal and cardiac muscle," Genesis, vol. 52, pp. 695-701, 2014.
Clarke, I.J. "Control of GnRH secretion: one step back," Frontiers in Neuroendocrinology, vol. 32, pp. 367-375, 2011.
Clarke, I.J. "Interface between metabolic balance and reproduction in ruminants: focus on the hypothalamus and pituitary," Hormones and Behavior, vol. 66, pp. 15-40, 2014.
Coffin, J.M. "Retroviridae: The viruses and their replication," Chapter 26, Fundamental Virology, Third Edition, Edited by Fields, B.N. et al., Lippincott-Raven Publishers, Philadelphia, 1996.
Crawford, E.D et al., "Long-term tolerability and efficacy of degarelix: 5-year results from a phase III extension trial with a 1-arm crossover from leuprolide to degarelix," Urology, vol. 83, No. 5, pp. 1122-1128, 2014.
Deehan, M. et al., "Managing unwanted immunogenicity of biologicals," Autoimmunity Reviews, vol. 14, pp. 569-574, 2015.

(56) References Cited

OTHER PUBLICATIONS

Dismuke, D.J. et al., "Biosafety of recombinant adeno-associated virus vectors," Current Gene Therapy, vol. 13, pp. 434-452, Dec. 2013.
Ferro, V.A. et al., "Reproductive component vaccine developments for contraceptive and non-contraceptive uses," Expert Opin. Ther. Patents, vol. 21, No. 9, 2011.
McCauley, T.C. et al., "Analysis of a Human Sperm CD52 Glycoform in Primates: Identification of an Animal Model for Immunocontraceptive Vaccine Development," Biology of Reproduction, vol. 66, pp. 1681-1688, 2002.
Miller, A.D., "Retrovirus Packaging Cells," Human Gene Therapy, vol. 1, pp. 5-14, 1990.
Tiller, T. et al., "Cloning and expression of murine Ig genes from single B cells," J. Immunol. Methods, vol. 350, pp. 183-193, 2009.
File History of U.S. Appl. No. 14/206,011.
File History of U.S. Appl. No. 14/631,171.
File History of U.S. Appl. No. 14/837,941.
File History of U.S. Appl. No. 15/164,452.
File History of U.S. Appl. No. 15/970,728.
htttps://www.caltech.edu/news/long-term-contraception-single-shot-48199 Oct. 6, 2015.†
Balazs et al., "Antibody-based protection against HIV infection by vectored immunoprophylaxis," Nature, 481:81-84 (2012) and Supplementary Information (Materials and Methods pp. 1-2).†
Fraser, "Antifertility effects of GnRH" J. Reprod. Fert. 64:503-515 (1982).†
Naz, "Contraceptive Vaccines", Drugs, 65 (5):593-603 (2005).†
Naz, "Recent advances in contraceptive vaccine development: a mini-review," Human Reproduction, 20(12):3271-3283 (2005).†
Levy et al, "Long-term fertility control in female cats with GonaCo, a GnRH immunocontraceptive" 76(8):1517-1525.†

\* cited by examiner
† cited by third party

Fig. 9

HB9094 sequence in AAV:

Signal peptide      variable region      *F2Aopt peptide* atggcgacgggtcaagaacttccctacttcttgcatttggcctgctttgtttgccgtggttacaggagggctcggcaCAGATCCAGTTG
GTGCAGTCTGGACCTGAACTGAAGAAGCCTGGAGAGACAGTCAAGATCTCCTGCAAGGCTTCT
GGATATCCCTTCACAAACTATGGAATGAACTGGGTGAAGCAGGCTCCAGGAAAGGGTTTAAAG
TGGATGGGCTGGATAAACACCTACACTGGAGAGCCAGCATGTGCTGATGACTTCAGGGGACG
GTTTGCCATCTCTTTGGAAACCTCCGCCAGAACTGCCTATTTGCAGATCAACAACCTCATAAAT
GAGGACACGGCAACATATTTCTGTGCAAGAACGGGGGGTGGTAGGTACAACTATGGTATGGA
CTATTGGGGTCAAGGAACCTCAGTCACCGTCTCCAGCGCTAAAACGACACCCCATCTGTCTA
TCCACTGGCCCCTGGATCTGCTGCCCAAACTAACTCCATGGTGACCCTGGGATGCCTGGTCAA
GGGCTATTTCCCTGAGCCAGTGACAGTGACCTGGAACTCTGGATCCCTGTCCAGCGGTGTGC
ACACCTTCCCAGCTGTCCTGCAGTCTGACCTCTACACTCTGAGCAGCTCAGTGACTGTCCCCT
CCAGCACCTGGCCCAGCGAGACCGTCACCTGCAACGTTGCCCACCCGGCCAGCAGCACCAA
GGTGGACAAGAAAATTGTGCCCAGGGATTGTGGTTGTAAGCCTTGCATATGTACAGTCCCAGA
AGTATCATCTGTCTTCATCTTCCCCCCAAAGCCCAAGGATGTGCTCACCATTACTCTGACTCCT
AAGGTCACGTGTGTTGTGGTAGACATCAGCAAGGATGATCCCGAGGTCCAGTTCAGCTGGTTT
GTAGATGATGTGGAGGTGCACACAGCTCAGACGCAACCCCGGGAGGAGCAGTTCAACAGCAC
TTTCCGCTCAGTCAGTGAACTTCCCATCATGCACCAGGACTGGCTCAATGGCAAGGAGTTCAA
ATGCAGGGTCAACAGTGCAGCTTTCCCTGCCCCCATCGAGAAAACCATCTCCAAAACCAAAGG
CAGACCGAAGGCTCCGCAGGTGTACACCATTCCACCTCCCAAGGAGCAGATGGCCAAGGATA
AAGTCAGTCTGACCTGCATGATAACAGACTTCTTCCCTGAAGACATTACTGTGGAGTGGCAGT
GGAATGGGCAGCCAGCGGAGAACTACAAGAACACTCAGCCCATCATGGACACAGATGGCTCT
TACTTCGTCTACAGCAAGCTCAATGTGCAGAAGAGCAACTGGGAGGCAGGAAATACTTTCACC
TGCTCTGTGTTACATGAGGGCCTGCACAACCACCATACTGAAGAGCCTCTCCCACTCTCCT
GGTAAA*cgaaaagaagatcaggttcgggtgcgccagtaaagcagacattaaacttgattgctgaaacttgcaggtgatgt*
*agagtcaaatccaggtcca*atggcaacagggagccgaacctctctgctccttgcttcgggctcctttgcctaccgtggctccaagagggc
tcggcaCAAATTGTTCTCACCCAGTCTCCAGCCATCATGTCTGCATCTCCAGGGGAGAAGGTCAC
CATAACCTGCAGTGCCACCTCAAGTGTAAGTTACATACACTGGTTCCAGCAGAAGCCAGGCAC
TTCTCCCAAACTCTGGATTTATAGCACATCCAACCTGGCTTCTGGAGTCCCTGTTCGCTTCAGT
GGCAGTGGATCTGGGACCTCTTACTCTCTCACAATCAGCCGAATGGAGGCTGAAGATGCTGCC
ACTTATTACTGCCAGCAAAGGAGTAGTTACCCACCCACGTTCGGAGGGGGGACCAAGCTGGA AATAAAACGGGCAGATGCTGCACCAACTGTATCCATCTTCCCACCATCCAGTGAGCAGTTAAC
ATCTGGAGGTGCCTCAGTCGTGTGCTTCTTGAACAACTTCTACCCCAAAGACATCAATGTCAAG
TGGAAGATTGATGGCAGTGAACGACAAAATGGCGTCCTGAACAGTTGGACTGATCAGGACAGC
AAAGACAGCACCTACAGCATGAGCAGCACCCTCACGTTGACCAAGGACGAGTATGAACGACAT
AACAGCTATACCTGTGAGGCCACTCACAAGACATCAACTTCACCCATTGTCAAGAGCTTCAACA
GGAATGAGTGTTAG (SEQ ID NO: 1)

MATGSRTSLLLAFGLLCLPWLQEGSAQIQLVQSGPELKKPGETVKISCKASGYPFTNYGMNWVKQA
PGKGLKWMGWINTYTGEPACADDFRGRFAISLETSARTAYLQINNLINEDTATYFCARTGGGRYNY
GMDYWGQGTSVTVSSAKTTPPSVYPLAPGSAAQTNSMVTLGCLVKGYFPEPVTVTWNSGSLSSG
VHTFPAVLQSDLYTLSSSVTVPSSTWPSETVTCNVAHPASSTKVDKKIVPRDCGCKPCICTVPEVS
SVFIFPPKPKDVLTITLTPKVTCVVVDISKDDPEVQFSWFVDDVEVHTAQTQPREEQFNSTFRSVSE
LPIMHQDWLNGKEFKCRVNSAAFPAPIEKTISKTKGRPKAPQVYTIPPPKEQMAKDKVSLTCMITDF
FPEDITVEWQWNGQPAENYKNTQPIMDTDGSYFVYSKLNVQKSNWEAGNTFTCSVLHEGLHNHH
TEKSLSHSPGKRKRRSGSGAPVKQTLNFDLLKLAGDVESNPGPMATGSRTSLLLAFGLLCLPWLQ
EGSAQIVLTQSPAIMSASPGEKVTITCSATSSVSYIHWFQQKPGTSPKLWIYSTSNLASGVPVRFSG
SGSGTSYSLTISRMEAEDAATYYCQQRSSYPPTFGGGTKLEIKRADAAPTVSIFPPSSEQLTSGGA
SVVCFLNNFYPKDINVKWKIDGSERQNGVLNSWTQDSKDSTYSMSSTLTLTKDEYERHNSYTCE
ATHKTSTSPIVKSFNRNEC (SEQ ID NO: 2)

MATGSRTSLLLAFGLLCLPWLQEGSAQIQLVQSGPELKKPGETVKISCKASGYPFTNYGMNWVKQA
PGKGLKWMGWINTYTGEPACADDFRGRFAISLETSARTAYLQINNLINEDTATYFCARTGGGRYNY
GMDYWGQGTSVTVSS (SEQ ID NO: 17)

CHOTHIA AND KABAT REGIONS INDICATED SEPARATLY. AREAS COVERED BY EITHER METHOD ARE INDICATED IN DOUBLE UNDERLINING

| | |
|---|---|
| CHOTHIA: GYPFTNY = CDR-H1 | (SEQ ID NO: 18) |
| KABAT: NYGMN = CDR-H1 | (SEQ ID NO: 19) |
| CHOTHIA: NTYTGE = CDR-H2 | (SEQ ID NO: 20) |
| KABAT: WINTYTGEPACADDFRG = CDR-H2 | (SEQ ID NO: 21) |
| CHOTHIA: TGGGRYNYGMDY = CDR-H3 | (SEQ ID NO: 22) |

Fig. 9 Cont.

KABAT: TGGGRYNYGMDY = CDR-H3          (SEQ ID NO: 23)

MATGSRTSLLLAFGLLCLPWLQEGSAQIVLTQSPAIMSASPGEKVTITCSATSSVSYIHWFQQKPGT
SPKLWIYSTSNLASGVPVRFSGSGSGTSYSLTISRMEAEDAATYYCQQRSSYPPTFGGGTKLEIKR
ADAAPTVSIFPPSSEQLTSGGASVVCFLNNFYPKDINVKWKIDGSERQNGVLNSWTDQDSKDSTYS
MSSTLTLTKDEYERHNSYTCEATHKTSTSPIVKSFNRNEC      (SEQ ID NO: 24)

CHOTHIA AND KABAT REGIONS THE SAME

SATSSVSYIH = CDR-L1                 (SEQ ID NO: 25)

STSNLAS = CDR-L2                    (SEQ ID NO: 26)

QQRSSYPPT = CDR-L3                 (SEQ ID NO: 27)

SMI41 sequence in AAV:

Signal peptide    variable region    F2Aopt peptide atggcgacgggttcaagaacttccctacttcttgcatttggcctgctttgtttgccgtggttacaggagggctcggcaCAAGTTACTCTAA
AAGAGTCTGGCCCTGGGATATTGAGGCCCTCACAGACCCTCGATCTGACTTGTTCTTTCTCTG
GGTTTTCACTGAGCACTTCTGGTCTGAGTGTAGGCTGGATTCGTCAGCCTTCAGGGAAGGGTC
TGGAGTGGCTGGCACACATTTGGTGGGATGATGTGAAGTACTTTAACCCATCCCTGAAGAGCA
GACTCACAATCTCCAAGGATAGCTCCAGAAACCAGGTgTTCCTCAAGATCACCAGTGTGGACA
CTGCAGATAGTGCCACATACCACTGTACTCGAGGACCTCTGGGTCACGGATTTGACTACTGGG
GCCAAGGGACTCTGGTCACTGTCTCTGCCGCTAAAACGACACCCCCATCTGTCTATCCACTGG
CCCCTGGATCTGCTGCCCAAACTAACTCCATGGTGACCCTGGGATGCCTGGTCAAGGGCTATT
TCCCTGAGCCAGTGACAGTGACCTGGAACTCTGGATCCCTGTCCAGCGGTGTGCACACCTTC
CCAGCTGTCCTGCAGTCTGACCTCTACACTCTGAGCAGCTCAGTGACTGTCCCCTCCAGCACC
TGGCCCAGCGAGACCGTCACCTGCAACGTTGCCCACCCGGCCAGCAGCACCAAGGTGGACA
AGAAAATTGTGCCCAGGGATTGTGGTTGTAAGCCTTGCATATGTACAGTCCCAGAAGTATCATC
TGTCTTCATCTTCCCCCCAAAGCCCAAGGATGTGCTCACCATTACTCTGACTCCTAAGGTCACG
TGTGTTGTGGTAGACATCAGCAAGGATGATCCCGAGGTCCAGTTCAGCTGGTTTGTAGATGAT
GTGGAGGTGCACACAGCTCAGACGCAACCCCGGGAGGAGCAGTTCAACAGCACTTTCCGCTC
AGTCAGTGAACTTCCCATCATGCACCAGGACTGGCTCAATGGCAAGGAGTTCAAATGCAGGGT
CAACAGTGCAGCTTTCCCTGCCCCCATCGAGAAAACCATCTCCAAAACCAAAGGCAGACCGAA
GGCTCCGCAGGTGTACACCATTCCACCTCCCAAGGAGCAGATGGCCAAGGATAAAGTCAGTC
TGACCTGCATGATAACAGACTTCTTCCCTGAAGACATTACTGTGGAGTGGCAGTGGAATGGGC
AGCCAGCGGAGAACTACAAGAACACTCAGCCCATCATGGACACAGATGGCTCTTACTTCGTCT
ACAGCAAGCTCAATGTGCAGAAGAGCAACTGGGAGGCAGGAAATACTTTCACCTGCTCTGTGT
TACATGAGGGCCTGCACAACCACCATACTGAGAAGAGCCTCTCCCACTCTCCTGGTAAA*cgaaa*
*aagaagatcaggttcgggtgcgccagtaaagcagacattaaactttgatttgctgaaacttgcaggtgatgtagagtcaaatcca*
*ggtcca*atggcaacagggagccgaacctctctgctccttgctttcgggctcctttgcctaccgtggctccaagagggctcggcaGATGT
TGTGATGACCCAAACTCCACTCTCCCTGCCTGTCAGTCTTGGAGATCAAGCCTTCATCTCTTGC
AGATCTAGTCAGAGCCTTGTACACAGTGATGGAAACAGCTACTTACATTGGTACCTGCAGAAG
CCAGGCCAGTCTCCAAAGCTCCTGATCTACAAAGTTTCCAACCGATTTTCTGGGGTCCCAGAC
AGGTTCAGTGGCAGTGGATCAGGGACAGATTTCACACTCAAGATCAGCAGAGTGGAGGCTGA
GGATCTGGGACTTTATTTCTGCTCTCAAACTACACATGTTCCTTGGACGTTCGGTGGAGGCAC CAAGCTGGAAATCAAACGGGCAGATGCTGCACCAACTGTATCCATCTTCCCACCATCCAGTGA
GCAGTTAACATCTGGAGGTGCCTCAGTCGTGTGCTTCTTGAACAACTTCTACCCCAAAGACATC
AATGTCAAGTGGAAGATTGATGGCAGTGAACGACAAAATGGCGTCCTGAACAGTTGGACTGAT
CAGGACAGCAAAGACAGCACCTACAGCATGAGCAGCACCCTCACGTTGACCAAGGACGAGTA
TGAACGACATAACAGCTATACCTGTGAGGCCACTCACAAGACATCAACTTCACCCATTGTCAAG
AGCTTCAACAGGAATGAGTGTTAG (SEQ ID NO: 3)

MATGSRTSLLLAFGLLCLPWLQEGSAQVTLKESGPGILRPSQTLDLTCSFSGFSLSTSGLSVGWIRQ
PSGKGLEWLAHIWWDDVKYFNPSLKSRLTISKDSSRNQVFLKITSVDTADSATYHCTRGPLGHGFD
YWGQGTLVTVSAAKTTPPSVYPLAPGSAAQTNSMVTLGCLVKGYFPEPVTVTWNSGSLSSGVHTF
PAVLQSDLYTLSSSVTVPSSTWPSETVTCNVAHPASSTKVDKKIVPRDCGCKPCICTVPEVSSVFIF
PPKPKDVLTITLTPKVTCVVVDISKDDPEVQFSWFVDDVEVHTAQTQPREEQFNSTFRSVSELPIMH
QDWLNGKEFKCRVNSAAFPAPIEKTISKTKGRPKAPQVYTIPPPKEQMAKDKVSLTCMITDFFPEDI
TVEWQWNGQPAENYKNTQPIMDTDGSYFVYSKLNVQKSNWEAGNTFTCSVLHEGLHNHHTEKSL
SHSPGK*RKRRSGSGAPVKQTLNFDLLKLAGDVESNPGP*MATGSRTSLLLAFGLLCLPWLQEGSA
DVVMTQTPLSLPVSLGDQAFISCRSSQSLVHSDGNSYLHWYLQKPGQSPKLLIYKVSNRFSGVPD
RFSGSGSGTDFTLKISRVEAEDLGLYFCSQTTHVPWTFGGGTKLEIKRADAAPTVSIFPPSSEQLTS
GGASVVCFLNNFYPKDINVKWKIDGSERQNGVLNSWTQDSKDSTYSMSSTLTLTKDEYERHNSY
TCEATHKTSTSPIVKSFNRNEC (SEQ ID NO: 4)

MATGSRTSLLLAFGLLCLPWLQEGSAQVTLKESGPGILRPSQTLDLTCSFSGFSLSTSGLSVGWIR
QPSGKGLEWLAHIWWDDVKYFNPSLKSRLTISKDSSRNQVFLKITSVDTADSATYHCTRGPLGH
GFDYWGQGTLVTVSA (SEQ ID NO: 28)

Fig. 10 cont.

CHOTHIA AND KABAT REGIONS INDICATED SEPARATLY. AREAS COVERED BY EITHER METHOD ARE INDICATED IN DOUBLE UNDERLINING

CHOTHIA: GFSLSTSGL = CDR-H1 (SEQ ID NO: 29)

KABAT: TSGLSVG = CDR-H1 (SEQ ID NO: 30)

CHOTHIA: WWDDV = CDR-H2 (SEQ ID NO: 31)

KABAT: HIWWDDVKYPNPSLKS = CDR-H2 (SEQ ID NO: 32)

CHOTHIA: GPLGHGFDY = CDR-H3 (SEQ ID NO: 33)

KABAT: GPLGHGFDY = CDR-H3 (SEQ ID NO: 34)

MATGSRTSLLLAFGLLCLPWLQEGSADVVMTQTPLSLPVSLGDQAFISCRSSQSLVHSDGNSYLHWYLQKPGQSPKLLIYKVSNRFSGVPDRFSGSGSGTDFTLKISRVEAEDLGLYFCSQTTHVPWTFGGGTKLEIKR (SEQ ID NO: 35)

CHOTHIA AND KABAT REGIONS THE SAME

RSSQSLVHSDGNSYLH = CDR-L1 (SEQ ID NO: 36)

KVSNRFS = CDR-L2 (SEQ ID NO: 37)

SQTTHVPWT = CDR-L3 (SEQ ID NO: 38)

H6-3C4. Human anti-human mrtCD52--Light chain variable region tcttctgaactgactcaggaccctgttgtgtct
 S   S   E   L   T   Q   D   P   V   V   S
gtggccttgggacagacagtcaggatcacatgccaaggagacagcctcagaacctatcat
 V   A   L   G   Q   T   V   R   I   T   C   Q   G   D   S   L   R   T   Y   H
gcaagctggtaccagcagaagccaagacaggcccctgtacttgtcatctatgatgaaaac
 A   S   W   Y   Q   Q   K   P   R   Q   A   P   V   L   V   I   Y   D   E   N
aaccggccctcagggatcccagaccgattctctggctccacctcaggaaacacagcttcc
 N   R   P   S   G   I   P   D   R   F   S   G   S   T   S   G   N   T   A   S
ttgaccatcactggggctcaggcggaagatgaggctgactattactgtaactcccgggac
 L   T   I   T   G   A   Q   A   E   D   E   A   D   Y   Y   C   N   S   R   D
Agcagtggtaaccgtctggtattcggcggagggaccaagctgaccgtccta (SEQ ID NO: 5)
 S   S   G   N   R   L   V   F   G   G   T   K   L   T   V   L   (SEQ ID NO: 6)

Heavy chain Variable region caggtgcagctacagcagtggggcgcaggactgttgaagccttcggagaccctg
 Q   V   Q   L   Q   Q   W   G   A   G   L   L   K   P   S   E   T   L
tccctcacttgcgatgtctatggtgggtccttcagtggttactactggagttggatccgc
 S   L   T   C   D   V   Y   G   G   S   F   S   G   Y   Y   W   S   W   I   R
cagcccccaggaagggggctggagtggattggggaaatcaatcatagtggaagcaccaac
 Q   P   P   G   K   G   L   E   W   I   G   E   I   N   H   S   G   S   T   N
tacaacccgtccctcaggagtcgagtcaccatatcagtagacacgtccaagaatcagttc
 Y   N   P   S   L   R   S   R   V   T   I   S   V   D   T   S   K   N   Q   F
tccctgaagctgaggtctgtgaccgccgcggacacggctgtgtattactgtgcgagaggc
 S   L   K   L   R   S   V   T   A   A   D   T   A   V   Y   Y   C   A   R   G
tttatggttcggggaattatgtggaactactacatggacgtctggggcaaagggacc
 F   M   V   R   G   I   M   W   N   Y   Y   M   D   V   W   G   K   G   T
acggtcaccgtctcccca (SEQ ID NO: 7)
 T   V   T   V   S   P   (SEQ ID NO: 8)

CHOTHIA AND KABAT REGIONS INDICATED SEPARATLY. AREAS COVERED BY EITHER METHOD ARE INDICATED IN DOUBLE UNDERLINING

CHOTHIA: GGSFSGY = CDR-H1 (SEQ ID NO: 39)

KABAT: GYYWS = CDR-H1 (SEQ ID NO: 40)

CHOTHIA: NHSGS = CDR-H2 (SEQ ID NO: 41)

KABAT: EINHSGSTNYNPSLRS = CDR-H2 (SEQ ID NO: 42)

CHOTHIA: GFMVRGIMWNYYYMDV = CDR-H3 (SEQ ID NO: 43)

KABAT: GFMVRGIMWNYYYMDV = CDR-H3 (SEQ ID NO: 44)

H3.1 Mouse anti human-ZP3---Heavy chain variable region
cagatccagttggtgcagtctggacctgaggtgaagaagcctggagagacagtcaagatc
 Q  I  Q  L  V  Q  S  G  P  E  V  K  K  P  G  E  T  V  K  I
tcctgcaaggcttctggttataagttcacagactattcaattcactgggtgaagcaggtt
 S  C  K  A  S  G  Y  K  F  T  D  Y  S  I  H  W  V  K  Q  V
ccaggaaagggtttaaagtggatgggctggatagacactgagactggtgagtcaacatat
 P  G  K  G  L  K  W  M  G  W  I  D  T  E  T  G  E  S  T  Y
gcagatgacttcaggggacggttttgacttctctttggaaacttctgtcagcactgcctct
 A  D  D  F  R  G  R  F  D  F  S  L  E  T  S  V  S  T  A  S
ttggagatcaacaacctcaaaaatgacgacacgactacatattttgtgctagatggga
 L  E  I  N  N  L  K  N  D  D  T  T  Y  F  C  A  R  W  G
Tcgggccttgcttattggggccaagggactctggtcactgtctctgca (SEQ ID NO: 9)
 S  G  L  A  Y  W  G  Q  G  T  L  V  T  V  S  A  (SEQ ID NO: 10)

CHOTHIA AND KABAT REGIONS INDICATED SEPARATLY. AREAS COVERED BY EITHER METHOD ARE INDICATED IN DOUBLE UNDERLINING

CHOTHIA: GYKFTDY = CDR-H1           (SEQ ID NO: 45)
    KABAT: DYSIH = CDR-H1               (SEQ ID NO: 46)
    CHOTHIA: DTETGE = CDR-H2            (SEQ ID NO: 47)
    KABAT: WIDTETGESTYADDFRG = CDR-H2   (SEQ ID NO: 48)
    CHOTHIA: WGSGLAY = CDR-H3           (SEQ ID NO: 49)
    KABAT: WGSGLAY = CDR-H3             (SEQ ID NO: 50)

H3.1 Light chain Variable region
gatgctgtgctgacccagactccactcactttgtcggttaccagtggacaaccagcctcc
 D  A  V  L  T  Q  T  P  L  T  L  S  V  T  S  G  Q  P  A  S
atctcttgcaagtcaagtcagagcctcttagatagtgatggaaagacatatttgagttgg

```
I  S  C  K  S  S  Q  S  L  L  D  S  D  G  K  T  Y  L  S  W
ttgttacagaggccaggccagtctccaaagtgcctgatctatctggtgtctaaactggac
 L  L  Q  R  P  G  Q  S  P  K  C  L  I  Y  L  V  S  K  L  D
tctggagtccctgacaggttcactggcagtggatcagggacagatttcacactgaaaatc
 S  G  V  P  D  R  F  T  G  S  G  S  G  T  D  F  T  L  K  I
aacagagtggaggctgaggatttggagtttattgttgctggcaaggaacacacttgtgc
 N  R  V  E  A  E  D  L  G  V  Y  C  C  W  Q  G  T  H  L  C
accttcggagggggaccaagctggagataaaacgg (SEQ ID NO: 11)
 T  F  G  G  G  T  K  L  E  I  K  R  (SEQ ID NO: 12)
```

CHOTHIA AND KABAT REGIONS THE SAME

KSSQSLLDSDGKTYLS = CDR-L1          (SEQ ID NO: 51)

LVSKLDS = CDR-L2                   (SEQ ID NO: 52)

WQGTHLCT = CDR-L3                  (SEQ ID NO: 53)

E12 anti-hcg heavy chain

QVQLQQSGGGLVKPGGSLKLSCAASGFTFSSYGMSWVRQTPEKRL

EWVATSIGGGSYTYAAYPDSVKGRFTISRDNAKNNLYLQMSSLRSE

DTALFYCVRLYGTSPWFDYWGQG (SEQ ID NO: 13)

```
caggugcagcugcagcagucoggcggcggccugguqaagcccggcggcucccugaagcugu
ccugcgccgccuccggcuucaccuucuccucuacggcaugucoggguqcggcagacocc
cgagaagcggcuggaguggguggccaccuccaucggcggcggcuccuacaccuacgccgcc
uacccogacuccgugaagggccgguucaccaucuccogggacaacgccaagaacaaccugu
accugcagaugucoucocugcgguccgaggacaccgcccuguucuacugcgugcggcugua
cggcaccuccocccugguucgacuacuggggccagggc        (SEQ ID NO: 54)
```

```
caggtgcagctgcagcagtccggcggcggcctggtgaagcccggcggctccctgaagctg
 Q   V   Q   L   Q   Q   S   G   G   G   L   V   K   P   G   G   S   L   K   L
tcctgcgccgcctccggcttcaccttctcctcctacggcatgtcctgggtgcggcagacc
 S   C   A   A   S   G   F   T   F   S   S   Y   G   M   S   W   V   R   Q   T
cccgagaagcggctggagtgggtggccacctccatcggcggcggctcctacacctacgcc
 P   E   K   R   L   E   W   V   A   T   S   I   G   G   G   S   Y   T   Y   A
gcctacccgactccgtgaagggccggttcaccatctcccgggacaacgccaagaacaac
 A   Y   P   D   S   V   K   G   R   F   T   I   S   R   D   N   A   K   N   N
ctgtacctgcagatgtcctcctgcggtccgaggacaccgccctgttctactgcgtgcgg
 L   Y   L   Q   M   S   S   L   R   S   E   D   T   A   L   F   Y   C   V   R
ctgtacggcacctcccctggttcgactactggggccagggc (SEQ ID NO: 55)
 L   Y   G   T   S   P   W   F   D   Y   W   G   Q   G   (SEQ ID NO: 13)
```

CHOTHIA AND KABAT REGIONS INDICATED SEPARATLY. AREAS COVERED BY EITHER METHOD ARE INDICATED IN DOUBLE UNDERLINING

| | |
|---|---|
| CHOTHIA: GFTFSSY = CDR-H1 | (SEQ ID NO: 56) |
| KABAT: SYGMS = CDR-H1 | (SEQ ID NO: 57) |
| CHOTHIA: IGGGSYTY = CDR-H2 | (SEQ ID NO: 58) |
| KABAT: TSIGGGSYTYAAYPDSVKG = CDR-H2 | (SEQ ID NO: 59) |
| CHOTHIA: LYGTSPWFDY = CDR-H3 | (SEQ ID NO: 60) |
| KABAT: LYGTSPWFDY = CDR-H3 | (SEQ ID NO: 61) |

E12 anti-hcg light chain

DIQMTQSPAILSVSPGERVSFSCRASQSIGTSIHWYQQRTNGSPRLLI

AAAYSASESYAPSRFSGSRSGTDATLSINSVESEDIADYYCQQSNSW

PLTFGAGTKLEIKR (SEQ ID NO: 14)

```
gacaucccagaugacccaguccccggccauccugucccguguccccggcgagcggguguccc
uucuccugccgggccucccaguccaucggcaccuccauccacugguaccagcagcggacc
aacggcuccccccggcugcugaucgccgccgccuacuccgccuccgaguccuacgccccc
uccccgguucuccggcucccggucccggcaccgacgccacccugucccaucaacuccgugag
uccgaggacaucgccgacuacuacugccagcaguccaacuccuggccccugaccuucggc
gccggcaccaagcuggagaucaagcgg       (SEQ ID NO: 62)
```

```
gacatccagatgacccagtccccgccatcctgtccgtgtccccggcgagcgggtgtcc
 D   I   Q   M   T   Q   S   P   A   I   L   S   V   S   P   G   E   R   V   S
ttctcctgccgggcctcccagtccatcggcacctccatcactggtaccagcagcggacc
 F   S   C   R A S Q S I G T S I H   W   Y   Q   R   T
aacggctcccccggctgctgatcgccgccgcctactccgcctccgagtcctacgcccc
 N   G   S   P   R   L   L   I   A A Y S A S E S   Y   A   P
tcccggttctccggctcccggtccggcaccgacgccaccctgtccatcaactccgtggag
 S   R   F   S   G   S   R   S   G   T   D   A   T   L   S   I   N   S   V   E
tccgaggacatcgccgactactactgccagcagtccaactcctggcccctgaccttcggc
 S   E   D   I   A   D   Y   Y   C   Q Q S N S W P L T   F   G
gccggcaccaagctggagatcaagcgg      (SEQ ID NO: 63)
 A   G   T   K   L   E   I   K   R      (SEQ ID NO: 14)
```

CHOTHIA AND KABAT ARE THE SAME

RASQSIGTSIH = CDR-L1        (SEQ ID NO: 64)

AAYSASES = CDR-L2        (SEQ ID NO: 65)

QQSNSWPLT = CDR-L3        (SEQ ID NO: 66)

ANTIBODY-MEDIATED IMMUNOCONTRACEPTION

STATEMENT REGARDING FEDERALLY SPONSORED R&D

This invention was made with government support under Grant No. OD003878 awarded by the National Institutes of Health. The government has certain rights in the invention.

REFERENCE TO SEQUENCE LISTING

The present application is filed along with a Sequence Listing in electronic format. The Sequence Listing is provided as a file entitled CALTE093.txt, created Jan. 30, 2014, which is 42,548 bytes in size. The information in the electronic format of the Sequence Listing is incorporated herein by reference in its entirety.

BACKGROUND

Field

The present disclosure generally relates to methods and compositions for contraception and manipulation or other reproduction-associated traits. In some embodiments, vector based approaches for contraception are provided.

Description of the Related Art

Currently, one approach to achieving control over reproduction and sex-related behaviors is though surgery. Several alternative methods include the use of drugs that mimic or antagonize reproductive hormones, or injection of chemicals directly into the testes that destroy reproductive tissues.

In some situations, groups have used vaccinations with specific antigens to induce expression of antibodies that inhibit the function of specific proteins. Animals and humans can be vaccinated so as to induce the creation of antibodies that bind to, and neutralize or destroy proteins or pathogens foreign to the body. Animals can also be vaccinated so as to generate antibodies that bind to proteins normally present in the body (self antigens), though the responses mounted are often attenuated and transient as compared with those mounted to non-self antigens. Of specific importance for the discussion below, it has been known that vaccination of humans and other animals against specific self antigens or complex mixtures of self antigens (i.e. whole sperm) can bring about infertility (though usually only transient infertility, reviewed in (Gupta, S. K. and Bansal, P. 2010 *Reprod Med Biol* 9: 61-71; Kirkpatrick, J. F. et al. 2011 *Am J Reprod Immunol* 66: 40-50; McLaughlin, E. A. and Aitken, R. J. 2011 *Molecular and cellular endocrinology* 335: 78-88; Gupta et al. Human Vaccines and immunotherapeutics 10: 4, 1-15) Where examined, these effects are thought (with a few exceptions in which antibody or T-cell mediated toxicity is involved) to result from the induction of antibodies that neutralize the function of the relevant protein through simple binding. These observations show that in vivo antibody titers induced through vaccination can be sufficient to inhibit fertility on a very limited basis. However, to date, this has not become a useful means of contraception, perhaps in part, due to the fact that, as noted above, the responses are often attenuated and transient.

SUMMARY

In some embodiments, a recombinant genetic construct is provided. The construct can comprise an antibody gene that encodes an antibody or a fragment thereof that binds to a protein, a peptide, or a small molecule specific to reproductive function. The genetic construct can be configured to be delivered and expressed in an animal subject.

In some embodiments, a contraceptive composition is provided that can comprise the genetic construct described above or described herein.

In some embodiments, a contraceptive composition is provide that is configured to be delivered to an animal through intramuscular injection, subcutaneous injection, intravenous injection, intraperitoneal injection, oral delivery, electroporation through the skin, sonication, or nasal inhalation.

In some embodiments, a method of contraception in an animal is provided. The method can comprise administering to the animal a genetic construct described above or herein.

In some embodiments, a pharmaceutical composition is provided. It can comprise the genetic construct described above or herein and a pharmaceutically acceptable carrier. The genetic construct can be present in at least 1 ug/ml. The pharmaceutically acceptable carrier can be combined with a nucleic acid.

BRIEF DESCRIPTION OF THE DRAWINGS

FIG. 9 depicts the nucleic acid and amino acid sequences of HB9094 in AAV (signal peptide sequence is highlighted, variable region is underlined, F2Aopt peptide (self-cleaving) is in bold and italics.

FIG. 10 depicts the nucleic acid and amino acid sequences of SMI41 in AAV (signal peptide sequence is highlighted, variable region is underlined, F2Aopt peptide (self-cleaving) is in bold and italics.

FIG. 11 depicts the amino acid and nucleic acid sequence of a human anti-human mrtCD52 antibody (heavy and light chains), which can be used in some embodiments provided herein.

FIG. 12 depicts the amino acid and nucleic acid sequence of aH3.1 mouse anti-human-ZP3 antibody (heavy and light chains), which can be used in some embodiments provided herein.

FIG. 13 depicts the amino acid sequences of the heavy and light chain antibody E12, an anti-human chorionic gonadotropin antibody, which can be used in some embodiments provided herein.

DETAILED DESCRIPTION

Figure 1A:
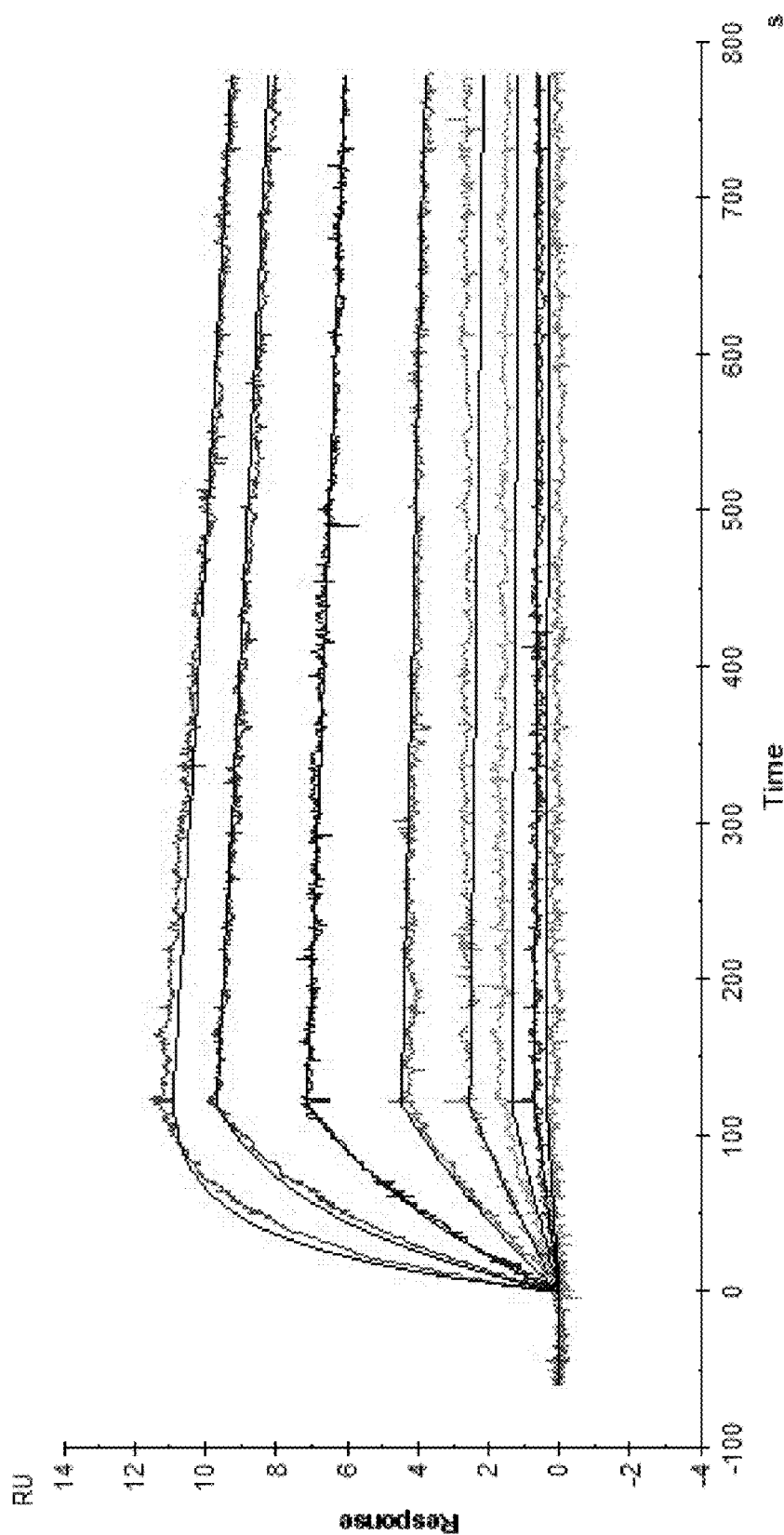
FIGS. 1A and 1B depict the binding affinity of HB9094-HEK293T-IgG. Surface plasmon resonance binding data for cloned antibody expressed in HEK 293T cells (A), and original monoclonal antibody (B).

There are a number of contexts in which it would be useful to be able to induce effectively permanent or long term but reversible sterility in various organisms. These include, for example, the vast numbers of feral cats and dogs in the USA and other countries, feral pigs, wild horses, burros, deer, elephants, red foxes and other invasive species (Kirkpatrick, J. F. et al. 2011 *Am J Reprod Immunol* 66: 40-50; Munks, M. W. 2012 *Reproduction in Domestic Animals* 47 (Suppl 4): 223-227; Pickard, A. R. and Holt, W. V. 2007 *Royal College of Obstetricians & Gynaecologists* 33: 48-52). In addition, sterilization through disruption of reproductive hormone function is also used for behavior modification of livestock (Price, E. O. et al. 2003 *Journal of animal science* 81: 411-415), to prevent boar taint in pigs (Batorek et al., 2012), and pregnancy in cattle being prepared for slaughter (Geary, T. W. et al. 2006 *Journal of animal science* 84: 343-350). Long-term, non-surgical suppression of fertility is also desired for a number of other organisms, including humans. Thus, long term manipulation of the functions of molecules involved in reproduction have several useful applications.

Current methods of contraception either involve surgery, which generally provides permanent sterilization, or are not permanent (are not effectively permanent), have significant failure rates and/or side effects, or are only applicable to one sex (Kutzler, M. and Wood, A. 2006 *Theriogenology* 66: 514-525; *Contraceptive Technology*, Edited by Robert A. hatcher, James Trussell and Anita L. Nelson. PDR Network, 19th edition, 2008)

Immunocontraception can be a desirable alternative to surgery and other contraceptive technologies, assuming various barriers can be overcome. In immunocontraception the animal is vaccinated with the protein, peptide or small molecule whose activity is required for reproduction. If antibodies that bind the target are generated, this can result in inability to reproduce (Kirkpatrick, J. F. et al. 2011 *Am J Reprod Immunol* 66: 40-50; Munks, M. W. 2012 *Reproduction in Domestic Animals* 47 (Suppl 4): 223-227). The vaccine may include an adjuvant of some sort designed to stimulate an immune response. In many cases the protein or peptide is also conjugated to other proteins or small molecules, also with the hope of stimulating an immune response to the target molecule. A difficulty in implementing this approach is that one is trying to induce an immune response to a self-antigen, and endogenous protein. The immune system is designed to make this difficult, thereby preventing autoimmune disease.

Vaccination against gonadotropin releasing hormone (GnRH), also known as leuteinizing hormone releasing hormone (LHRH) can inhibit reproduction in both sexes (Fraser, H. M. and Baker, T. G. 1978 *The Journal of endocrinology* 77: 85-93; Fraser, H. M. et al. 1974 *The Journal of endocrinology* 63: 399-406; Fraser, H. M. 1975 *The Journal of endocrinology* 64: 191-192). Inhibiting GnRH function prevents the release of downstream target hormones leutinizing hormone (LH) and follicle stimulating hormone (FSH), which are required for the development and maintenance of both male and female gonads. Vaccination against components of the zona pellucida, a glycoprotein matrix that surrounds the egg, can also result in female sterility (Yanagimachi, R. et al. 1976 *Proc Natl Acad Sci USA* 73: 2405-2408; Barfield, J. P. et al. 2006 *Contraception* 73: 6-22; Gupta, S. K. and Bansal, P. 2010 *Reprod Med Biol* 9: 61-71; Gupta, S. K. et al. 2011 *Journal of reproductive immunology* 88: 240-246; Kirkpatrick, J. F. et al. 2009 *Journal of reproductive immunology* 83: 151-157; East, I. J. et al. 1985 *Dev Biol* 109: 268-273; East, I. J. et al. 1984 *Dev Biol* 104: 49-56). A number of other proteins have also been considered as possible candidates for immunocontraception. For some there is good evidence that antibodies targeted to the relevant protein have contraceptive effect (Naz, R. K. et al. 2005 *Hum Reprod* 20: 3271-3283; Gupta et al. Human Vaccines and immunotherapeutics 10: 4, 1-15). Thus, for a short period of time, antibodies can be induced that appear to be able to neutralize function of molecules essential for reproduction, and these are sufficient to inhibit reproduction. Adjuvants that enhance the efficacy of such vaccines have been described (see, e.g., U.S. Pat. No. 7,731,939, the entirety of which is hereby incorporated by reference).

The problems encountered with current implementations of immunocontraception are that 1) multiple injections are often needed to induce a strong enough immune response, and 2) the effects of immunization decrease over time, requiring booster injections at species-specific intervals. Both of these problems likely relate to the fact that, in most cases (the exception discussed further below being anti-sperm antibodies present in females), the immune system is being asked to mount an immune response to an endogenous molecule, present throughout the lifetime of the animal.

Furthermore, current approaches to immunocontraception in large populations suffer from several fatal flaws. The immune response to vaccination varies on an individual-to-individual basis. Some individuals never mount a strong response, and therefore never become infertile. Often multiple boosts are needed to achieve adequate antibody titers. Thus there can be a long time lag lasting 3 months or longer between vaccination and achievement of antibody titers necessary for infertility. In addition, the antibody response usually decreases after some time, resulting in restoration of fertility. However, there is no way of predicting if or when this will occur. Finally, vaccination can result in unwanted immune responses that lead to tissue damage, anaphylactic shock or autoimmune disease. In short, the outcome of active immunization is inherently unpredictable, making it of limited utility in many species, including humans (reviewed in Cooper, D. W. and Larsen, E. 2006 *Reproduction* 132: 821-828; Kirkpatrick, J. F. et al. 2011 *Am J Reprod Immunol* 66: 40-50; McLaughlin, E. A. and Aitken, R. J. 2011 *Molecular and cellular endocrinology* 335: 78-88; Gupta et al. *Human Vaccines and immunotherapeutics* 10: 4, 1-15).

Provided herein is a new approach to immunocontraception that, in some embodiments, bypasses the need to induce an immune response in each individual in which fertility and/or fertility-associated traits (such as behavior or carcass quality) are to be modified. The method utilizes transgene-dependent expression of recombinant antibodies known to induce infertility. In addition, in some embodiments, methods of reversing contraception achieved in this way are also outlined.

Some embodiments provided herein provide tools and methods for bringing about transient or long-term contraception in any vertebrate. Genes that encode antibodies that bind reproductive hormones, components of the egg coat, or of sperm, can be utilized. In some embodiments, the encoded proteins are altered so as to enhance or silence antibody effector functions or alter their localization within the body. The genes are introduced into an expression cassette, and introduced into mitotic or post mitotic cells of the target species such as liver or skeletal muscle, respectively, through one of a number of possible mechanisms. In some embodiments, antibody expression induced in the animal disrupts the function of the targeted molecule. In some embodiments, this blocks reproduction. In some embodiments this alters undesirable sex-specific adult behaviors such as aggression and territoriality (due to loss of testosterone in males and loss of estrogen in females), or results in desirable changes to carcass quality. For example, immunocontraception is used to increase the quality of meat in several ways. A small fraction of male pigs past puberty produce an odor/taste known as boar taint, which is generally considered undesirable. As a result, essentially all adult male pigs are castrated. Immunocontraception can prevent boar taint, by suppressing testosterone production (Dunshea, F. R. et al. 2001 *Journal of Animal Science* 79: 2524-2535). Male goats also produce an undesirable odor, which can be suppressed through vaccination against GnRH, which acts by reducing testosterone, FSH and LH (Godfrey, S. I. et al. 1996 *Animal Reprod.* Sci. 44: 41-54). In the case of male cattle, vaccination against GnRH results in reduced aggressive behavior, a decrease in fat, more meat, and a reduction in the feed:weight gain ratio (Robertson, I. S. et al. 1982 *Vet. Rec* 108: 529-531). Vaccination against GnRH is also used to prevent feedlot pregnancy (Thompson, 2000 *Animal Reproduction Science* 60-61: 459-469) Organisms of interest include pigs (Aluwe et al., 2013 *Meat Science* 94: 402-407; Bonneau et al., 1994 *Journal of Animal Science* 72: 14-20; Meloen et al., 1994 *Vaccine* 12: 741-746) bulls (Amatayakul-Chantler et al., 2013 *Meat Science* 95: 78-84; D'Occhio et al., 2001 *Animal Reproduction Science* 66: 47-58; Price et al., 2003 81: 411-415), as well as sheep and goats (Thompson, 2000 *Animal Reproduction Science* 60-61: 459-469). Antibody-dependent immunocontraception (also known as immunocastration) is also seen in much of Europe as a desirable alternative (from an animal welfare perspective) to castration, which is carried out for all pigs and many cows (Heid and Hamm, 2013 *Meat Science* 95: 203-211).

Some embodiments provided herein utilize cloned genes encoding antibodies with contraceptive activity. In some embodiments, the sequence of such a gene is modified so that the encoded protein is seen as self in the species to be targeted. Alternatively it is generated from the species to be targeted. In some embodiments, the antibody can be modified so as to lack antibody effector activity, and to have a longer half-life in the circulatory system. The modified gene is then cloned into an expression cassette and introduced into postmitotic cells such as skeletal muscle using a number of possible forms of gene delivery. Antibodies expressed in muscle are secreted and enter the circulatory system, where they bind their target molecule, inhibiting its function and thereby suppressing reproduction and in some cases reproductive behaviors.

Definitions

The term "immunocontraception" does not require that 100% of the subjects receiving the treatment have absolutely no chance of reproducing. Instead, unless denoted otherwise, a subject that has received an immunocontraceptive via gene delivery will have a reduced likelihood of reproducing. In some embodiments, this is reduced by 10, 20, 30, 40, 50, 60, 70, 80, 90, 95, 99, 99.9, 99.99, or 100% (with 100% reduction indicating no chance of reproduction). In some embodiments, the percentage reduced is maintained for at least a satisfactory or desired amount of time. In some embodiments, the reduction is maintained for at least 1 month, for example 2, 3, 4, 5, 6, 7, 8, 9, 10, 11, or 12 months. In some embodiments, the reduction is maintained for at least 1 year, for example, 1, 2, 3, 4, 5, 6, 7, 8, 9, 10, 11, 12, 13, 14, 15, 16, 17, 18, 19, 20, 25, 30, 35, 40, 45, 50, 55, or 60 years. In some embodiments, the reduction is measured and/or set as a fraction of the organism's life, for example, 10, 20, 30, 40, 50, 60, 70, 80, 90, or 100% of the organism's life will be at the noted reduction in likelihood of ability to reproduce. In some embodiments, the reduction is measured and/or set as a fraction of the organism's reproductive life, for example, 10, 20, 30, 40, 50, 60, 70, 80, 90, or 100% of the organism's life will be at the noted reduction in likelihood of ability to reproduce. In some embodiments, the contraceptive can be administered in a single dose, no more frequently than once a year. In some embodiments, the contraceptive can be administered in a single dose, no more frequently than once every 2 years. In some embodiments, the contraceptive can be administered in a single dose, no more frequently than once every 3 years. In some embodiments, the contraceptive can be administered in a single dose, no more frequently than once every 4 years. In some embodiments, the contraceptive can be administered in a single dose, no more frequently than once every 5 years. In some embodiments, the contraceptive can be administered in a single dose, no more frequently than once every 6 years. In some embodiments, the contraceptive can be administered in a single dose, no more frequently than once every 7 years. In some embodiments, the contraceptive can be administered in a single dose, no more frequently than once every 8 years. In some embodiments, the contraceptive can be administered in a single dose, no more frequently than once every 9 years. In some embodiments, the contraceptive can be administered in a single dose, no more frequently than once every 10 years.

The term "effectively permanent" denotes that the result to be achieved will be maintained for as long as intended for that particular application. For example, while an organism may live for a set number of years, for example 10 years, the organism's effective reproductive life span may only be half of that time (5 years). Thus, a system that results in contraception for 5 years would be effectively permanent. In some embodiments, the contraception or other process is reversible. Thus, in some embodiments, the system or method is reversibly permanent. As such, the term "permanent" denotes the time span, not the reversibility of the arrangement.

A vector that can be used herein includes, but is not limited to, a viral vector, a plasmid, a RNA vector or a linear or circular DNA or RNA molecule which may include a chromosomal, nonchromosomal, semi-synthetic or synthetic DNA. Some vectors are those capable of autonomous replication (episomal vector) and/or expression of nucleic acids to which they are linked (expression vectors). Large numbers of suitable vectors are known to those of skill in the art and commercially available.

Throughout this disclosure, the term "antibody" (Ab) includes monoclonal antibodies, polyclonal antibodies, multispecific antibodies (for example, bispecific antibodies and polyreactive antibodies), and antibody fragments. Thus, the term "antibody" and "isolated antibody" are used interchangeably herein to refer to an isolated antibody according to embodiments of the present invention. An antibody in any context within this specification is meant to include, but is not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a tight chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from the NH2 terminus to the COOH terminus as follows: FWR1, CDR1, FWR2, CDR2, FWR3, CDR3, FWR4. The variable regions of the heavy and light chains contain a binding domain that interacts with an antigen while, depending on the isotype, the constant region(s) may mediate the binding of the immunoglobulin to host tissues or factors. CDR1, CDR2, and CDR3 of the light chain are referred to as CDRL1, CDRL2 and CDRL3, respectively. CDR1, CDR2, CDR3 of the heavy chain are referred to as CDRH1, CDRH2, and CDRH3, respectively.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan. The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in dose proximity by the FRs and, with the hypervariable regions from the other chain, contribute to the formation of the antigen-binding site of antibodies. The term "hypervariable region" as used herein refers to the amino acid residues of an antibody that are responsible for antigen binding. The hypervariable region generally comprises amino acid residues from a "complementarity determining region" ("CDR").

An antibody of the present invention may be a "humanized antibody". A humanized antibody is considered to be a human antibody that has one or more amino acid residues introduced into it from a source that is non-human. These non-human amino acid residues often are referred to as "import" residues, which typically are taken from an "import" variable region. Humanization may be performed following known methods by substituting import hypervariable region sequences for the corresponding sequences of a human antibody. (See, for example, Jones et al., Nature, 321:522-525 20 (1986); Reichmann et al., Nature, 332:323-327 (1988); Verhoeyen et al., Science, 239:1534-1536 (1988)) the entire contents of each are incorporate herein by reference). Accordingly, such "humanized" antibodies are chimeric antibodies in which substantially less than an intact human variable region has been substituted by the corresponding sequence from a non-human species.

The term antibody includes an "antibody fragment" which includes a portion of an intact antibody, such as the antigen binding or variable region of the intact antibody. Examples of antibody fragments include, but are not limited to, Fab, Fab', F(ab')2, and Fv fragments; diabodies; linear antibodies; single-chain antibody molecules; and multispecific antibodies formed from antibody fragments. (See, for example, U.S. Pat. No. 5,641,870, the entire content of which is incorporated herein by reference).

Vectored Expression of Antibodies

In line with the above, provided herein are methods and compositions that include vectored expression of antibodies. A number of studies have shown that high levels of recombinant antibodies can be expressed in intact animals, for an extended period of time. (Balazs, A. B. et al. 2013 Nat Biotechnol 31: 647-652; Balazs, A. B. et al. 2012 Nature 481: 81-84; Hicks, M. J. et al. 2012 Sci Transl Med 4: 140ra187; Limberis, M. P. et al. 2013 Sci Transl Med 5: 187ra172; Rosenberg, J. B. et al. 2012 Hum Gene Ther 23: 451-459). The above referenced work utilizes AAV as a delivery vector. Antibody-like immunoadhesins have been similarly used (Johnson, P. R. et al. 2009 Nat Med 15: 901-906).

It has now been appreciated that the above AAV delivery vector, as well as other DNA delivery vehicles noted below, can also be used in immunocontraception, via the direct expression of genes encoding antibodies known to inhibit the function of protein essential for reproduction, in the organism of interest. Interestingly, in some embodiments, one or more of the above noted issues with the current state of the art regarding immunocontraception do not apply when the antibody is administered via AAV or other DNA or RNA transgene-based delivery mechanism.

In some embodiments, DNA vectors expressing antibody-encoding nucleic acids can be introduced into a variety of tissues. Examples that involve intramuscular or intravenous injection include expression in skeletal muscle, liver, brain and kidney. Examples using nasal or oral delivery include expression in the respiratory and digestive systems, respectively. Adipose tissue provides another potential site of long-term expression accessible through injection, others include parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

Thus, the immuncontraceptive molecule (e.g., an antibody that stops or reduces the likelihood of pregnancy), can be administered via the vector in any number of ways.

In some embodiments, non-dividing tissues such as muscle and neurons and other nervous system tissue, which have little or no cell turnover, can be used to provide long-term expression. In some embodiments, dividing tissues, such as liver, and others composed of epithelial cells that turn over on a regular basis (respiratory and digestive systems) can be used to provide long-term or more transient expression. Long-term expression can be achieved if DNA vectors integrate into stem cell populations in the above tissues. Long-term expression can also be achieved using episomal vectors that have the ability to replicate in specific cell types (e.g. Wong, S—P and Harbottle, R. P. 2013 Molecular Therapy-Nucleic Acids 2, e115; doi:10.1038/ mtna.2013.40). Alternatively, if the vectors remain episomal and non-replicating, they will be gradually lost as cells in which they are introduced divide. This creates a straightforward mechanism for guaranteeing reversibility.

In some embodiments, implementations are muscle or neurons (long term) and liver, respiratory and digestive systems (shorter term). Thus, by selecting the target organ or tissue type to inject, one can control the length of effectiveness of the immunocontraception. In some embodiments, the method of administration includes injecting the vector into one or more of the above locations. In some embodiments, the composition and mixture to be administered is formulated for injection via or into one of the above locations. In some embodiments DNA to be expressed is packaged into delivery vehicles (including but limited to liposomes, nanoparticles, virus-like particles, phage, complexes with peptides, etc) that preferentially are targeted, and/or taken up by specific cell types.

DNA encoding for the immunocontraceptive molecule can be introduced in a variety of forms. A vector which can be used includes, but is not limited to, a viral vector, a plasmid, a RNA vector or a linear or circular DNA or RNA molecule which may include a chromosomal, nonchromosomal, semi-synthetic or synthetic DNA. Some vectors are those capable of autonomous replication (episomal vector) and/or expression of nucleic acids to which they are linked (expression vectors). Large numbers of suitable vectors are known to those of skill in the art and commercially available.

Implementations noted herein can use AAV-mediated antibody expression. AAV can be useful as a vector because it is taken up by target tissues very efficiently. It also remains primarily episomal, limiting the possibility for unwanted mutagenesis. Genes expressed from AAV can be expressed for long periods of time, and may be resistant to silencing. Also, expression from AAV is often toleragenic. AAV can be used in some embodiments. However, because of viral shedding, pre-existing immunity to AAV in many mammals, and cost of generating sufficient AAV, a number of other possible implementations of interest are noted. These include but are not limited to the use of: an AAV chimera (e.g., AAV2/8), used by many labs, and described in more detail in (Balazs, A. B. et al. 2012 *Nature* 481: 81-84); AAV-like replicative form DNA (Li, L. et al. 2013a *PLoS One* 8: e69879); minicircles (Dong, Y. et al. 2013 *Journal of biotechnology* 166: 84-87; Gracey Maniar, L. E. et al. 2013 *Molecular therapy: the journal of the American Society of Gene Therapy* 21:131-138; Kay, M. A. et al. 2010 *Nat Biotechnol* 28: 1287-1289); linear closed DNA (Nafissi, N. and Slavcev, R. 2012 *Microbial cell factories* 11: 154; Schakowski, F. et al. 2007 In Vivo 21: 17-23); virus like particles (Zeltins, A. 2013 *Molecular biotechnology* 53: 92-107); cell penetrating peptide complexes (Alhakamy, N. A. et al. 2013 *Therapeutic delivery* 4: 741-757); and various other sorts DNA complex-forming mixtures. Mnicircles containing scaffold/matrix attachment regions (S/MAR), which can promote stable replication of many generations in dividing cells such as the liver (See for example, Ronald, J. A. et al. 2013 *PLoS One* e73138. doi: 10.1371/journal.pone.0073138) can also be employed.

Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus, canine or feline herpes virus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, Dtype viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

Exemplary Antibodies

In some embodiments, a recombinant genetic construct comprising an antibody gene that encodes an antibody or a fragment thereof that binds to a protein, a peptide, or a small molecule specific to reproductive function is provided. The genetic construct can be configured to be delivered and expressed in an animal subject. In some embodiments, the antibody inhibits a protein specific to reproductive function.

In some embodiments, the protein specific to reproductive function is one that, when bound by the antibody, causes sterility. In some embodiments, the protein is a reproductive hormone, a protein component of the egg zona pellucida, or a protein component of the sperm plasma membrane. In some embodiments, the antibody binds to human CD52. In some embodiments, the antibody binds to a carbohydrate epitope expressed specifically on CD52 in the human male reproductive system. In some embodiments, the reproductive hormone is selected from one or more of the group consisting of gonadotropin-releasing hormone (GnRH), luteinizing hormone (LH), follicle-stimulating hormone (FSH), chorionic gonadotropin, and testosterone.

In some embodiments, the antibody comprises an amino acid sequence that is at least 90% identical to that in SEQ ID NO: 2. In some embodiments, the antibody comprises 6 CDRs, wherein the 6 CDRs are 6 CDRs within SEQ ID NO: 2. In some embodiments, a nucleic acid sequence that encodes one or more of the above is provided for use in the vector.

In some embodiments, the antibody comprises the amino acid sequence of SEQ ID NO: 4. In some embodiments, the antibody comprises an amino acid sequence that is at least 90% identical to that in SEQ ID NO: 4. In some embodiments, the antibody comprises 6 CDRs, wherein the 6 CDRs are 6 CDRs within SEQ ID NO: 4. In some embodiments, a nucleic acid sequence that encodes one or more of the above is provided for use in the vector.

In some embodiments, the antibody comprises the amino acid sequence of that depicted in FIG. 9. In some embodiments, the antibody comprises an amino acid sequence that is at least 90% identical to that depicted in FIG. 9. In some embodiments, the antibody comprises 6 CDRs, wherein the 6 CDRs are 6 CDRs within FIG. 9. In some embodiments, a nucleic acid sequence that encodes one or more of the above is provided for use in the vector.

In some embodiments, the antibody comprises the amino acid sequence of that depicted in FIG. 10. In some embodiments, the antibody comprises an amino acid sequence that is at least 90% identical to that depicted in FIG. 10. In some embodiments, the antibody comprises 6 CDRs, wherein the 6 CDRs are 6 CDRs within FIG. 10. In some embodiments, a nucleic acid sequence that encodes one or more of the above is provided for use in the vector.

In some embodiments, the antibody comprises the amino acid sequence of SEQ ID NO: 6, 8, or 6 and 8. In some embodiments, the antibody comprises an amino acid sequence that is at least 90% identical to that in SEQ ID NO: 6, 8, or 6 and 8. In some embodiments, the antibody comprises 6 CDRs, wherein the 6 CDRs are 6 CDRs within SEQ ID NOs: 6 and 8. In some embodiments, a nucleic acid sequence that encodes one or more of the above is provided for use in the vector.

In some embodiments, the antibody comprises the amino acid sequence of SEQ ID NO: 10, 12, or 10 and 12. In some embodiments, the antibody comprises an amino acid sequence that is at least 90% identical to that in SEQ ID NO: 10, 12, or 10 and 12. In some embodiments, the antibody comprises 6 CDRs, wherein the 6 CDRs are 6 CDRs within SEQ ID NOs: 10 and 12. In some embodiments, a nucleic acid sequence that encodes one or more of the above is provided for use in the vector.

In some embodiments, the antibody comprises the amino acid sequence of SEQ ID NO: 13, 14, or 13 and 14. In some embodiments, the antibody comprises an amino acid sequence that is at least 90% identical to that in SEQ ID NO: 13, 14, or 13 and 14. In some embodiments, the antibody comprises 6 CDRs, wherein the 6 CDRs are 6 CDRs within SEQ ID NOs: 13 and 14. In some embodiments, a nucleic acid sequence that encodes one or more of the above is provided for use in the vector.

In some embodiments, the antibody has a $K_D$ of no greater than 1E−9(M). In some embodiments, the antibody has a $k_{on}$ of greater than 4.0E+6(1/Ms). In some embodiments, the antibody has a $k_{off}$ of no greater than 2.8E−3(1/S). In some embodiments, a nucleic acid sequence that encodes one or more of the above is provided for use in the vector.

In some embodiments, the immunocontraceptive molecule can include an antibody (and thus, the immunocontraceptive that is administered includes a nucleic acid sequence that encodes for the antibody). In some embodiments, the immunocontraceptive molecule is an immunocontraceptive antibody. In some embodiments, the immunocontraceptive antibody can be any that alters the ability of an organism to reproduce to a satisfactory level for the intended purpose. In some embodiments, the immunocontraceptive antibody is the mouse monoclonal antibody HB-9094 (described in U.S. Pat. Nos. 4,676,981 and 4,879,112) and the mouse monoclonal antibody SMI 41 (reacts with LHRH and is specific for the C-terminal pentapeptide). In some embodiments, a nucleic acid construct that encodes the above can be employed. In some embodiments, the nucleic acid sequence also encodes for a signal peptide sequence (MATGSRTSLLLAFGLLCLPWLQEGSA; SEQ ID NO: 15) and/or an F2Aopt peptide (RKRRSGS-GAPVKQTLNFDLLKLAGDVESNPGP; SEQ ID NO: 16).

In some embodiments, the promoter comprises cytomegalovirus (CMV) immediate early promoter, chicken beta-actin (CAG) promoter, ubiquitin C CUBC) promoter, or any variant thereof. In some embodiments, the promoter comprises a splice donor, a splice acceptor, or any variant thereof.

In some embodiments, the posttranscriptional regulatory element is a viral posttranscriptional regulatory element. In some embodiments, the viral posttranscriptional regulatory element is woodchuck hepatitis virus posttranscriptional regulatory element (WPRE), hepatitis B virus posttranscriptional regulatory element (HBVPRE), RNA transport element (RTE), or any variant thereof.

In some embodiments, the viral vector further comprises a transcription termination region downstream of the posttranscriptional regulatory element. In some embodiments, the transcription termination region comprises an SV40 late poly(A) sequence, a rabbit beta-globin poly(A) sequence, a bovine growth hormone poly(A) sequence, or any variant thereof.

In some embodiments, the polynucleotide comprises a first coding region for the heavy chain variable region of an immunoglobulin and a second coding region for the light chain variable region of the immunoglobulin. In some embodiments, the first coding region and the second coding region are separated by a 2A sequence. In some embodiments, the 2A sequence is an F2A sequence.

In some embodiments, 5' of the first coding region is fused with a first signal peptide sequence and 5' of the second coding region is fused with a second signal peptide sequence.

In some embodiments, the first signal peptide sequence and the second signal peptide sequence are different.

In some embodiments, the antibody construct comprises an amino acid sequence comprising a signal peptide, a variable region and a F2Aopt peptide region, and wherein the F2Aopt peptide region includes the amino acid sequence of SEQ ID NO: 1.

There are a number of antibodies already known to target vital reproduction-related proteins. In some embodiments, any one or more of the antibodies provided herein can be used alone or in combination for the compositions and/or methods provided herein. For example the following antibodies can be used to target such reproductive proteins in males and females of multiple species: (i) mouse anti-GnRH: HB-9094 (USASK/DSIL-LHRH) (Silversides, D. W. et al. 1985 *Journal of reproductive immunology* 7: 171-184); (ii) mouse anti-GnRH: SMI 41 (Covance). In humans, the following antibodies can in principal be used: a. In Females: (i) mouse anti-human ZP3: (East, I. J. et al. 1985 *Dev Biol* 109: 268-273; East, I. J. et al. 1984 *Dev Biol* 104: 49-56); (ii) human anti-human hCG: (WO 2005095458 A1; Majumdar, R. et al. 2011 Proteins 79: 3108-3122); b. In Females and males: human anti-human mrtCD52: (Isojima, S. et al. 1987 *Journal of reproductive immunology* 10: 67-78; Komori, S. et al. 1988 *Clinical and experimental immunology* 71: 508-516; Sawai, H. et al. 1995 *Am J Reprod Immunol* 34: 26-34; Yamasaki, N. et al. 1987 *Molecular immunology* 24: 981-985). Thus, any one or more can be employed by employing a nucleic acid sequence that encodes for the molecule.

In the case of proteins for which no monoclonal antibodies exist, the following steps provide a straightforward path to their identification and characterization.

In some embodiments, one may generate antibodies in non-target species followed by conversion to a species-specific form. Immunize mice, rabbits, or the target species (below) using published techniques shown to induce generation of antibodies and immunocontraception in species of interest. Monoclonal antibodies that recognize the target can be identified through a variety of published methods. Alternatively, antibody phage display techniques can be used to create antibodies that recognize the target, in a completely in vitro setting.

In some embodiments, one may generate species-specific antibodies (e.g., humanized antibodies) to limit immunogenicity in the target species. If antibodies and their encoding genes of the appropriate specificity are identified in a non-target species such as mouse or rabbit, or are generated through phage display in a species other than the one being targeted, the genes are engineered so that the antibody is not seen as foreign in the species of interest (dog, cat, etc.). In the case of antibodies generated in mouse that are re-engineered to be invisible to the immune system of humans, this process is known as "humanizing" (Winter, G. and Harris, W. J. 1993 *Immunology today* 14: 243-246). Antibody-encoding genes generated in a non-target species (such as mouse or rabbit), that target the protein or small molecule of interest can be made to be species-specific so that they still recognize the target of interest, but are not seen as foreign when expressed in the target species. This approach focuses first on identifying antibodies with the ideal target-binding characteristics (high affinity and specificity), and then grafting these characteristics onto antibody scaffolds appropriate to the targeted species.

In some embodiments, one may identify antibodies directly in the species of interest. In a second, parallel approach, the species of interest (dogs, cats, pigs, cows, horses, humans, etc) are vaccinated with the antigen of interest and accompanying adjuvants. Memory B cells or blastocysts are isolated, using published protocols, from a simple blood draw (Kurosawa, N. et al. 2012 *BMC biology* 10: 80; Kurosawa, N. et al. 2011 *BMC biotechnology* 11: 39; Smith, K. 2009 *Nature protocols* 4: 372-384). Those cells that express antibodies that bind the molecule of interest are isolated, using standard procedures that involve cell sorting with fluorescently labeled antigen (Tiller, T. et al. 2009 *J Immunol Methods* 350: 183-193). In this implementation there is no need to convert the antibody to become species-specific. Evidence that this approach is predicted to work comes from observations such as those noted above demonstrating that vaccination of dogs and cats with GnRH results in the production of anti-GnRH antibodies and suppression of reproductive function (Donovan, C. et al. 2012 *Reproduction in Domestic Animals* 47 (Suppl 6): 403-405; Robbins, S. C. et al. 2004 *Journal of reproductive immunology* 64: 107-119), and observations in a number of other species demonstrating that vaccination with components of the zona pellucida results in the production of anti-zona pellucida antibodies and suppression of reproduction in females (Gupta S K, Srinivasan V A, Suman P, Rajan S, Nagendrakumar S B, Gupta N, Shrestha A, Joshi P, Panda A K. Contraceptive vaccines based on the zona pellucida glycoproteins for dogs and other wildlife population management. Am J Reprod Immunol 2011; 66: 51-62).

In some embodiments, memory B cells or blastocysts will be isolated directly from infertile human patients. Cells will be identified as interesting based on their ability to produce antibodies that bind to sperm or other components of semen, or to cells of the female reproductive tract.

In some embodiments, one may increase antibody Half-life. The longer the serum half-life of an antibody, the less of it needs to be synthesized in order to maintain a given concentration. These include, but are not limited to published mutations in the antibody-encoding gene designed to extend half-life described in Swann et al. (Swann, P. G. et al. 2008 *Current opinion in immunology* 20: 493-499).

In some embodiments, one may eliminate and/or reduce antibody effector function. For those antibodies designed to target reproductive hormones, and for those designed to target the ZP in humans, it can be useful for the antibodies to not have significant off target effects that cause unwanted tissue damage. While it can be difficult to ensure no off-target binding, the consequences of off-target binding can be minimized. This is achieved by introducing published mutations into the antibody-encoding gene that block the ability of the mature antibody to recruit effector functions that result in cell death, phagocytosis, or activation of a cytokine storm (Desjarlais, J. R. and Lazar, G. A. 2011 *Exp Cell Res* 317: 1278-1285). Antibodies so modified will only act only as sponges, binding the relevant molecule and blocking its ability to function. These include, but are not limited to, V234A/G237A/P238S/H268A/V309L/29A330S/P331S substitutions into human IgG2 (O. Vafa et al. 2014 *Methods* 65: 114-26).

In some embodiments, one may enhance antibody effector function. In the case of feral animals, it may be desirable to enhance effector functions of antibodies that target the ZP or sperm. Enhanced complement-mediated killing, or antibody-dependent cellular cytotoxicity may allow levels of antibody that are not sufficient to prevent sperm binding to the ZP to still inhibit fertility, by eliminating the developing follicle or damaging sperm, respectively. Published mutations are introduced into the antibody encoding gene so as to promote effector function. These include, but are not limited to those described in Desjarlais et al. (Desjarlais, J. R. and Lazar, G. A. 2011 *Exp Cell Res* 317: 1278-1285). In addition, as discussed below, immunoglobulin class switching may be carried out to modulate antibody access to specific tissues, and to enhance or suppress effector function. In one specific implementation, IgG antibodies that target the ZP will be switched to IgM, which has increased ability to promote complement activation.

In some embodiments, one may modulate tissue distribution and effector function through class switching. Different antibody classes: IgA, IgG1-4, IgE, and IgM, have distinct tissue tropisms and effector functions. Standard approaches are used to swap constant region domains that mediate these functions in order to modulate antibody localization and effector characteristics.

In some embodiments, infertility and/or infertility-associated traits can be reversed. This can be achieved in several ways. In some embodiments, site-specific recombinase target sites are introduced between the enhancer-promoter sequences driving antibody expression and the antibody-encoding gene itself. These sites are arranged in such a way (as direct repeats) that recombinase activity separates the enhancer-promoter fragment from the protein being expressed, thereby silencing gene expression. Alternatively, the recombinase sites are arranged so that recombinase action results in inversion of the enhancer-promoter, also resulting in loss of protein expression (Saunders, A. et al. 2012 *Frontiers in neural circuits* 6: 47). In these implementations, the recombinase itself is introduced into antibody expressing cells either as a protein, an mRNA, or as a DNA construct from which protein expression is induced. This approach requires that the recombinase be introduced into cells that express the antibody. In one implementation, inducible expression of the recombinase may be brought about through use of drug-dependent protein dimerization (e.g. Chen, S-J., et al. 2013 *Hum Gene Ther Methods.* 24: 270-278).

In some embodiments the second protein expressed in antibody-producing cells using approaches noted above will be a site-specific nuclease designed to make one or more double-standed DNA breaks within any region of the antibody-expressing transgene that disrupts its function when repaired through end-joining. Examples of nucleases which can be engineered to cleave in specific positions include zinc finger nucleases, TALENS, and CRISPR/Cas nucleases (reviewed in Gai, T. et al. 2013 *Trends Biotechnol.* 31: 397-405).

In some embodiments reversibility can be achieved by introducing into the antibody-producing cells a vector expressing microRNAs designed to silence expression of the engineered antibody. The appeal of this approach is that only non-coding RNA is expressed, minimizing the possibility that expression of the second construct will result in an immune response. When reversibility is desired the antibody-expressing gene is designed so as to include multiple target sites for the engineered microRNA. While such a strategy may not completely eliminate expression of the antibody, it will likely bring expression down to levels that allow fertility. Thus, in some embodiments, kits are provided with both the nucleic acid sequence encoding for the immunocontraceptive antibody, as well as an inhibitor of the immunocontraceptive, such as microRNAs or vectors expressing such microRNAs. In some embodiments, transient relief from the immunocontraception can be obtained by administering microRNAs or other blockers that block the immunocontraceptive antibodies (such as antibodies that bind to and block the immunocontraceptive antibody).

In some embodiments, the issue of bringing about gene expression in cells that express the reproduction-inhibiting antibody (the above-noted approaches) can be bypassed by generating and/or employing monoclonal antibodies (using standard approaches) that recognize sequences in the variable region that bind the target antigen. Expression of such an antibody, using a gene delivery system, prevents the original antibody from carrying out its function regardless of what tissue it is expressed in, since the antibody is secreted into serum, where it will interact with the original contraceptive antibody. A similar effect may be achieved by first introducing one or more epitope tags into the contraceptive antibody-encoding sequence that do not in and of themselves disrupt its contraceptive function. Binding of recombinant anti-epitope antibodies, introduced as above, can block the ability of the contraceptive antibody to interact productively with its target, thereby resulting in a reversal of infertility.

Genetic Constructs:

In some embodiments, the genetic construct (that will carry the nucleic acid sequence that encodes for the antibody) comprise an antibody expression cassette comprising a ubiquitous or tissue specific promoter, a regulatory element, and microRNA target sites. In some embodiments, the regulatory element is a 5' untranslated region (5' UTR) or a 3' untranslated region (3' UTR). In some embodiments, the promoter comprises cytomegalovirus (CMV) immediate early promoter, chicken beta-actin (CAG) promoter, ubiquitin C CUBC) promoter, or any variant thereof. In some embodiments, the promoter comprises a splice donor, a splice acceptor, or any variant thereof.

In some embodiments, the posttranscriptional regulatory element is a viral posttranscriptional regulatory element. In some embodiments, the viral posttranscriptional regulatory element is woodchuck hepatitis virus posttranscriptional regulatory element (WPRE), hepatitis B virus posttranscriptional regulatory element (HBVPRE), RNA transport element (RTE), or any variant thereof.

In some embodiments, the viral vector further comprises a transcription termination region downstream of the posttranscriptional regulatory element. In some embodiments, the transcription termination region comprises an SV40 late poly(A) sequence, a rabbit beta-globin poly(A) sequence, a bovine growth hormone poly(A) sequence, or any variant thereof. In some embodiments, the polynucleotide comprises a first coding region for the heavy chain variable region of an immunoglobulin and a second coding region for the light chain variable region of the immunoglobulin. In some embodiments, the first coding region and the second coding region are separated by a 2A sequence. In some embodiments, the 2A sequence is an F2A sequence.

In some embodiments, 5' of the first coding region is fused with a first signal peptide sequence and 5' of the second coding region is fused with a second signal peptide sequence. In some embodiments, the first signal peptide sequence and the second signal peptide sequence are different. In some embodiments, mir-142-3p target sites can be included. Mir-142-3p is expressed in antigen presenting cells. In some implementations mir-142-3p target sites are incorporated into the antibody-encoding transcription unit. Incorporation of these sites into the transgene transcript reduces immunogenicity following transgene delivery. (Majowicz et al. 2013 Journal of Gene medicine. 15: 219-232).

In some embodiments, the genetic construct is incorporated into a transfection vehicle selected from the group consisting of an adeno-associated virus (AAV), a lentivirus, a nanoparticle (which may be composed of a variety of molecules, but which typically has a size in at least one dimension less than 300 nm), liposome-DNA mixture, cationic peptide-DNA mixtures, phage, virus-like particles, polyplexes. Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosissarcoma, mammalian C-type, B-type viruses, Dtype viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference. Phage, virus-like particles can also be employed. In some implementations DNA or RNA encoding contraceptive encoding antibodies are introduced as complexes with inorganic particles such as calcium phosphate, silica, gold, or magnetic particles; other synthetic or biodegradable particles containing PLGA, PLA, PEI, chitosan, dendrimers, polymethacrylates, cationic liposomes, cationic emulsions, solid lipid nanoparticles, poly-1 lysine, poly arginine, as well as other peptides that provide particle condensation functions, endosomal escape functions, and/or nuclear transport functions. Delivery of the vector may occur through, but is not limited to, needle injection, balistic DNA injection, electroporation, sonoporation, photoporation, magnetofection, hydroporation, and inhalation.

In some embodiments, the genetic construct encodes an antibody or fragment thereof that comprises an amino acid modification that enhances or suppresses an effector function of the encoded antibody or fragment.

In some embodiments, the genetic construct that encodes the antibody comprises the nucleic acid sequence of SEQ ID NO: 1. In some embodiments, the genetic construct that encodes the antibody comprises a nucleic acid sequence that is at least 90% identical to that in SEQ ID NO: 1. In some embodiments, the genetic construct that encodes the antibody comprises 6 CDR coding regions, wherein the 6 CDRs are 6 CDRs within SEQ ID NO: 1.

In some embodiments, the genetic construct that encodes the antibody comprises the nucleic acid sequence of SEQ ID NO: 3. In some embodiments, the genetic construct that encodes the antibody comprises a nucleic acid sequence that is at least 90% identical to that in SEQ ID NO: 3. In some embodiments, the genetic construct that encodes the antibody comprises 6 CDR coding regions, wherein the 6 CDRs are 6 CDRs within SEQ ID NO: 3.

In some embodiments, the genetic construct that encodes the antibody comprises the nucleic acid sequence of SEQ ID NO: 5, 7, or 5 and 7. In some embodiments, the genetic construct that encodes the antibody comprises a nucleic acid sequence that is at least 90% identical to that in SEQ ID NOs: 5, 7, or 5 and 7. In some embodiments, the genetic construct that encodes the antibody comprises 6 CDR coding regions, wherein the 6 CDRs are 6 CDRs within SEQ ID NO: 5 and 7.

In some embodiments, the genetic construct that encodes the antibody comprises the nucleic acid sequence of SEQ ID NO: 9, 11, or 9 and 11. In some embodiments, the genetic construct that encodes the antibody comprises a nucleic acid sequence that is at least 90% identical to that in SEQ ID NO: SEQ ID NO: 9, 11, or 9 and 11. In some embodiments, the genetic construct that encodes the antibody comprises 6 CDR coding regions, wherein the 6 CDRs are 6 CDRs within SEQ ID NO: SEQ ID NOs: 9 and 11.

Provided herein are polynucleotides comprising a nucleotide sequence encoding an immunocontraceptive molecule, such as an antibody, or binding fragments thereof. In some embodiments, this is provided as polynucleotides that hybridize under stringent or lower stringency hybridization conditions to polynucleotides that encode an antibody, preferably, that specifically binds to a protein related to reproduction. Thus, in some embodiments, the polynucleotide can be one that hybridizes under stringent conditions to any of the sequences in SEQ ID NOs: 1, 3, 5, 7, 8, and/or 11. In some embodiments, additional and/or alternative nucleic acid sequence can be employed (and thus, the immunocontraceptive molecules and polynucleotides encoding the same are not limited to those sequences provided herein).

The polynucleotides can be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al. 1994 *BioTechniques* 17: 242), which, briefly, involves the synthesis of overlapping oligonucleotides containing portions of the sequence encoding the antibody, annealing and ligating of those oligonucleotides, and then amplification of the ligated oligonucleotides by PCR.

In some embodiments, a polynucleotide encoding an antibody can be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly $A^+$ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al. 1998 *J Mol Biol* 278: 457-479) for a listing of human framework regions). Analogous approaches can be used to insert CDRs into framework regions from other organisms when these organisms are to be targeted. Framework regions from immunoglobulins of other organisms can be identified using computation tools such as those found at the world wide web "bioinf.org.uk/abysis/". Preferably, the polynucleotide generated by the combination of the framework regions and CDRs encodes an antibody that specifically binds a polypeptide. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intra-chain disulfide bond to generate antibody molecules lacking one or more intra-chain disulfide bonds. Other alterations to the polynucleotide are encompassed by the present invention and within the skill of the art.

In addition, techniques developed for the production of "chimeric antibodies" (Morrison et al. 1984 *Proc Natl Acad Sci* 81: 851-855; Neuberger et al. 1984 *Nature* 312: 604-608; Takeda et al. 1985 *Nature* 314: 452-454) by splicing genes from a mouse antibody molecule of appropriate antigen specificity together with genes from a human antibody molecule (or antibody molecule from some other species of interest) of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988 *Science* 242: 423-442; Huston et al. 1988 *Proc Natl Acad Sci USA* 85: 5879-5883; and Ward et al. 1989 *Nature* 334: 544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al. 1988 *Science* 242: 1038-1041). Monovalent single chain antibodies with a long half-life can also be generated through manipulation of Fc sequences (Ishino, T. et al. 2013 *J Biol Chem.* 2013 288: 16529-37; Wilkinson, I. C. et al. 2013 *mAbs* 5: 406-417)

In some embodiments, a method of contraception is provided. The method can include administering one or more of the immunocontraceptive molecules to a subject. As noted herein, the administration is achieved by administering a nucleic acid sequence that encodes for the immunocontraceptive molecule. In some embodiments, this is achieved by administering to said animal a genetic construct as provided herein. In some embodiments, the genetic construct is transiently expressed in the animal. In some embodiments, the genetic construct is reversibly expressed in the animal. In some embodiments, the genetic construct is permanently expressed in said animal.

In some embodiments, the animal is not human. In some embodiments, the animal is selected from the group consisting of dog, cat, pig, cow, horse, deer, burro, fox, primate, elephant, rodent, mouse, rat, rabbit, and marsupial.

In some embodiments, the administration can be done in any manner. In some embodiments, the administering comprises a single shot administration to said animal. In some embodiments, 2 or more administrations can be given, for example, 2, 3, 4, 5, 6, 7, 8, 9 10 or more. However, in some embodiments, a single administration of one or more genes encoding one or more immunocontraceptive molecules can be applied. In some embodiments, administering comprises a single intramuscular administration of the genetic construct. In some embodiments, the single administration last for at least 1 year, for example, at least 2, 3, 4, 5, 6, 7, 8, 9, or 10 years. In some embodiments, an additional administration is not required and/or not applied for at least 1 year, for example, 2, 3, 4, 5, 6, 7, 8, 9, or 10 years.

In some embodiments, nucleic acids comprising sequences encoding antibodies or functional derivatives thereof are administered as a contraceptive. The nucleic acid sequences are part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In some embodiments, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies 1989 *Proc Natl Acad Sci USA* 86: 8932-8935; Zijlstra et al. 1989 *Nature* 342: 435-438. In some embodiments, the expressed antibody molecule is a single chain antibody; alternatively, the nucleic acid sequences include sequences encoding both the heavy and light chains, or fragments thereof, of the antibody. Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo administration.

In some embodiments, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286 and above), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu 1987 *J Biol Chem* 262: 4429-4432) (which can be used to target cell types specifically expressing the receptors), and see above etc. In some embodiments, nucleic acid-ligand complexes can be formed in which the ligand comprises a fusogenic viral peptide to disrupt endosomes, allowing the nucleic acid to avoid lysosomal degradation. In some embodiments, the nucleic acid can be targeted in vivo for cell specific uptake and expression, by targeting a specific receptor (see, e.g., WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies 1989 *Proc Natl Acad Sci USA* 86: 8932-8935; Zijlstra et al. 1989 *Nature* 342: 435-438).

In some embodiments, viral vectors that contain nucleic acid sequences encoding an antibody that is an immunocontraceptive are used. For example, a retroviral vector can be used (see Miller et al. 1993 *Meth Enzymol* 217: 581-599). These retroviral vectors contain the components necessary for the correct packaging of the viral genome and integration into the host cell DNA. The nucleic acid sequences encoding the antibody to be used in the disclosed methods are cloned into one or more vectors, which facilitates delivery of the gene into a patient. More detail about retroviral vectors can be found in Boesen et al. 1994 *Biotherapy* 6: 291-302, which describes the use of a retroviral vector to deliver the mdrl gene to hematopoietic stem cells in order to make the stem cells more resistant to chemotherapy. Other references illustrating the use of retroviral vectors in gene delivery and expression are: Clowes et al. 1994 *J Clin Invest* 93: 644-651; Kiem et al. 1994 *Blood* 83: 1467-1473; Salmons and Gunzberg 1993 *Human Gene Therapy* 4: 129-141; and Grossman and Wilson 1993 *Curr Opin in Genetics and Devel* 3: 110-114.

Adenoviruses are other viral vectors that can be used in gene delivery and expression. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson 1993 *Current Opinion in Genetics and Development* 3: 499-503 present a review of adenovirus-based gene delivery and expression. Bout et al. 1994 *Human Gene Therapy* 5: 3-10 demonstrated the use of adenovirus vectors to transfer genes to the respiratory epithelia of rhesus monkeys. Other instances of the use of adenoviruses in gene delivery and expression can be found in Rosenfeld et al. 1991 *Science* 252: 431-434; Rosenfeld et al. 1992 *Cell* 68: 143-155; Mastrangeli et al. 1993 *J Clin Invest* 91: 225-234; WO94/12649; and Wang, et al. 1995 *Gene Therapy* 2: 775-783. In some embodiments, adenovirus vectors are used.

Adeno-associated virus (AAV) are also use in gene delivery and expression (Walsh et al. 1993 *Proc Soc Exp Biol Med* 204: 289-300; U.S. Pat. No. 5,436,146). Non-integrating AAV vectors can be employed in some embodiments.

Another approach to gene delivery and expression involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr 1993 *Meth Enzymol* 217: 599-618; Cohen et al. 1993 *Meth Enzymol* 217: 618-644; Cline 1985 *Pharmac Ther* 29: 69-92, and may be used, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene delivery and expression encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene delivery and expression is autologous to the patient.

In some embodiments in which recombinant cells are used in gene delivery and expression, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment (see e.g. WO 94/08598; Stemple and Anderson 1992 *Cell* 71: 973-985; Rheinwald 1980 *Meth Cell Bio* 21A: 229; and Pittelkow and Scott 1986 *Mayo Clinic Proc* 61: 771).

In some embodiments, the nucleic acid to be introduced for purposes of gene delivery and expression comprises an inducible promoter operably linked to the coding region, such that expression of the nucleic acid is controllable by controlling the presence or absence of the appropriate inducer of transcription.

The gene delivery and expression methods relate to the introduction of nucleic acid (DNA, RNA and antisense DNA or RNA) sequences into an animal to achieve expression of an immunocontraceptive polypeptide. This method involves a polynucleotide which codes for an immunocontraceptive polypeptide that is operatively linked to a promoter and any other genetic elements necessary for the expression of the polypeptide by the target tissue. Such gene expression and delivery techniques are known in the art, see, for example, WO 90/11092, which is herein incorporated by reference.

Thus, for example, cells from a patient may be engineered with a polynucleotide (DNA or RNA) comprising a promoter operably linked to an immunocontraceptive polynucleotide ex vivo, with the engineered cells then being provided to a patient to be treated with the polypeptide. Such methods are well-known in the art. For example, see Belldegrun et al. 1993 *J Natl Cancer Inst* 85: 207-216; Ferrantini et al. 1993 *Cancer Research* 53: 107-1112; Ferrantini et al. 1994 *J Immunology* 153: 4604-4615; Kaido, T., et al. 1995 *Int J Cancer* 60: 221-229; Ogura et al. 1990 *Cancer Research* 50: 5102-5106; Santodonato, et al. 1996 *Human Gene Therapy* 7:1-10; Santodonato, et al. 1997 *Gene Therapy* 4: 1246-1255; and Zhang, et al. 1996 *Cancer Gene Therapy* 3: 31-38), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs can be delivered in a pharmaceutically acceptable liquid or aqueous carrier.

In some embodiments, the immunocontraceptive polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the immunocontraceptive polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs are preferably constructs that will not integrate into the host genome. In some implementations the constructs may contain sequences that promote replication in conjunction with the cell cycle, thereby maintaining the construct over time in replicating cells Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Life Technologies. Other suitable vectors will be readily apparent to the skilled artisan.

Figure 5:
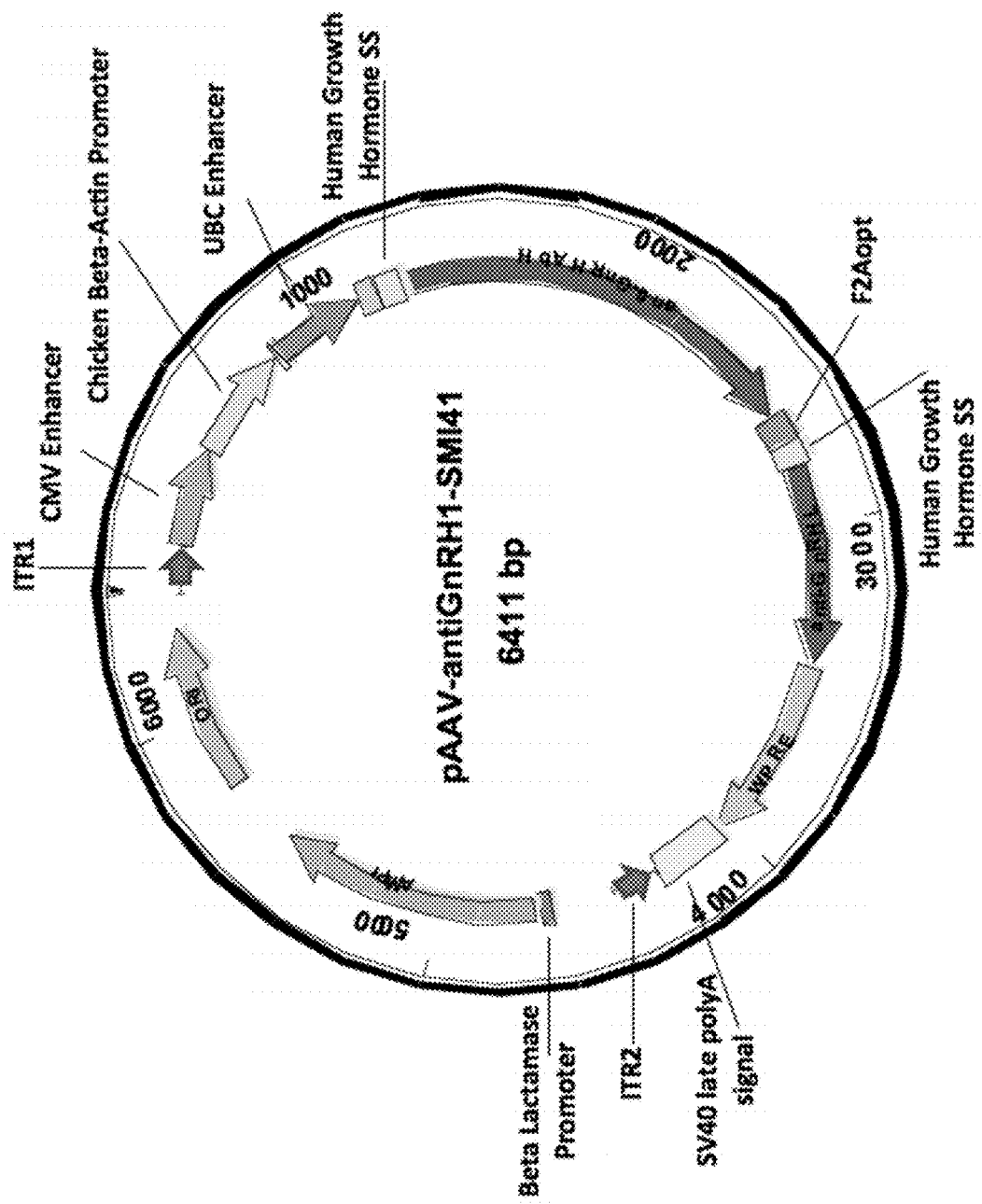
FIG. 5 depicts some embodiments of a pAAV vector including the antiGnRH1-SMI41 construct.

Any strong promoter can be used for driving the expression of the immunocontraceptive polynucleotide. Suitable promoters include the composite promoter illustrated in FIG. 5, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the immunocontraceptive polynucleotides.

Unlike other gene delivery techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

In some embodiments, cells are engineered, ex vivo or in vivo, using a retroviral particle containing RNA which comprises a sequence encoding immunocontraceptive polypeptides. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. Why are we now going into a detailed description of several different viral vectors for in vivo and ex vivo therapy.

The retroviral plasmid vector is employed to transduce packaging cell lines to form producer, cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding immunocontraceptive polypeptides. Such retroviral vector particles then may be employed, to transduce eukaryotic cells, either in vitro or in vivo. The transduced eukaryotic cells will express immunocontraceptive polypeptides.

In some embodiments, cells are engineered, ex vivo or in vivo, with immunocontraceptive polynucleotides contained in an adenovirus vector. Adenovirus can be manipulated such that it encodes and expresses immunocontraceptive polypeptides, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al. 1974 *Am Rev Respir Dis* 109: 233-238). Finally, adenovirus mediated gene transfer has been demonstrated in a number of instances including transfer of alpha-1-antitrypsin and CFTR to the lungs of cotton rats (Rosenfeld et al. 1991 *Science* 252: 431-434; Rosenfeld et al. 1992 *Cell* 68: 143-155). Furthermore, extensive studies to attempt to establish adenovirus as a causative agent in human cancer were uniformly negative (Green et al. 1979 *Proc Natl Acad Sci USA* 76: 6606).

Suitable adenoviral vectors are described, for example, in Kozarsky and Wilson 1993 *Curr Opin Genet Devel* 3: 499-503; Rosenfeld et al. 1992 *Cell* 68: 143-155; Engelhardt et al. 1993 *Human Genet Ther* 4: 759-769; Yang et al. 1994 *Nature Genet* 7: 362-369; Wilson et al. 1993 *Nature* 365: 691-692; and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, AdS, and Ad7) are also useful.

Preferably, the adenoviruses are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In some embodiments, the cells are engineered, ex vivo or in vivo, using an adeno-associated virus (AAV). AAVs are naturally occurring defective viruses that require helper viruses to produce infectious particles (Muzyczka, 1992 *Curr Topics in Microbiol Immunol* 158: 97). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941; 5,173,414; 5,354,678; 5,436,146; 5,474,935; 5,478,745; and 5,589,377.

For example, an appropriate AAV vector for use can include all the sequences necessary for DNA replication, encapsidation, and host-cell integration. The polynucleotide construct containing immunocontraceptive polynucleotides is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the immunocontraceptive polynucleotide construct. These viral particles are then used to transduce eukaryotic cells, either ex vivo or in vivo. The transduced cells will contain the polynucleotide construct integrated into its genome, and will express the desired gene product. Alternatively, in the more modern versions of AAV, virus is generated that remains episomal.

Preferably, the polynucleotide encoding a polypeptide contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., ALZA® minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al. 1989 *Science* 243: 375).

A preferred method of local administration is by direct injection. Preferably, a recombinant molecule complexed with a delivery vehicle is administered by direct injection into or locally within the area of arteries. In some embodiments, the gene is delivered intramuscularly.

Another method of local administration is to contact a polynucleotide construct in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules complexed to a targeted delivery vehicle. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al. 1992 *Proc Natl Acad Sci USA* 189: 11277-11281, which is incorporated herein by reference). Oral delivery can be performed by complexing a polynucleotide construct to a carrier capable of withstanding degradation by digestive enzymes in the gut of an animal. Examples of such carriers, include plastic capsules or tablets, such as those known in the art. Topical delivery can be performed by mixing a polynucleotide construct with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions can be administered to any animal, preferably to mammals. Preferred mammals include humans, dogs, cats, mice, rats, rabbits sheep, cattle, horses, pigs, fox, deer, coyote, various marsupials and others listed in table 2 and the references provided herein.

In some embodiments, one or more of the genetic constructs provided herein can be part of a contraceptive composition. In some embodiments, 2, 3, 4, 5, 6, 7, 8, 9, 10 or more such genetic constructs, and/or such nucleic acids encoding for an immunocontraceptive molecule can be present in a pharmaceutical composition. In some embodiments, the composition is configured to be delivered to an animal through intramuscular injection, subcutaneous injection, intravenous injection, intraperitoneal injection, oral delivery, electroporation through the skin, sonication, or nasal inhalation.

In some embodiments, a pharmaceutical composition is provided. The composition can comprise one or more of the genetic constructs provided herein. The composition can also include a pharmaceutically acceptable carrier. In some embodiments, the genetic construct is present in at least 1 µg/mL. In some embodiments, the pharmaceutically acceptable carrier can be combined with a nucleic acid. In some embodiments, the pharmaceutically acceptable carrier can be used with AAV. In some embodiments, this could be combined with a rabies therapy.

In some embodiments, the AAV is resuspended in culture media or pbs.

In some embodiments, a non-human animal or method of making an animal that has been sterilized is provided. In some embodiments, a transgenic animal comprising the genetic construct is provided. The animal can include one or more of a gene that encodes for an immunocontraceptive. In some embodiments, the genetic construct is stably expressed in said animal.

Provided below are further processes and alternatives to engineering antibody-mediated immunocontraception:

In some embodiments, additional targets for immunocontraception (and antibodies that bind thereto) can be determined and/or employed. One target for immunocontraception in both sexes is GnRH1. GnRH1 is a decapeptide hormone. It is synthesized in the hypothalamus and acts in the pituitary where it promotes the release of LH and FSH. FSH and LH are required for development and maintenance of gonads in males and females. Thus, inhibiting GnRH function provides a universal method of de-sexualizing behavior and sterilizing both males and females of a target species. Importantly, the protein sequence of GnRH1 is identical in most mammals (Schneider, F. et al. 2006 *Theriogenology* 66: 691-709). Therefore, it is expected that antibodies that recognize GnRH in one species will recognize it in other species as well.

Immunization of mice, rabbits, or target species of interest can be carried out using published techniques shown to induce generation of antibodies and immunocontraception in species of interest. Monoclonal antibodies that recognize the target can be identified through a variety of published methods. Alternatively, antibody phage display techniques can be used to create antibodies that recognize the target, in a completely in vitro setting.

In some embodiments, one can adapt the antibody to the species of interest. Once antibodies (and their encoding genes) of the appropriate specificity are identified in mouse or rabbit, the genes will be engineered so that the antibody is not seen as foreign in the species of interest (dog, cat, etc). In the case of antibodies generated in mouse that are re-engineered to be invisible to the immune system of humans, this process is known as "humanizing" (Winter, G. and Harris, W. J. 1993 *Immunology today* 14: 243-246).

In some embodiments, one may increase the antibody serum half-life. The longer the serum half-life of an antibody, the less of it that needs to be synthesized in order to maintain a given concentration. Published mutations in the antibody-encoding gene will be included that are designed to extend half-life (Swann, P. G. et al. 2008 *Current opinion in immunology* 20: 493-499).

In some embodiments, one may minimize off-target effects by eliminating antibody effector function. It is useful to ensure that antibodies that bind targets do not have significant off target effects that cause unwanted tissue damage. While it can be difficult to ensure no off-target binding, the consequences of off-target binding can be minimized. This is achieved by introducing published mutations into the antibody-encoding gene that block the ability of the mature antibody to recruit effector functions that result in cell death, phagocytosis, or activation of a cytokine storm. Examples include, but are not limited to those described in Desjarlais and Lazar (Desjarlais, J. R. and Lazar, G. A. 2011 *Exp Cell Res* 317: 1278-1285). Antibodies so modified will only act only as sponges, binding the relevant molecule and blocking its ability to function.

In some embodiments one may allow for reversability of the immunocontraception. There can be contexts in which it would be useful to be able to reverse sterility. This can be achieved by introducing into the antibody-producing cells a vector expressing microRNAs designed to silence expression of the engineered antibody. The appeal of this approach is that only non-coding RNA is expressed, minimizing the possibility that expression of the second construct will result in an immune response. When reversibility is desired the antibody-expressing gene is designed so as to include multiple target sites for the engineered microRNA. While such a strategy may not completely eliminate expression of the antibody, it will likely bring expression down to levels that allow fertility. Thus, in some embodiments, kits are provided with both the nucleic acid sequence encoding for the immunocontraceptive antibody, as well as an inhibitor of the immunocontraceptive, such as microRNAs or vectors expressing such microRNAs. In some embodiments, transient relief from the immunocontraception can be obtained by administering microRNAs or other blockers that block the immunocontraceptive antibodies (such as antibodies that bind to and block the immunocontraceptive antibody).

In some embodiments, the issue of bringing about gene expression in cells that express the reproduction-inhibiting antibody (the above-noted approaches) can be bypassed by generating and/or employing monoclonal antibodies (using standard approaches) that recognize sequences in the variable region that bind the target antigen. Expression of such an antibody, using a gene delivery system, prevents the original antibody from carrying out its function regardless of what tissue it is expressed in, since the antibody is secreted into serum, where it will interact with the original contraceptive antibody. A similar effect may be achieved by first introducing one or more epitope tags into the contraceptive antibody-encoding sequence that do not in and of themselves disrupt its contraceptive function. Binding of recombinant anti-epitope antibodies, introduced as above, can block the ability of the contraceptive antibody to interact productively with its target, thereby resulting in a reversal of infertility.

In some embodiments, one may introduce the antibody-expressing gene into muscle. Much work has been done to identify methods for introducing genes into muscle cells. Some of this work has the goal of treating diseases of muscle. Other work utilizes muscle as a convenient expression platform for secreted products designed to function elsewhere. Therefore, there are a variety of possible methods to choose from.

In some embodiments, one may employ an Adeno-associated virus (AAV). AAV vectors have been used by multiple groups to drive long-term expression of antibody-encoding genes in skeletal muscle (Balazs, A. B. et al. 2012 *Nature* 481: 81-84; Johnson, P. R. et al. 2009 *Nat Med* 15: 901-906). In dog models of muscular dystrophy these vectors have been shown to drive expression for more than 5 years (Vulin, A. et al. 2012 *The journal of the American Society of Gene Therapy* 20: 2120-2133). These vectors have also recently been used to drive gene expression in human patients (Nathwani, A. C. et al. 2011 *The New England journal of medicine* 365: 2357-2365). They have also been used to drive long-term expression of antibodies that target other molecules of medical interest, such as cocaine (Rosenberg, J. B. et al. 2012 *Hum Gene Ther* 23: 451-459) and nicotine (Hicks, M. J. et al. 2012 *Sci Transl Med* 4: 140ra187). Thus, they are an obvious choice that uses off-the-shelf technology.

In some embodiments, one may employ other gene delivery technologies. Other available gene delivery technologies include nanoparticles, electroporation, and liposomes with various compositions.

In some embodiments, the methods or compositions provided herein can be employed for contraception in cats and dogs. To date, spaying and neutering occurs through surgery. This prevents reproduction. It also eliminates hormones that can cause behavior problems (aggression and territoriality). Surgery costs vary depending on region and whether the owner qualifies for reduced cost. In addition, surgery based techniques can also require pain medication. However, in some embodiments, the present methods and compositions allow for contraception without pain medication.

There are large numbers of feral cats (upwards of 70 million) and dogs (numbers not clear). This population has two sources, pets and their progeny that are abandoned, and progeny of feral animals. These animals cause a number of problems. These include: bites (with associated potential for disease transmission), killing other species (cats and birds, dogs and livestock etc.), costs associated with removal and euthanasia. Currently the only options available are neutering through surgery or euthanasia. To summarize, it has been appreciated that there is need for a cheap, single dose, lifetime contraceptive that can be implemented in the clinic and in the field.

In some embodiments, the immunocontraceptive can be used to substitute for one of the products listed below, which bring about vaccination of the individual with an antigen and adjuvant. The antigen to which antibodies are to be raised and incorporated into an expression vector is indicated in parentheses.

1) Gonacon (GnRH): Pfizer animal health (deer, dog, cat eastern gray squirrel) (Levy, J. K. 2011a *Am J Reprod Immunol* 66: 63-70; Miller, L. A. et al. 2008 *Am J Reprod Immunol* 60: 214-223; Pai, M. et al. 2011 *Journal of zoo and wildlife medicine: official publication of the American Association of Zoo Veterinarians* 42: 718-722; Vargas-Pino, F. et al. 2013 *Vaccine* 31: 4442-4447; Wu, X. et al. 2009 *Vaccine* 27: 7202-7209; Yoder, C. A. and Miller, L. A. 2010 *Vaccine* 29: 233-239).

2) Improvac (GnRH): (pigs) (Dunshea, F. R. et al. 2001 *Journal of animal science* 79: 2524-2535). Horses also. Pfizer animal health Australia.

3) Equity (GnRH): (horse) (Wenzinger, B. et al. 2010 *Schweizer Archiv fur Tierheilkunde* 152: 373-377) (Janett, F. et al. 2009 *Animal reproduction science* 115: 88-102). Pfizer animal health Australia.

4) Bopriva (GnRH): (cow) (Amatayakul-Chantler, S. et al. 2013 *Meat science* 95: 78-84; Amatayakul-Chantler, S. et al. 2012 *Journal of animal science* 90: 3718-3728; Janett, F. et al. 2012 *Theriogenology* 78: 182-188; Janett, F. et al. 2012 *Animal reproduction science* 131: 72-80; Theubet, G. et al. 2010 *Schweizer Archiv fur Tierheilkunde* 152: 459-469).

5) Spayvac (Zona pellucida): (deer) (Fraker, M. A. et al. 2002 *Journal of Wildlife Management* 66: 1141-1147; Locke, S. L. et al. 2007 *Journal of wildlife diseases* 43: 726-730).

6) PZP (Zonastat-H. (Zona pellucida): (horse). Humane society, USA

In some embodiments, the immunocontraceptive can be used for, or configured for use in, any number or type of organisms, including, for example, those listed in Table 1, for any one or more of the purposes listed in Table 1.

TABLE 1

| TARGET SPECIES OF POTENTIAL INTEREST | |
|---|---|
| Primary interest for population reduction/behavior modification | dog |
| | cat |
| | human |
| Primary interest in enhancing quality of meat production | pig |
| | cow |
| Significant interest in population control | horse (control in the USA is federally mandated) |
| | deer |
| | burro |
| | fox |
| | primates |
| | elephants |
| | rodents (e.g., mouse, rat) |
| | rabbit |
| | marsupials |
| Other invasive species | see Cooper and Larsen, 2006 |

In some embodiments, there are different mechanisms of action possible for the immunocontraceptive, including, for example:

1. Inhibition of sperm binding
2. Induction of CDC or ADCC; use of IgM antibodies or effectorized IgG may enhance efficacy at low dose. In some embodiments, one can target male reproductive tract specific glycoform of CD52 (mrtCD52, humans). Other potential targets are the sperm or semen antigens listed in Table 2, antibodies to which, if present in the female reproductive tract, are predicted to prevent fertilization. In some embodiments, alternative target proteins for females include GnRH receptor, LH and LH receptor, FSH and FSH receptor. In some embodiments, alternative targets for males include GnRH receptor, LH and LH receptor, FSH and FSH receptor, and testosterone. In some embodiments, alternative targets for males and females include TMEM95 (*PLoS Genet.* 2014 January; 10(1):e1004044. doi: 10.1371/journal.pgen.1004044. Epub 2014 Jan. 2. A Nonsense Mutation in TMEM95 Encoding a Nondescript Transmembrane Protein Causes Idiopathic Male Subfertility in Cattle. Pausch H1, Kölle S2, Wurmser C1, Schwarzenbacher H3, Emmerling R4, Jansen S1, Trottmann M2, Fuerst C3, Götz KU4, Fries R1.) In some embodiments, any one or more of the target proteins noted below can be used as a target for the present system. For example, antibodies to any one or more of the proteins noted in Table 2 can be employed (for example, expressed within the subject or encoded within a nucleic acid to administer to a subject), for one or more of the methods and/or goals described herein.

TABLE 2

| TARGET PROTEINS | | | |
|---|---|---|---|
| Targeted in Female | Female Reproductive Protein | GnRH | |
| | | FSH | |
| | | LH | |
| | | CG (hCG in human) | |
| | | ZP2 | |
| | | ZP3 | |
| Targeted in Female or Male | Sperm or semen antigen | He-6 | (Davies, B. et al. 2004 *Mol Cell Biol* 24: 8642-8648) |
| | | Crisp-1 | (Roberts, K. P. et al. 2003 *Biol Reprod* 69: 572-581) |
| | | Beta | (Tollner, T. L. et al. 2008 |

TABLE 2-continued

| TARGET PROTEINS | |
|---|---|
| defensins | Hum Reprod 23: 2523-2534; Yudin, A. I. et al. 2003 Biol Reprod 69: 1118-1128) |
| Carbonyl reductase (p34H) | (Boue, F. and Sullivan, R. 1996 Biol Reprod 54: 1018-1024) |
| Catsper1-4 | (Lishko, P. V. et al. 2012 Annual review of physiology 74: 453-475) |
| Catsper beta, gamma and delta | (Lishko, P. V. et al. 2012 Annual review of physiology 74: 453-475) |
| Ksper (slo3) principal K channel of sperm | (Lishko, P. V. et al. 2012 Annual review of physiology 74: 453-475) |
| Eppin | (O'Rand M, G. 2004 Science 306: 1189-1190) |
| Mrtcd52 | (Isojima, S. et al. 1987 Journal of reproductive immunology 10: 67-78) |
| SFEC, also known as AAC4 | (Kim, Y. H. et al. 2007 Dev Biol 302: 463-476) |
| ACTL7a: | (Fu, J. et al. 2012 Fertility and sterility 97: 1226-1233) |
| Zonadhesin | (Herlyn, H. and Zischler, H. 2008 The International journal of developmental biology 52: 781-790) |
| Sp-17 | (Lea, I. A. et al. 1997 Fertility and sterility 67: 355-361) |
| Spam1 | (McLaughlin, E. A. et al. 1997 Molecular human reproduction 3: 801-809) |
| Adam1/2/3 | (Primakoff, P. et al. 1988 Nature 335: 543-546) |
| Ldh-c4 | (Chen, Y. et al. 2008 Science in China Series C, Life sciences/Chinese Academy of Sciences 51: 308-316; Goldberg, E. 1990 Progress in clinical and biological research 344: 49-52) |
| Sp-10 | (Herr, J. C. et al. 1990 Biol Reprod 42: 377-382) |
| Sp-56 | (Bleil, J. D. and Wassarman, P. M. 1990 Proc Natl Acad Sci USA 87: 5563-5567) |
| Fa-1 | (Naz, R. K. and Wolf, D. P. 1994 Journal of reproductive immunology 27: 111-121) |
| Sob-2 | (Lefevre, A. et al. 1997 Molecular human reproduction 3: 507-516) |
| Hspag9 | (Jagadish, N. et al. 2006 Vaccine 24: 3695-3703) |
| Izumo | (An, G. et al. 2009 Am J Reprod Immunol 61: 227-235; Wang, D. G. et al. 2008 Am J Reprod Immunol 59: 225-234; Wang, M. et al. 2009 Molecular reproduction and development 76: 794-801) |
| Rnase10 | (Krutskikh, A. et al. 2012 FASEB J 26: 4198-4209) |
| Tex101 | (Li, W. et al. 2013 Journal of molecular cell biology 5: 345-347) |
| Targeted in male | GnRH mrtCD52 Prostate-specific antigen Testosterone |

In some embodiments, any antibody that can stop, suppress, and/or reduce the ability of an organism to reproduce can be employed in an AAV for a composition or method provided herein. In some embodiments, one or more of the antibodies, or binding fragments thereof, provided herein can be employed. In some embodiments, the antibody can be at least 90% identical to any of the sequences provided herein, including, for example, those in FIG. 9, 10, 11, or 12. In some embodiments, the antibody can comprise one or more of the 6 CDRs in one or more of the constructs provided herein, including, for example, those in FIG. 9, 10, 11, or 12. In some embodiments, any one or more of the antibodies is administered as a nucleic acid sequence, as provided herein.

Antibodies to the above sperm antigens, in addition to GnRH and mrtCD52, may also be used to bring about male infertility as well.

Viral vectors for bringing about immunocontraception have been utilized. However, in all cases, what has been discussed and carried out is the use of a live virus to express an antigen, to which the animal would hopefully express an antibody using the endogenous immune system (McLaughlin, E. A. and Aitken, R. J. 2011 Molecular and cellular endocrinology 335: 78-88; Munks, M. W. 2012 Zuchthygiene 47 (Suppl 4): 223-227).

In the section below several examples of targets for immunocontraceptive antibodies (delivered as nucleic acids) are presented, highlighting what has been achieved, and key reagents generated.

Mammalian oocytes and eggs are surrounded by a glycoprotein matrix known as the zona pellucida (ZP). The ZP is includes of three or four (depending on the species) glycoproteins (ZP1-4) that are synthesized specifically by, and surround the growing oocyte and early embryo. The ZP acts as species-selective binding site for sperm, with this interaction being required for the sperm to ultimately penetrate the ZP and fuse with the egg plasma membrane (reviewed in Avella, M. A. et al. 2013 Molecular human reproduction 19: 279-289). Many studies have shown that vaccination of animals with solubilized zona pellucida or isolated zona proteins results in female infertility (Barfield, J. P. et al. 2006 Contraception 73: 6-22; Gupta, S. K. and Bansal, P. 2010 Reprod Med Biol 9: 61-71; Gupta, S. K. et al. 2011 Journal of reproductive immunology 88: 240-246; Kirkpatrick, J. F. et al. 2009 Journal of reproductive immunology 83: 151-157). Importantly, transient inhibition of fertility or in vitro sperm-egg interactions is also observed when mice or eggs are passively exposed to monoclonal antibodies that bind murine ZP2 or ZP3 (East, I. J. et al. 1985 Dev Biol 109: 268-273; East, I. J. et al. 1984 Dev Biol 104: 49-56). These results demonstrate that antibody-mediated steric occlusion of sperm-ZP binding is sufficient to bring about infertility. Mice have also been generated that carry human ZP3 in place of murine ZP3 (Rankin, T. L. et al. 1998 Development 125: 2415-2424). These mice are fertile because murine sperm are able to productively interact with human ZP3 in the context of a murine egg. Passive immunization of these mice with a monoclonal antibody (H3.1) that binds human, but not murine ZP3 (Rankin, T. L. et al. 1998 Development 125: 2415-2424), results in reversible inhibition of fertility (Greenhouse, S. et al. 1999 *Hum Reprod* 14: 593-600). This result indicates that a monoclonal antibody with the ability to inhibit human fertilization through disruption of sperm-ZP interaction is functional. Because the ZP proteins are not expressed elsewhere in females, and H3.1 acts simply by preventing sperm-zona interaction, H3.1 is predicted to have no effect on other aspects of reproductive physiology.

Between 2-30% of human infertility is associated with the presence of anti-sperm antibodies in one and/or the other partner of an infertile couple (Krause, W. K. H. and Naz, R. K., eds. (2009) in *Immune Infertility* (Berlin, Germany: Springer-Verlag)). In most cases the relevant antibodies and their targets have not been identified. However, in a series of studies Isojima and colleagues characterized an antisperm activity present in infertile women (Isojima, S. et al. 1968 *Am J Obstet Gynecol* 101: 677-683; Isojima, S. et al. 1972 *Am J Obstet Gynecol* 112: 199-207), and ultimately isolated an IgM monoclonal antibody known as H6-C34, from the peripheral blood lymphocytes of one individual (Isojima, S. et al. 1987 *Journal of reproductive immunology* 10: 67-78). H6-C34 has potent sperm immobilizing and agglutinating activity, suggesting it as the cause of infertility. A number of observations indicate that the H6-C34 target, and that of mouse monoclonal antibody known as S19 (Diekman, A. B. et al. 1999 *FASEB J* 13: 1303-1313), isolated independently, which also has sperm agglutinating activity, is a carbohydrate epitope unique to a male-reproductive tract glycoform of the GPI-linked glycoprotein CD52 (mrtCD52)(Diekman, A. B. et al. 1999 *Immunological reviews* 171: 203-211). mrtCD52 becomes associated with developing sperm as they move through the epididymous (Kirchhoff, C. and Hale, G. 1996 *Molecular human reproduction* 2: 177-184). These observations indicate that H6-C34 constitutes a fully human contraceptive antibody, inhibiting fertilization through sperm agglutination and inhibition of motility in the female reproductive tract. H6-C34 cross-reactive epitope are not present on sperm of non-human primates, making it inconvenient to carry out animal studies. That said, the fact that H6-C34 was isolated directly from an otherwise healthy human indicates it is likely to be safe. Passive immunization with recombinant antibody would provide a method for testing short-term efficacy and safety. H6-3C4 could also be used as a contraceptive by men, acting as it does in females, to bind sperm, resulting in a loss of sperm motility and/or sperm agglutination. This also could be tested through passive immunization of volunteers. H6-3C4 sequences have been cloned, expressed as IgG1, and shown to be functional in sperm agglutination in vitro (Komori, S. et al. 1988 *Clinical and experimental immunology* 71: 508-516; Sawai, H. et al. 1995 *Am J Reprod Immunol* 34: 26-34; Yamasaki, N. et al. 1987 *Molecular immunology* 24: 981-985).

Chorionic gonadotropin is a heterodimer. Its alpha chain is shared with that of LH, FSH and TSH, while the beta subunit is specific to hCG. In healthy individuals (hCG is ectopically expressed in many cancers) hCG is only expressed by the developing embryo and by endometreal cells during the luteal phase. Both promote embryo development. In particular, expression of hCG in the embryo begins soon after fertilization and is required for implantation in the uterus. Thus, vaccination of marmosets with hCG results in the creation of anti-hCG antibodies, which result in embryo loss at a very early stage of development (Hearn, J. P. 1976 *Proc R Soc Lond B Biol Sci* 195: 149-160). Similar effects in humans are suggested by observations in an Indian phase II clinical trial in the 1990s, in which almost all women vaccinated against hCG failed to become pregnant so long as anti-hCG antibody titers remained above a critical threshold of 50 ng/ml (Talwar, G. P. et al. 1994 *Proc Natl Acad Sci USA* 91: 8532-8536; Talwar, G. P. et al. 1997 *Am J Reprod Immunol* 37: 153-160). In all other respects, the reproductive systems of these women behaved normally. However, while all women vaccinated generated antibodies to hCG, only 80% generated titers greater than 50 ng/ml. Generation of these titers also required multiple boosts, over a three month period. Finally, once super-threshold antibody titers were achieved, they dropped over time, with booster injections being provided every three months in order to maintain antibody titers above the 50 ng/ml threshold (Singh, M. et al. 1998 *Am J Reprod Immunol* 39: 395-398; Talwar, G. P. et al. 1994 *Proc Natl Acad Sci USA* 91: 8532-8536). According to (Ferro and Garside, 2011) work by the Indian group (G. P Talwar National Institute of Immunology, India), ceased following these phase II trials. It was supported in part by a US biotech company, Aphton, which no longer exists. Talwar (Talwar, G. P. et al. 2009 *Journal of reproductive immunology* 83: 158-163) claims that the US/India plan was re-initiated in 2009. A recent review suggests a new hCG vaccine has been developed and is being pursued (Talwar, G. P. 2013 *Ann N Y Acad Sci* 1283: 50-56), though no in vivo data are provided.

Anti-hCG monoclonal antibodies able to neutralize hCG function have been generated by multiple groups. Those whose sequences have been published include the following: (WO 2005095458 A1; Majumdar, R. et al. 2011 Proteins 79: 3108-3122)(WO2005095458 A1, PCT/IN2005/000100). Several of these were generated using human scFV libraries. Thus, to some extent they have been humanized.

Other developments include the development of new hCG-carrier complexes designed to act as inducers of antibody responses (adjuvants) for contraception (Hao, M. et al. 2004 *Journal of reproductive immunology* 63: 123-135; US 2005/0032171).

Gonadotrophin releasing hormone 1 (GnRH1, also known as Leutinizing hormone releasing hormone, LHRH; GnRH; luliberin; gonadoliberin) is a master regulator of reproductive biology in males and females. It orchestrates sexual development of immature animals and is also required for maintaining normal reproductive function in the adult. GnRH1 is synthesized as a precursor in neurons of the hypothalamus. The mature decapaptide is released from terminals of these neurons in the median eminence, from which it diffuses into the portal capillary system. These capillaries pass from the hypothalamus to the anterior pituitary, where GnRH1 stimulates the release of LH and FSH from gonadotropes into the general circulation. LH and FSH are required for male and female reproductive development and function in a number of ways. GnRH1 is also required for many reproductive behaviors. Interestingly, while LH and FSH protein sequences show typical evolutionary divergence, mature GnRH1 is (with the exception of the guinea pig), identical in all mammals sequenced thus far. While receptors sensitive to GnRH1 exist outside the pituitary in peripheral tissues, it is likely that these normally respond to other related GnRH peptides (GnRHII and GnRHIII) produced peripherally, since GnRH1 has a very short half-life and is only produced by the hypothalamus. In consequence, molecules that silence GnRH1 function have long been seen as a very specific method for inhibiting reproductive behaviors and fertility in a number of mammals.

Many kinds of mammals have been vaccinated against GnRH so as to bring about infertility and/or behavior modification. Early examples include sheep (Clarke, I. J. et al. 1978 *The Journal of endocrinology* 78: 39-47; Jeffcoate, I. A. et al. 1978 *Theriogenology* 10: 323-335), cattle (Robertson, I. S. et al. 1982 *The Veterinary record* 111: 529-531; Robertson, I. S. et al. 1979 *The Veterinary record* 105: 556-557; Robertson, I. S. et al. 1981 *The Veterinary record* 108: 381-382), rats (Fraser, H. M. and Baker, T. G. 1978 *The Journal of endocrinology* 77: 85-93; Fraser, H. M. and Gunn, A. 1973 *Nature* 244: 160-161; Fraser, H. M. et al. 1974 *The Journal of endocrinology* 63: 399-406; Fraser, H. M. and Sandow, J. 1977 *The Journal of endocrinology* 74: 291-296; Takahashi, M. et al. 1978 *Biol Reprod* 18: 754-761), rabbits (Arimura, A. et al. 1973 *Endocrinology* 93: 1092-1103; Fraser, H. M. and Gunn, A. 1973 *Nature* 244: 160-161; Jeffcoate, S. L. et al. 1974 *Immunochemistry* 11: 75-77), and primates (Hodges, J. K. and Hearn, J. P. 1977 *Nature* 265: 746-748). Human males have also been vaccinated against GnRH in prostate cancer trials (Talwar, G. P. 1997 *Human reproduction update* 3: 301-310).

More recently active immunization against GnRH has been used to bring about infertility in many species, including, dogs (Gupta, S. K. et al. 2011 *Am J Reprod Immunol* 66: 51-62; Walker, J. et al. 2007 *Vaccine* 25: 7111-7119), cats (Levy, J. K. 2011 *Am J Reprod Immunol* 66: 63-70; Levy, J. K. et al. 2011 *Theriogenology* 76: 1517-1525), deer and elk (Powers, J. G. et al. 2011 *Biol Reprod* 85: 1152-1160), elephant (Benavides Valades, G. et al. 2012 *Reproductive biology and endocrinology* 10: 63; De Nys, H. M. et al. 2010 *Journal of the South African Veterinary Association* 81: 8-15; Druce, H. C. et al. 2011 *PLoS One* 6: e27952).

Importantly, passive immunization with anti-GnRH antibodies generated in other organisms inhibits fertility or expression of hormones required for fertility, thereby demonstrating that antibodies are the relevant component required for inhibition of fertility. Examples include ferret (Gledhill, B. et al. 1982 *J Reprod Fertil* 64: 19-23), rat (Koch, Y. et al. 1973 *Biochem Biophys Res Commun* 55: 623-629), hamster (de la Cruz, A. et al. 1976 *Endocrinology* 98: 490-497), ram (Lincoln, G. A. and Fraser, H. M. 1979 *Biol Reprod* 21: 1239-1245), primate (McCormack, J. T. et al. 1977 *Endocrinology* 100: 663-667), marsupial (Short, R. V. et al. 1985 *J Reprod Fertil* 75: 567-575). In addition, in 1988 Silversides showed that passive infusion of a mouse monoclonal antibody resulted in infertility in female rats and altered cycling in the female dog (Silversides, D. W. et al. 1985 *Journal of reproductive immunology* 7: 171-184).

Recent efforts to make anti-GnRH approaches to immunocontraception work better involve development of novel ways of presenting GnRH to the immune system. Examples include display on phage (Samoylov, A. et al. 2012 *Zuchthygiene* 47 (Suppl 6): 406-411) and presentation in the context of a live virus (Munks, M. W. 2012 *Zuchthygiene* 47 (Suppl 4): 223-227; U.S. Pat. Nos. 6,013,770, 6,284,733).

Possible uses of monoclonal antibodies for one or more of the above target molecules, introduced through passive immunization, are outlined in (Van Der Lende, T. 1994 *Biotechnology advances* 12: 71-87).

In some embodiments, reproduction and reproduction-associated behaviors can be targeted for inhibition at a number of points.

In some embodiments, reproduction can be targeted more generally (rather than the specific targets noted above). Reproduction requires the careful orchestration of many different variables: the production, action and regulation of multiple hormones, gamete production, fusion of sperm and egg, and maintenance of pregnancy. Each of the molecules involved in these processes identifies a possible point at which to intervene, and thereby inhibit fertility. Points of intervention can be divided into three broad categories: those that interfere with gamete production, those that interfere with gamete function, including fertilization, and those that interfere with embryonic development. Molecules of greatest interest for targeting (that is, for the creation of nucleic acid sequences that encode for antibodies that block the function of the molecule) are those that are required for reproduction, but not for any other physiological process. In some embodiments, they are extracellular and thus available for antibody binding.

In some embodiments, immunocontraception (also known as immunocastration) can also be used in agriculture to increase the quantity and quality of meat, to alter behavior, to increase efficiency of feed use, and to prevent feedlot pregnancy (Thompson, D. L. 2000. *Animal reproduction science* 60-61: 459-469). Organisms of interest include pigs (Aluwe, M. et al. 2013 *Meat science* 94: 402-407; Bonneau, M. et al. 1994 *Journal of animal science* 72: 14-20; Meloen, R. H. et al. 1994 *Vaccine* 12: 741-746); bulls (Amatayakul-Chantler, S. et al. 2013 *Meat science* 95: 78-84; D'Occhio et al. 2001 *Animal reproduction science* 66: 47-58; Price, E. O. et al. 2003 *Journal of animal science* 81: 411-415), as well as sheep and goats (Thompson, D. L. 2000. *Animal reproduction science* 60-61: 459-469). Immunocastration is also seen in much of Europe as a desirable alternative (from an animal welfare perspective) to castration, which is carried out for all pigs and many cows (Heid, A. and Hamm, U. 2013 *Meat science* 95: 203-211).

In some embodiments, mouse anti-human ZP3: (East et al., 1985; East et al., 1984), can be introduced into a vector such as AAV and delivered through IM injection. A humanized version of the constant region could be generated by simply replacing the mouse constant regions with those of human IgG1. In some embodiments, the sequence is that depicted in FIG. 12.

In some embodiments, human anti-human hCG: (Kabeer et al., 2005; Majumdar et al., 2011), can be introduced into a vector such as AAV and delivered through IM injection. In some embodiments, the construct can include modifications that can minimize off-target effects involve eliminating effector function from the heavy chain constant region. In some embodiments, the sequence is that depicted in FIG. 11.

In some embodiments the E12 anti-hCG antibody can be introduced into a vector such as AAV and delivered through IM injection (see, e.g., Gadkari, R. A., Sandhya, S., Sowdhamini, R., and Dighe, R. R. (2007). The antigen binding sites of various hCG monoclonal antibodies show homology to different domains of LH receptor. Molecular and cellular endocrinology 260-262, 23-32; and Majumdar, R., Railkar, R., and Dighe, R. R. (2011). Docking and free energy simulations to predict conformational domains involved in hCG-LH receptor interactions using recombinant antibodies. Proteins 79, 3108-3122.) In some embodiments, the construct can include modifications that can minimize off-target effects involve eliminating effector function from the heavy chain constant region. In some embodiments, the sequence is that depicted in FIG. 12.

In some embodiments, any construct that demonstrates in vitro sperm agglutinating activity can be employed. In some embodiments, one can use human anti-human mrtCD52 introduced into a vector such as AAV, delivered through IM injection. Possible modifications that minimize off-target effects involve use of different IgG isotypes, such as IgG1 or IgG3. In particular, IgG3 has an increased ability to bring about complement activation, which is at least in part how this antibody causes sperm agglutination (Isojima et al., 1987; Komori et al., 1988; Sawai et al., 1995; Yamasaki et al., 1987)

In some embodiments, any of the genetic constructs and/or immunocontraception molecules provided herein (including molecules encoding said immonucontraception molecules) can be incorporated into a transfection vehicle.

In some embodiments, the construct is configured to allow for transient expression of the immunocontraception molecule.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments.

Example 1

Antibody Binding

The immunocontraception molecules (antibodies HB-9094 and SMI41) were expressed in HEK 293T cells. Purified epitope protein was tested for binding to GnRH protein (FIGS. 1A, 1B, 2A, and 2B.) Surface plasmon resonance (SPR) based technology was used to study biomolecular interactions between the expressed antibody epitopes and GnRH protein in real time.

Figure 1B:
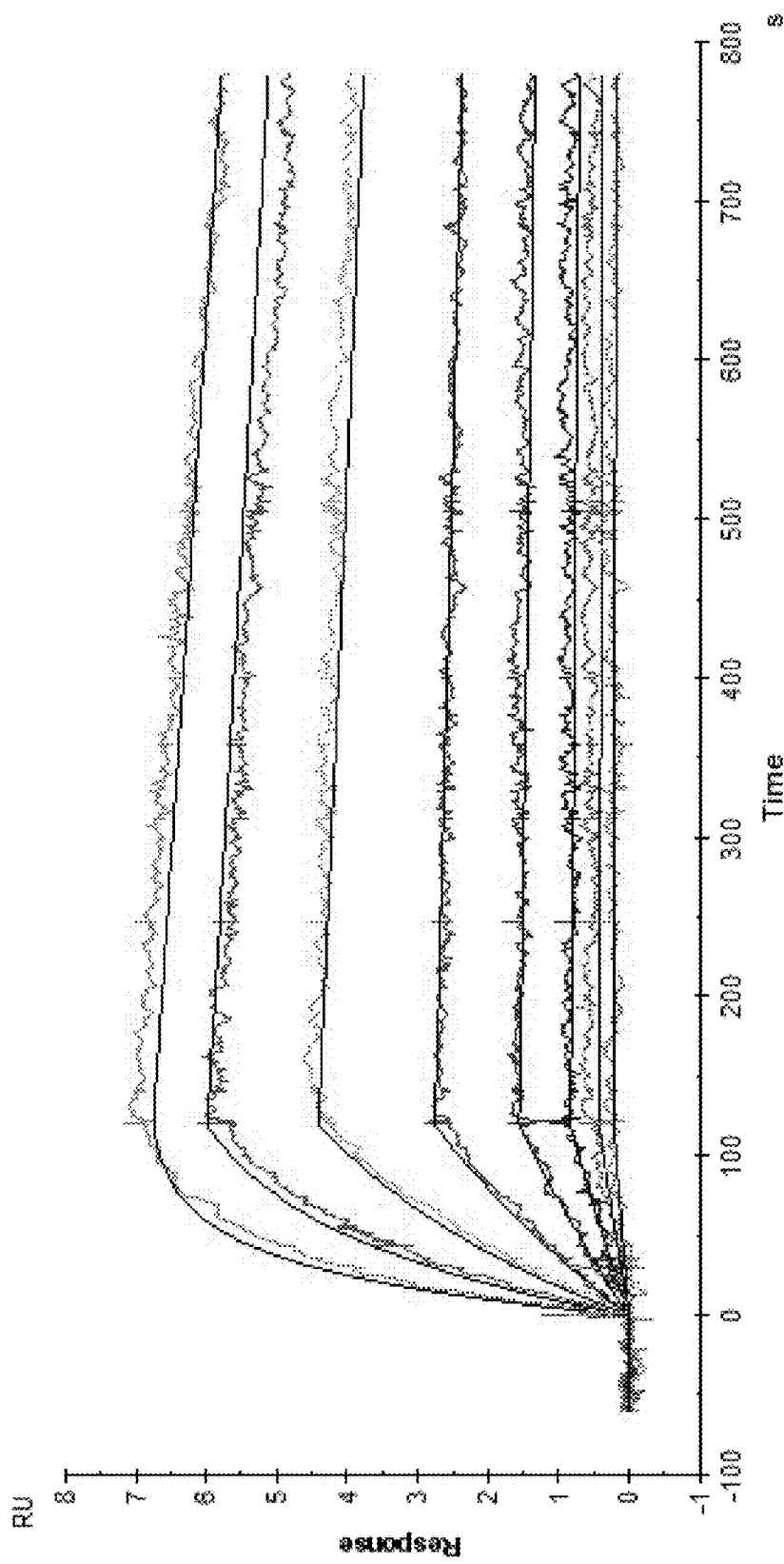
Figure 2A:
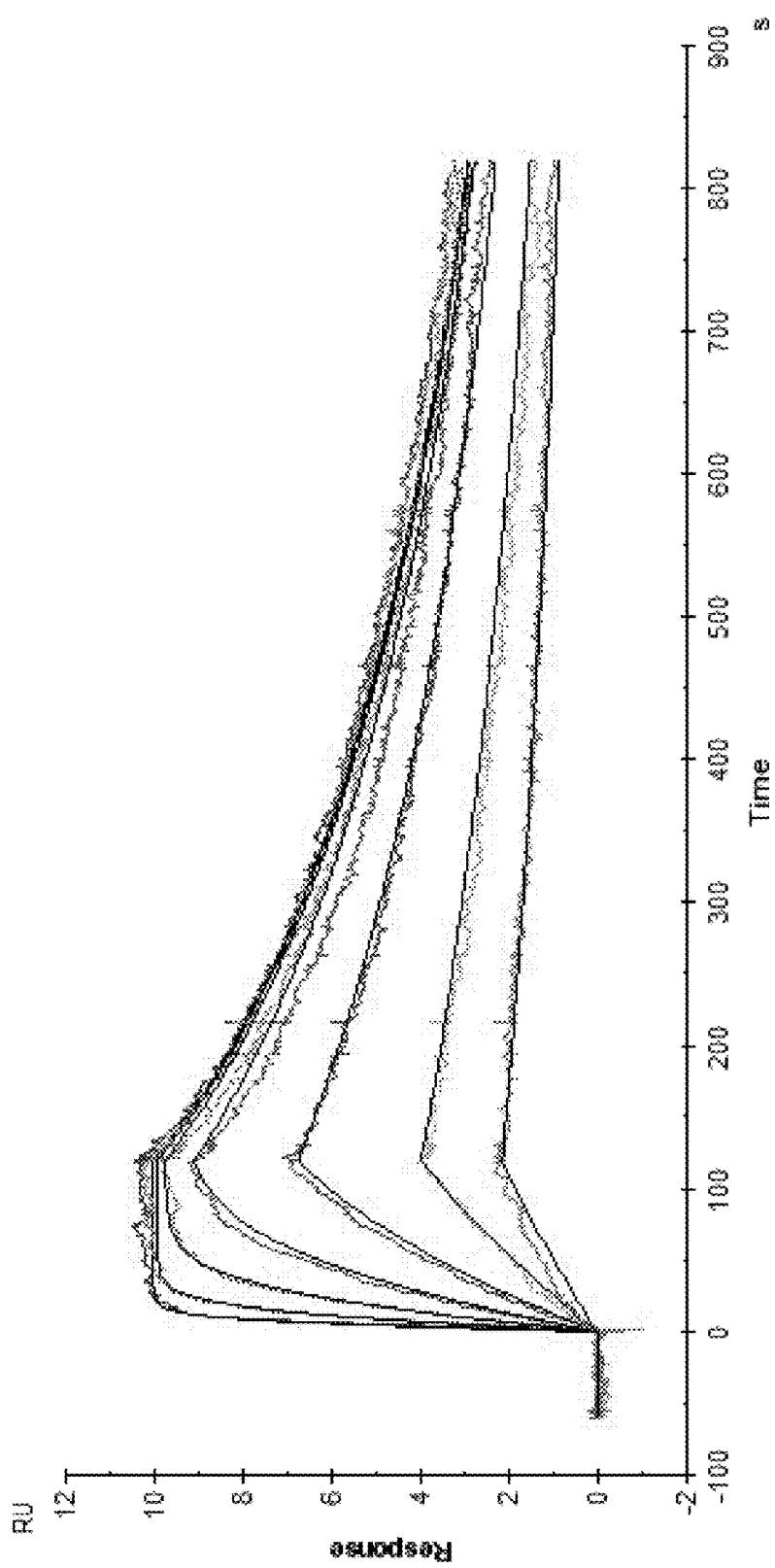
FIGS. 2A and 2B depict the binding affinity of SMI41-HEK293T-IgG. Surface plasmon resonance binding data for cloned antibody expressed in HEK 293T cells (A), and original monoclonal antibody (B).
Figure 2B:
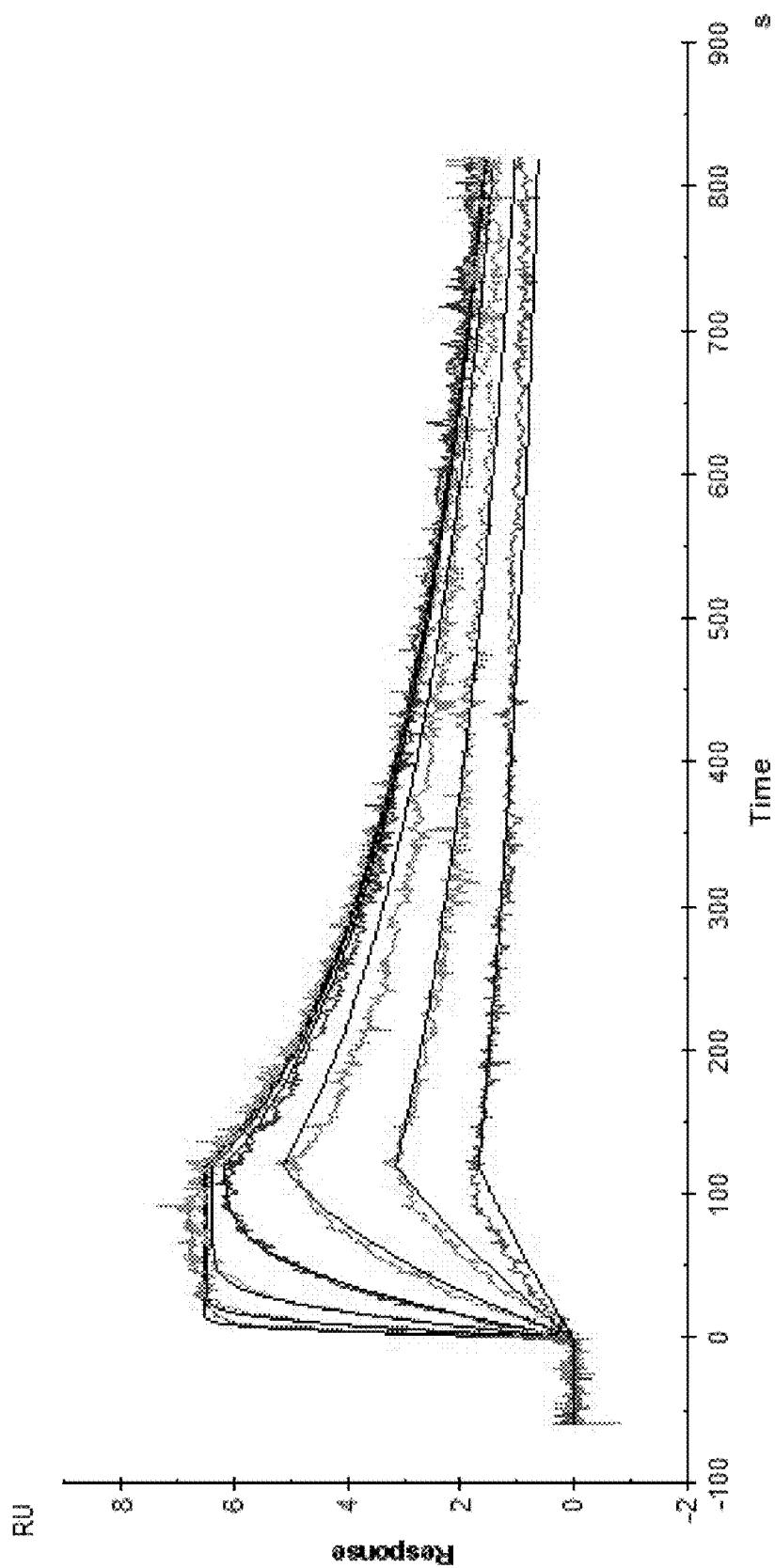

Referring to FIGS. 1A and 1B, the expressed HB-9094-HEK293T-IgG construct (1A) showed a binding affinity very similar to the binding affinity of the original HB-9094 monoclonal antibody (1B). Indeed the $K_D$ of HEK293T-IgG was $9.18*10^{-10}$M, the $k_a$ was $2.715*10^5$/Ms, and the $k_d$ was $2.494*10^{-4}$/s, while the $K_D$ of the original HB9094 hybridoma IgG was $8.753*10^{-10}$M, the $k_a$ was $2.697*10^5$/Ms, and the $k_d$ was $2.361*10^{-4}$/s.

Similarly, referring to FIG. 2, the expressed SMI41-HEK293T-IgG construct (panel A) showed a binding affinity very similar to the binding affinity of the original SMI-41 monoclonal antibody (panel B). Indeed the $K_D$ of SMI41-HEK293T-IgG was $5.920*10^{-10}$M, the $k_a$ was $4.760*10^6$/Ms, and the $k_d$ was $2.818*10^{-3}$/s, while the $K_D$ of SMI41 ascites IgG was $8.19*10^{-10}$M, the $k_a$ was $8.993*10^6$/Ms, and the $k_d$ was $4.674*10^{-3}$/s.

Example 2

Isolation of Monoclonal Antibodies

Two anti-GnRH1 monoclonal antibodies, HB9094, (Silversides et al., 1985) and SMI41 (Covance) were cloned.

In the case of HB9094 the hybridoma expressing the anti-GnRH antibody was acquired from ATCC. It was then cultured in standard media to allow for expression of the heavy and light chains, and their purification from cell culture media using protein G. Two methods to clone the genes encoding antibody heavy and light chains were used. In the first, mass spectrometry was used on the purified antibody derived from the cell culture supernatant. This identified a number of peptide fragments that were identical or similar to other sequences in the NCBI database. For the second mRNA were isolated from these cells and used to carry out RNA-seq to provide the transcriptome of the hybridoma. The RNA-seq raw reads were assembled into transcription units using standard procedures. These were then blasted using mouse immunoglobulin constant region sequences to identify those transcripts likely to be encoding immunoglobulin heavy or light chains. These putative immunoglobulin sequences were then fed into the database used for analysis of mass spectrometry as predicted proteins. The mass spectrometry data from HB9094 was then blasted against these new predicted protein sequences and perfect matches were identified.

From a combination of the above procedures—RNA-seq and mass spectrometry—consensus protein sequences were arrived at for both heavy and light chains. This was used to synthesize DNA designed to encode these heavy and light chains protein sequences. The sequences are shown in FIG. 9.

The sequences were cloned into vectors from Invivogen (pFUSE2ss-CLIg-mk for the light chain; pFUSEss-CHIg-mG1 for the heavy chain) that allow expression of secreted versions of antibody heavy and light chains.

These plasmids were transfected into 293 cells and secreted antibody isolated using protein G affinity columns.

For SMI41 mass spectrometry analysis was carried out on antibody purified using protein G, from ascites provided by Covance. This identified a number of sequence hits in the NCBI protein database. However, there were a number of gaps. To fill these, an aliquot of the ascites provided by Covance were taken, isolated genomic DNA was obtained, and PCR was carried out using degenerate primers expected to amplify rearranged heavy or light chain variable regions. PCR products from the above reactions were sequenced and translated into potential coding sequences. These were then fed back into the database used for analysis of mass spectrometry data and perfect matches identified. As above, these resulted in perfect matches between the DNA and mass spec peptide data. DNA sequences designed to encode these sequences were synthesized, inserted into Invivogen vectors, and expressed as above. Secreted antibody was isolated using protein G. The sequence is shown in FIG. 10

Example 3

Antibody Binding

Figure 3:
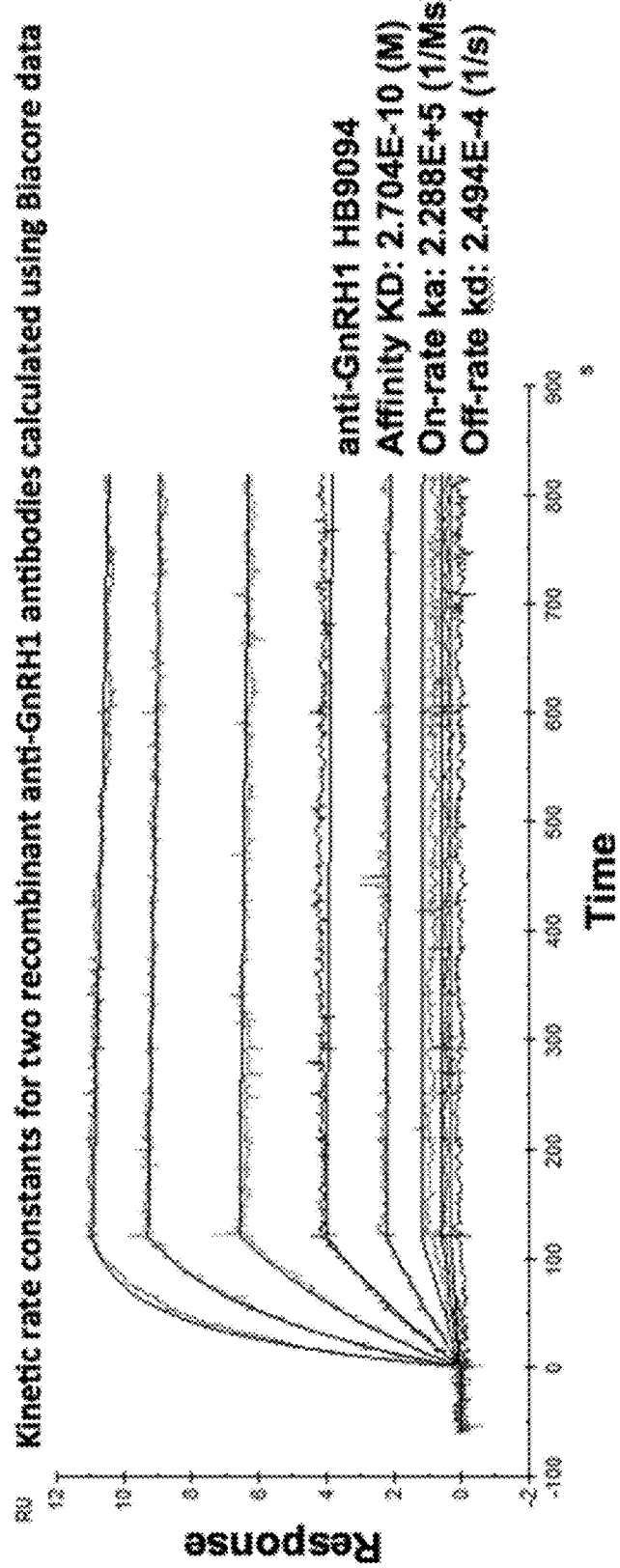
FIG. 3 depicts the binding curves for a recombinant anti GnRH1 antibody.
Figure 4:
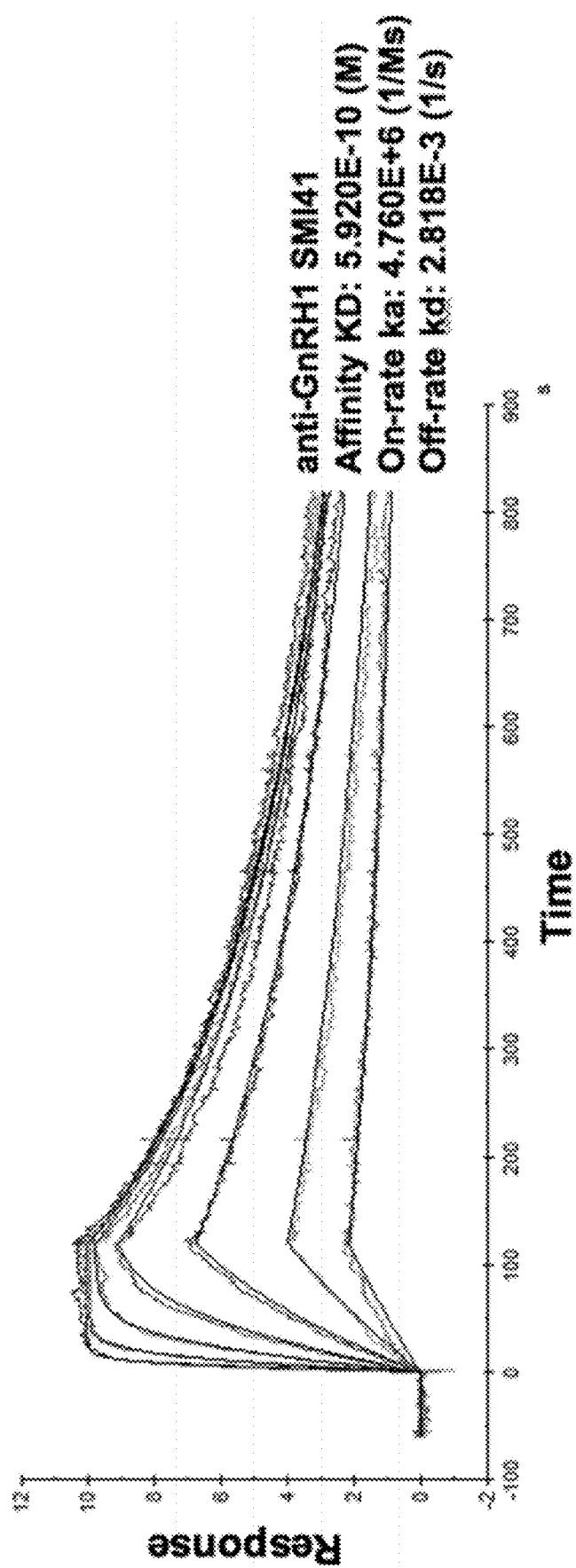
FIG. 4 depicts the binding curves for a recombinant anti GnRH1 antibody.

Both recombinant immunoglobulins were characterized for GnRH1 binding using the biacore system. Goat anti-mouse IgG (H+L) was immobilized to the CM5 chip surface using an amine coupling kit. In brief, N-hydroxysuccinimide (NHS) and 1-ethyl-3-(3-dimethylaminopropyl)carbodiimide hydrochloride (EDC) were mixed and pumped across the chip to activate the carboxymethyl-dextran surface. 1 uM Goat anti-mouse IgG in 10 mM acetate buffer pH5 was injected over the chip surface at the flow rate of 1 ul/min for 420 s. Ethanolamine was then injected to block the remaining activated NHS-ester groups on the sensor chip. Kinetic measurements were performed with constant flow of HBS-EP+ buffer, which also served as the diluent for Abs and GnRH. One cycle of Ab-GnRH binding begins with the injection of 50 nM anti-GnRH Ab1 or 200 nM anti-GnRH Ab 2 over the chip surface at the rate of 5 ul/min for 80 s, followed by injection of GnRH at a series of 2-fold dilutions, beginning at 1024 nM. The chip surface was then regenerated by three X injection of 10 mM Glycine Ph 1.5 at a rate of 30 ul/min for 30 s before the next cycle. The surface response on the chip was recorded by a Biacore T200. Kinetics and affinity analysis was performed by the Biacore T200 evaluation software. Kinetic rate constants determined from this data are plotted in FIGS. 3 and 4. For HB9094, the affinity $K_D$ was $2.7*10^{-10}$(M), the $k_{on}$ was $2.288*10^5$ (1/Ms), and the $k_{off}$ was $2.494*10^{-4}$ (1/s). For SMI41, the affinity $K_D$ was $5.920*10^{-10}$(M), the $k_{on}$ was $4.760*10^6$ (1/Ms), and the $k_{off}$ was $2.818*10^{-3}$ (1/s). One cycle of Ab-GnRH binding began with the injection of 50 nM anti-GnRH Ab1 or 200 nM anti-GnRH Ab2 over a chip surface bound with goat anti-mouse IgG at the rate of 5 ul/min for 80 s, followed by injection of GnRH at a series of 2-fold dilutions, beginning at 1024 nM. The chip surface was then regenerated by three X injection of Glycine pH1.5 at a rate of 30 ul/min for 30 s before the next cycle. The surface response on the chip was recorded by Bicore T200. Kinetics and affinity analysis was performed by the Biaore T200 evaluation software.

Example 4

Recombinant AAV Vector Production

Genes encoding both antibodies were introduced into an AAV2/8 vector developed in David Baltimore's lab (illustrated for anti-GnRH1 antibody SMI41 in FIG. 5) (see also, Balazs, A. B., Chen, J., Hong, C. M., Rao, D. S., Yang, L., and Baltimore, D. (2012). Antibody-based protection against HIV infection by vectored immunoprophylaxis. Nature 481, 81-84). Nucleotide sequences for the encoded heavy and light chains, signal sequences, and protease cleavage sites used to separate heavy and light chains post protein synthesis, are provided below.

To generate virus, 293T cells were seeded in 15 cm plates at $3.75 \times 10^{\wedge}6$ cells per plate in 25 ml DMEM medium supplemented with 10% fetal bovine serum, 1% penicillin-streptomycin mix and 1% glutamine in a 5% CO2 incubator at 37° C. After three days culture, media was changed to 15 ml of fresh media and two hours later, the AAV backbone vector, which contained either anti-GnRH Ab-encoding genes or luciferase, was co-transfected with helper vectors pHELP (Applied Viromics) and pAAV 2/8 SEED (University of Pennsylvania Vector Core) at a ratio of 1:4:8 using BioT transfection reagent (Bioland Scientific). AAV virus was then collected from culture supernatant at 36, 48, 72, 96 and 120 h after transfection and these fractions pooled.

A first virus batch was purified by filtering the virus culture supernatant through a 0.2 mm filter, followed by centrifugation at 110,527 g for 1.5 h. The virus pellet was dissolved in DMEM and stored at −80° C. The second virus batch was obtained from the supernatant after spinning. PEG solution (40% polyethylene glycol in 2.5M NaCl) was added to the supernatant at a volume ratio of 1:4, and gently mixed at 4° C. overnight to precipitate virus. Precipitated virus was pelleted at 4,000 g for 30 min and re-suspended in 10 ml MEM. To remove PEG residue and concentrate, the virus, this solution was loaded onto 100 kDa MWCO centrifugal filters (Millipore) and spun at 3220 g at 4° C. until ~1 ml retentate remained. Fresh MEM was added to the filter and this process was repeated three times. Final virus solution was about 2 ml total and stored at −80° C. Biacore experiments (not shown) confirmed that antibodies expressed in this AAV format still bind GnRH1 with high affinity.

Example 5

AAV-Dependent Anti-GnRH Antibody Production

Figure 6:
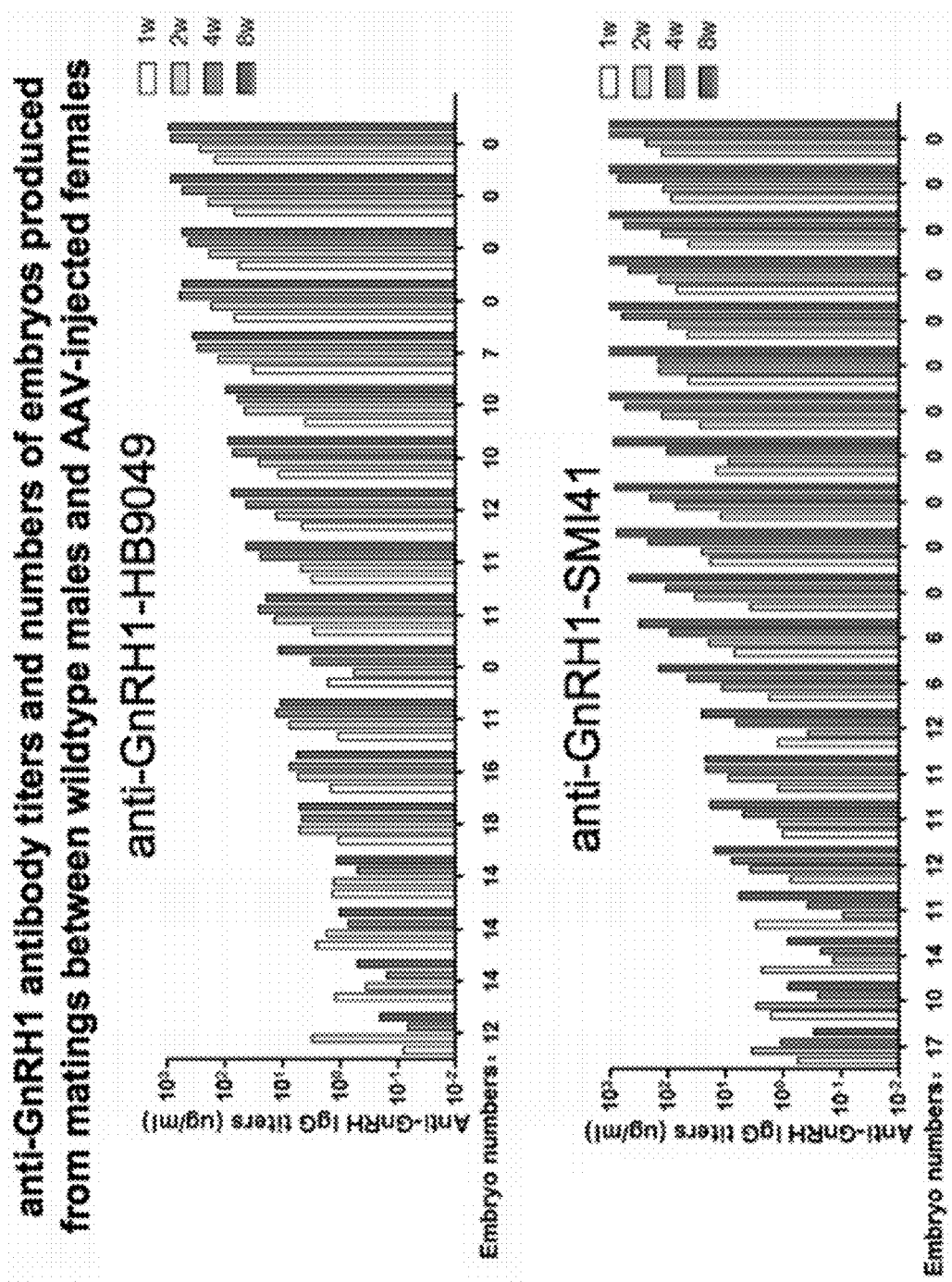
FIG. 6 is a graph depicting the results of GnRH1 antibody expression in females and the results of mating experiments.
Figure 7:
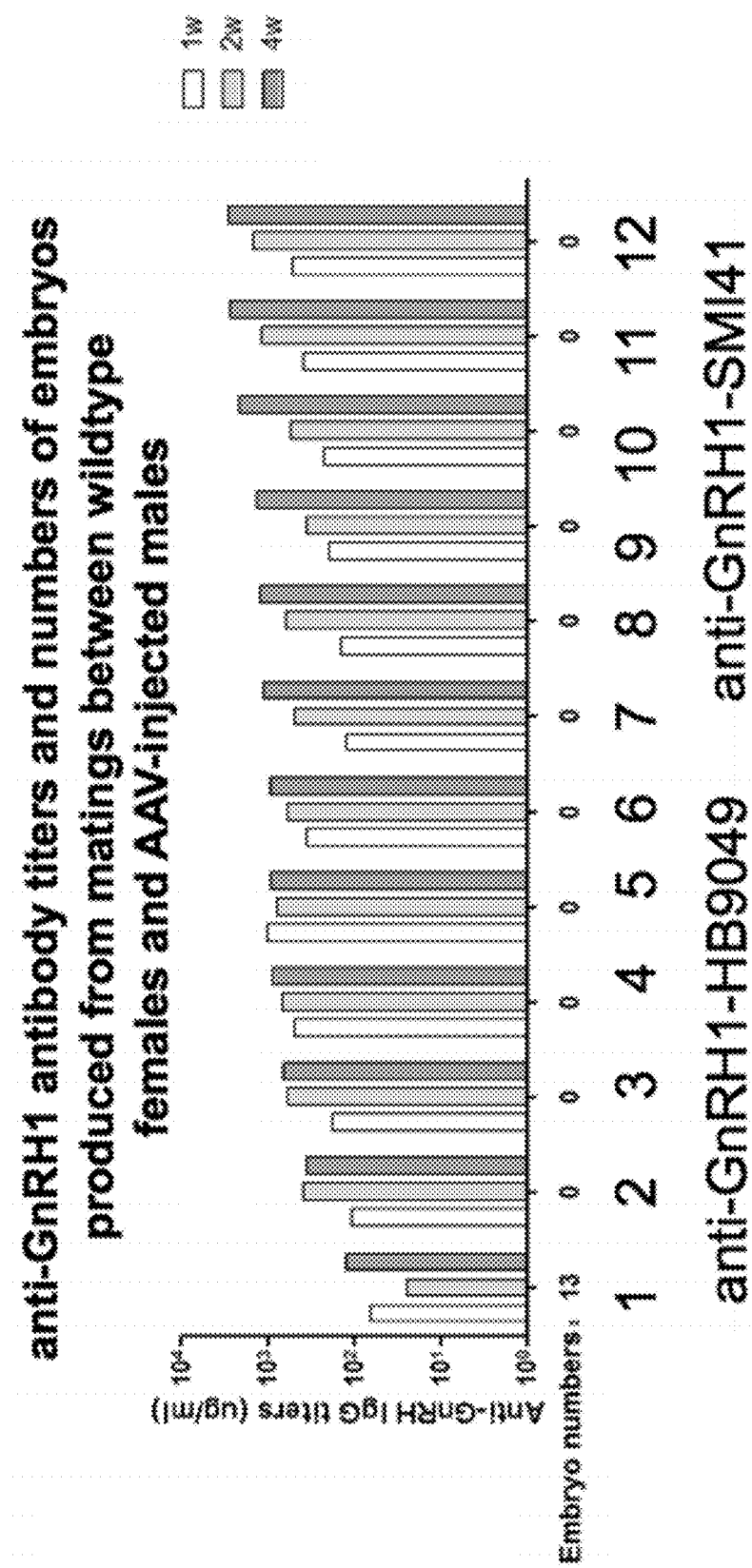
FIG. 7 is a graph depicting the results of GnRH1 antibody expression in males and the results of mating experiments.

Mice were anesthetized and injected with 50 microliters of viral particles, at several different dilutions. Mice were anesthetized and injected with a range of virus particle numbers, which resulted mice expressing a range of anti-GnRH1 antibody concentrations. Antibody titers determined by ELISA are indicated at different time points by vertical bars in FIG. 6 for females, and FIG. 7, for males.

The ELISA assay used to determine anti-GnRH1 antibody concentrations in serum was as follows: 96 well plates were allowed to bind streptavidin at a concentration of 100 ng/well, in carbonate buffer pH 9.6, at room temperature for 3 h. Plates were then washed 3 times with PBST. Biotin-GnRH1 in PBS was added to plates at a concentration of 175 nmole/well and the plates were incubated at 4° C. overnight. Following this incubation plates were washed again to remove unbound biotin-GnRH1. 200 ul of 1% BSA in PBS was then added to all wells as a blocking solution to prevent non-specific binding of antibodies to the plates. After several washes, serum samples and IgG standards at known concentrations (recombinant anti-GnRH SMI41 and anti-GnRH1-HB9094) were diluted in 1% BSA-PBST and incubated in wells (60 ul/well) for 2 h. After washing, Peroxidase labeled goat anti-mouse IgG (H+L) was diluted 1:20000 in 1% BSA-PBST and incubated into each well at 100 ul/well for 30 min. Plates were then washed 4 times with PBST. Finally, the enzyme substrate Amplex® UltraRed Reagent (Invitrogen) was added to plates at 100 ul/well for 15 min. Amplex® Red/UltraRed Stop Reagent was then added to the plates at 20 ul/well to stop the reaction and stabilize the fluorescent signal. Plates were read at 540/590 nm using a Thermo Max Microplate Reader (Bio-Tek).

Fertility experiments: females. Females injected with AAV expressing Anti-GnRH1 HB9094 (FIG. 6, upper panel), and AAV expressing anti-GnRH1 SMI41 (FIG. 6, lower panel) were characterized. These were compared with females that had been injected at the same time with AAV expressing luciferase as a control. Each female was placed into a cage with a male in the afternoon. The next morning females were examined for the presence of mating plugs. Males were separated from females for the bulk of the day and then reintroduced to them in the late afternoon. Introductions were made each weekday, with males and females being kept separate on weekends. Mating plugs were found in all luciferase females, and they became pregnant. Mating plugs were found in a number of the low titer females, and all of these mice became pregnant. Pregnant females were euthanized after two weeks and the number of developing embryos counted. These numbers are indicated at the bottom of each panel, for each female. Females expressing higher titers of anti-GnRH1 antibody were not mated (as evidenced by the lack of mating plugs), and did not become pregnant. This is indicated by a zero in the embryo number row. For both antibodies there is a clear trend towards animals with higher antibody titers having fewer embryos. Once a threshold titer is reached the animals do not mate and therefore do not become pregnant. Females that have failed to mate have been with males now for ~3 months, and we continue to monitor them.

Fertility experiments: males. Six males injected with AAV expressing Anti-GnRH1-HB9094 (FIG. 7, #s 1-6) and AAV expressing anti-GnRH1-SMI41 (FIG. 7, #s 7-12) were characterized. All but one of the animals had high titers of anti-GnrH1 antibodies in serum. Two non-AAV-injected females were introduced into each male cage and cages were characterized for three weeks. Subsequently, new females were rotated into the male cages. The results of these introductions were compared similar experiments involving AAV-luciferase injected males. All anti-GnRH1-expressing males other than #1 showed no behavioral interest in mating (mounting behavior), and no females have become pregnant as determined through visual inspection (3 months). Male #1 mated and produced 13 progeny. All AAV-luciferase males showed immediate interest in mating, and introduced females became pregnant. We continue to monitor the cages for pregnant females.

Range of Ab on Rates

The value of using an anti-GnRH1 antibody with a fast on-rate can be understood by looking more closely at the biology of GnRH1 secretion and transport to its site of action. GnRH1 is synthesized as a precursor in neurons of the hypothalamus. The mature decapaptide is released from terminals of these neurons into the median eminence, from which it diffuses into the portal capillary system. These capillaries pass from the hypothalamus to the very nearby anterior pituitary, where GnRH1 stimulates the release of LH and FSH from gonadotropes into the general circulation. Inhibiting GnRH1 is challenging because GnRH1 is secreted and acts within a very local environment. The plasma GnRH1 is irrelevant because GnRH1 has a very short half-life, and is diluted to physiologically insignificant levels in the general circulation. Therefore, anti-GnRH1 antibodies must be at a high concentration in the portal capillary circulation, and act quickly, before GnRH1 moves the very short distance to the pituitary. Direct measurements of GnRH1 and LH in portal plasma in the ewe (where measurements of this sort can be made because of the animals large size) show a delay between GnRH1 and LH pulses of 1.26+/−0.43 minutes (Midgley Jr. A. R., et al. 1997 *Endocrine* 6: 133-143) In short, anti-GnRH1 antibodies need to inactivate the bulk of secreted GnRH1 in probably less than a minute in order to inhibit LH/FSH release. An important variable in terms of enhancing inactivation of GnRH1 is therefore the antibody on-rate (the rate of GnRH1 binding). Without intending to be limited by theory, the off-rate is less relevant since once GnRH1 enters the general circulation it is diluted enormously and rapidly degraded.

Example 6

Range of Ab on Rates

Figures 8A, 8B, 8C, 8D:
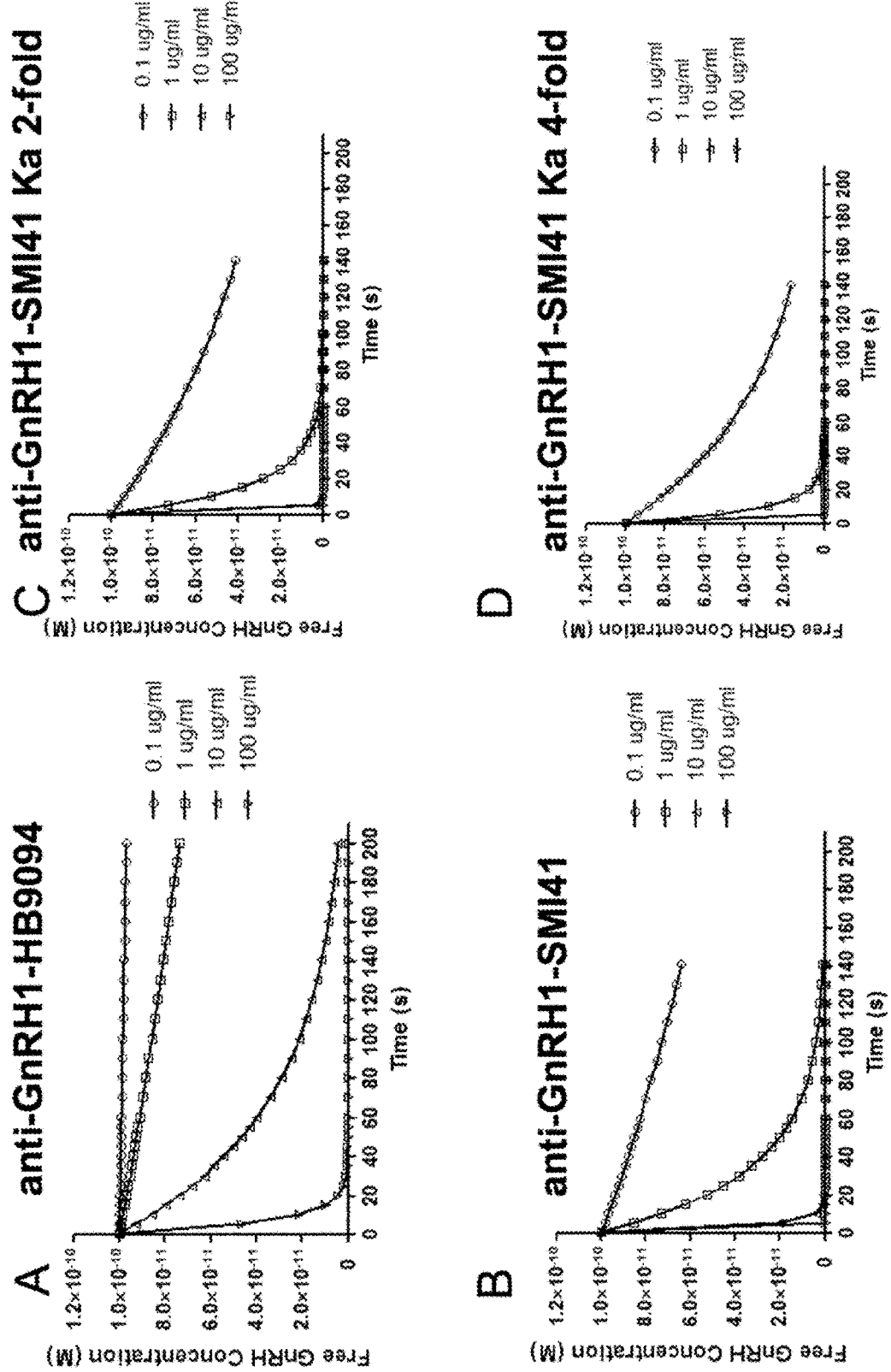
FIGS. 8A-8D are graphs depicting the predicted impact of altering Ka by 2 (8C) and 4 (8D) fold from the actual Ab1 (8A) and Ab2 (8B).

The relevance of on-rate can be seen by considering the predicted ability of the two anti-GnRH1 antibodies to bind ~90% of a 100 pg/ml pulse of GnRH1 within 30 sec to 1 min, in FIGS. 8A-8D. While the choice of this specific endpoint is somewhat arbitrary, as the size of GnRH1 pulses can be significantly lower, and the fraction that must be inhibited can be determined, it represents a conservative estimate of what must be achieved in order to inhibit fertility, based on the sum of the literature in many different species (reviewed in Clarke, I. J. 2002 *Reproduction Supplement* 59: 1-13; Vidal, A. and Clement, F. 2010 *J. Neuroendocrinology* 22: 1251-1266). FIGS. 8A-8D suggests that a 4-fold increase in on-rate of anti-GnRH1 SMI41 would result in inhibition of fertility with concentrations of antibody as low as 1 ug/ml. FIGS. 8A and 8B depict the predicted amounts of free GnRH (assuming 100 pM initial concentration) over time for different concentrations of anti-GnRH-HB9094 and anti-GnRH-SMI41, using the association rates calculated from FIG. 3 and FIG. 4, respectively. These observations suggest that anti-GnRH-HB9094 could lose effectiveness somewhere between 10 and 100 ug/mL, while anti-GnRH-SMI41 could lose effectiveness somewhere between 1 and 10 ug/mL (the fertility data illustrated in FIG. 6 and FIG. 7 suggests that SMI41 works better than HB9094, supporting this concept). However a version of antiGnRH-SMI41 with a 2 to 4 fold increase in on rate (FIGS. 8C and 8D) would be expected to be effective at significantly lower concentrations.

Range of Ab on Rates

Having an antibody that works well at low concentrations is also useful because, in some embodiments, one may want to have the antibody present initially in a significant excess—in a young animal—of that which is needed. This is because, while skeletal muscle is post-mitotic, and therefore the AAV or other antibody-expressing episomes will not be diluted out by cell division over time as they would be if introduced into the liver, wear and tear with aging inevitably leads to some muscle cell injury, death and replacement from stem cell populations (reviewed in Jang, Y. C. et al. 2011 *Cold Spring harb Symp Quant Biol.* 76: 101-111). This would be expected to lead to an age-dependent decrease in AAV-dependent antibody expression. In some embodiments, the desired amount to be injected into the subject can be approximately 1 ug/mL or less, so as to assist in keeping the cost of contraception per animal low enough to be cost effective.

Example 7

Pest Control

A population of feral cats is identified. Male and female cats are collected and injected intramuscularly with AAV expressing Anti-GnRH1 HB9094 or SMI41. The cats are placed back into the population. The population of cats will stop increasing as rapidly over time.

Example 8

Pest Control

A population of feral dogs is identified. Male and female dogs are collected and injected intramuscularly with AAV expressing Anti-GnRH-SMI41 or HB9094 and AAV expressing anti-GnRH1 Ab2. The dogs are placed back into the population. The population of dogs will stop increasing as rapidly over time.

Example 9

Behavior Control

An aggressive or territorial dog or cat is identified. The animal is administered AAV expressing Anti-GnRH1-HB9094 or SMI41. The animal's behavioral patterns will change given the reduced levels of GnRH1 available.

Example 10

Fertility Control in Captive, Owned or Managed Wild Populations

An animal is identified for which sterility is desired. Examples include owned dogs and cats, animals kept in zoos, and managed populations of horses, burros, coyotes, elephants. The animal is administered AAV expressing Anti-GnRH1-HB9094 or SMI41. Fertility is inhibited.

It is understood that the examples and embodiments described herein are for illustrative purposes only and that various modifications or changes in light thereof will be suggested to persons skilled in the art and are to be included within the spirit and purview of this application and scope of any appended claims.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls. All figures, tables, and appendices, as well as publications, patents, and patent applications, cited herein are hereby incorporated by reference in their entirety for all purposes.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A recombinant genetic construct comprising an antibody gene that encodes an antibody or a fragment thereof that binds to a protein, a peptide, or a small molecule specific to reproductive function, wherein the recombinant genetic construct is configured to be delivered and expressed in an animal subject, wherein the antibody comprises an amino acid sequence that is at least 90% identical to that in SEQ ID NOs: 10, 12, 13, or 14.

2. The recombinant genetic construct of claim 1, wherein the antibody inhibits a protein specific to reproductive function.

3. The recombinant genetic construct of claim 1, wherein the protein specific to reproductive function is one that, when bound by the antibody, causes sterility.

4. The recombinant genetic construct of claim 1, wherein the protein is a reproductive hormone, a protein component of the egg zona pellucida, or a protein component of the sperm plasma membrane.

5. The recombinant genetic construct of claim 1, wherein the amino acid sequence is at least 95% identical to that in SEQ ID NOs: 10, 12, 13, or 14.

6. The recombinant genetic construct of claim 1, wherein the amino acid sequence is at least 99% identical to that in SEQ ID NOs: 10, 12, 13, or 14.

7. The recombinant genetic construct of claim 1, wherein the antibody comprises 6 CDRs, wherein the 6 CDRs are 6 CDRs are encoded by SEQ ID NOs:10 and 12, or 13 and 14.

8. The recombinant genetic construct of claim 1, wherein the antibody comprises an amino acid sequence SEQ ID NOs: 10, 12, 13, or 14.

9. The recombinant genetic construct of claim 1, wherein the antibody comprises SEQ ID NOs:
   a) 10 and 12, or
   b) 13 and 14.

10. The recombinant genetic construct of claim 1, wherein the antibody comprises an amino acid sequence that is at least 90% identical to that in SEQ ID NO: 12.

11. The recombinant genetic construct of claim 1, wherein the antibody comprises an amino acid sequence that is at least 90% identical to that in SEQ ID NO: 13.

12. The recombinant genetic construct of claim 1, wherein the antibody or fragment thereof comprises an amino acid modification that enhances or suppresses an effector function of the encoded antibody or fragment.

13. The recombinant genetic construct of claim 1, comprising an antibody expression cassette comprising a tissue specific promoter, a regulatory element, and one or more microRNA target sites.

14. The recombinant genetic construct of claim 13, wherein the regulatory element is a 5' untranslated region (5' UTR) or a 3' untranslated region (3' UTR).

15. The recombinant genetic construct of claim 1, incorporated into a transfection vehicle selected from the group consisting of an adeno-associated virus (AAV), a lentivirus, a DNA-containing nanoparticle, a liposome-DNA mixture, and a peptide-DNA mixture.

16. A contraceptive composition comprising the recombinant genetic construct of claim 1.

17. The contraceptive composition of claim 16, configured to be delivered to an animal through intramuscular injection, subcutaneous injection, intravenous injection, intraperitoneal injection, oral delivery, electroporation through the skin, sonication, or nasal inhalation.

18. A pharmaceutical composition comprising:
 the recombinant genetic construct of claim 1; and
 a pharmaceutically acceptable carrier, wherein the recombinant genetic construct is present in at least 1 ug/ml, and wherein the pharmaceutically acceptable carrier can be combined with a nucleic acid.

19. The recombinant genetic construct of claim 1, wherein the antibody comprises 3 CDRs, wherein the 3 CDRs are 3 CDRs are encoded by SEQ ID NO: 28.

20. The recombinant genetic construct of claim 1, wherein the antibody comprises 3 CDRs, wherein the 3 CDRs are 3 CDRs are encoded by SEQ ID NO: 35.

21. The recombinant genetic construct of claim 1, wherein the antibody comprises an amino acid sequence that is at least 90% identical to that in SEQ ID NO: 14.

* * * * *

SEQUENCE LISTING

<160> NUMBER OF SEQ ID NOS: 66

<210> SEQ ID NO 1
<211> LENGTH: 2229
<212> TYPE: DNA
<213> ORGANISM: Mus musculus

<400> SEQUENCE: 1

| | | | | | | |
|---|---|---|---|---|---|---|
| atggcgacgg | gttcaagaac | ttccctactt | cttgcatttg | gcctgctttg | tttgccgtgg | 60 |
| ttacaggagg | gctcggcaca | gatccagttg | gtgcagtctg | gacctgaact | gaagaagcct | 120 |
| ggagagacag | tcaagatctc | ctgcaaggct | tctggatatc | ccttcacaaa | ctatggaatg | 180 |
| aactgggtga | agcaggctcc | aggaaagggt | ttaaagtgga | tgggctggat | aaacacctac | 240 |
| actggagagc | cagcatgtgc | tgatgacttc | aggggacggt | ttgccatctc | tttggaaacc | 300 |
| tccgccagaa | ctgcctattt | gcagatcaac | aacctcataa | atgaggacac | ggcaacatat | 360 |
| ttctgtgcaa | gaacgggggg | tggtaggtac | aactatggta | tggactattg | gggtcaagga | 420 |
| acctcagtca | ccgtctccag | cgctaaaacg | acacccccat | ctgtctatcc | actggcccct | 480 |
| ggatctgctg | cccaaactaa | ctccatggtg | accctgggat | gcctggtcaa | gggctatttc | 540 |
| cctgagccag | tgacagtgac | ctggaactct | ggatccctgt | ccagcggtgt | gcacaccttc | 600 |
| ccagctgtcc | tgcagtctga | cctctacact | ctgagcagct | cagtgactgt | ccctccagc | 660 |
| acctggccca | gcgagaccgt | cacctgcaac | gttgcccacc | cggccagcag | caccaaggtg | 720 |
| gacaagaaaa | ttgtgcccag | ggattgtggt | tgtaagcctt | gcatatgtac | agtcccagaa | 780 |
| gtatcatctg | tcttcatctt | ccccccaaag | cccaaggatg | tgctcaccat | tactctgact | 840 |
| cctaaggtca | cgtgtgttgt | ggtagacatc | agcaaggatg | atcccgaggt | ccagttcagc | 900 |
| tggtttgtag | atgatgtgga | ggtgcacaca | gctcagacgc | aaccccggga | ggagcagttc | 960 |
| aacagcactt | tccgctcagt | cagtgaactt | cccatcatgc | accaggactg | gctcaatggc | 1020 |
| aaggagttca | atgcagggt | caacagtgca | gctttccctg | ccccccatcga | gaaaaccatc | 1080 |
| tccaaaacca | aggcagacc | gaaggctccg | caggtgtaca | ccattccacc | tcccaaggag | 1140 |
| cagatggcca | aggataaagt | cagtctgacc | tgcatgataa | cagacttctt | ccctgaagac | 1200 |
| attactgtgg | agtggcagtg | gaatgggcag | ccagcggaga | actacaagaa | cactcagccc | 1260 |
| atcatggaca | cagatggctc | ttacttcgtc | tacagcaagc | tcaatgtgca | gaagagcaac | 1320 |
| tgggaggcag | gaaatacttt | cacctgctct | gtgttacatg | agggcctgca | caaccaccat | 1380 |
| actgagaaga | gcctctccca | ctctcctggt | aaacgaaaaa | gaagatcagg | ttcgggtgcg | 1440 |
| ccagtaaagc | agacattaaa | ctttgatttg | ctgaaacttg | caggtgatgt | agagtcaaat | 1500 |
| ccaggtccaa | tggcaacagg | gagccgaacc | tctctgctcc | ttgctttcgg | gctcctttgc | 1560 |
| ctaccgtggc | tccaagaggg | ctcggcacaa | attgttctca | cccagtctcc | agccatcatg | 1620 |
| tctgcatctc | caggggagaa | ggtcaccata | acctgcagtg | ccacctcaag | tgtaagttac | 1680 |
| atacactggt | tccagcagaa | gccaggcact | tctcccaaac | tctggattta | tagcacatcc | 1740 |
| aacctggctt | ctggagtccc | tgttcgcttc | agtggcagtg | gatctgggac | ctcttactct | 1800 |
| ctcacaatca | gccgaatgga | ggctgaagat | gctgccactt | attactgcca | gcaaaggagt | 1860 |
| agttacccac | ccacgttcgg | aggggggacc | aagctgaaa | taaacgggc | agatgctgca | 1920 |
| ccaactgtat | ccatcttccc | accatccagt | gagcagttaa | catctggagg | tgcctcagtc | 1980 |
| gtgtgcttct | tgaacaactt | ctaccccaaa | gacatcaatg | tcaagtggaa | gattgatggc | 2040 |
| agtgaacgac | aaaatggcgt | cctgaacagt | tggactgatc | aggacagcaa | agacagcacc | 2100 |

```
tacagcatga gcagcaccct cacgttgacc aaggacgagt atgaacgaca taacagctat    2160
acctgtgagg ccactcacaa gacatcaact tcacccattg tcaagagctt caacaggaat    2220
gagtgttag                                                            2229
```

<210> SEQ ID NO 2
<211> LENGTH: 742
<212> TYPE: PRT
<213> ORGANISM: Mus musculus

<400> SEQUENCE: 2

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ile Gln Leu Val Gln
            20                  25                  30

Ser Gly Pro Glu Leu Lys Lys Pro Gly Glu Thr Val Lys Ile Ser Cys
        35                  40                  45

Lys Ala Ser Gly Tyr Pro Phe Thr Asn Tyr Gly Met Asn Trp Val Lys
    50                  55                  60

Gln Ala Pro Gly Lys Gly Leu Lys Trp Met Gly Trp Ile Asn Thr Tyr
65                  70                  75                  80

Thr Gly Glu Pro Ala Cys Ala Asp Asp Phe Arg Gly Arg Phe Ala Ile
                85                  90                  95

Ser Leu Glu Thr Ser Ala Arg Thr Ala Tyr Leu Gln Ile Asn Asn Leu
            100                 105                 110

Ile Asn Glu Asp Thr Ala Thr Tyr Phe Cys Ala Arg Thr Gly Gly Gly
        115                 120                 125

Arg Tyr Asn Tyr Gly Met Asp Tyr Trp Gly Gln Gly Thr Ser Val Thr
    130                 135                 140

Val Ser Ser Ala Lys Thr Thr Pro Pro Ser Val Tyr Pro Leu Ala Pro
145                 150                 155                 160

Gly Ser Ala Ala Gln Thr Asn Ser Met Val Thr Leu Gly Cys Leu Val
                165                 170                 175

Lys Gly Tyr Phe Pro Glu Pro Val Thr Val Thr Trp Asn Ser Gly Ser
            180                 185                 190

Leu Ser Ser Gly Val His Thr Phe Pro Ala Val Leu Gln Ser Asp Leu
        195                 200                 205

Tyr Thr Leu Ser Ser Ser Val Thr Val Pro Ser Ser Thr Trp Pro Ser
    210                 215                 220

Glu Thr Val Thr Cys Asn Val Ala His Pro Ala Ser Ser Thr Lys Val
225                 230                 235                 240

Asp Lys Lys Ile Val Pro Arg Asp Cys Gly Cys Lys Pro Cys Ile Cys
                245                 250                 255

Thr Val Pro Glu Val Ser Ser Val Phe Ile Phe Pro Pro Lys Pro Lys
            260                 265                 270

Asp Val Leu Thr Ile Thr Leu Thr Pro Lys Val Thr Cys Val Val Val
        275                 280                 285

Asp Ile Ser Lys Asp Asp Pro Glu Val Gln Phe Ser Trp Phe Val Asp
    290                 295                 300

Asp Val Glu Val His Thr Ala Gln Thr Gln Pro Arg Glu Glu Gln Phe
305                 310                 315                 320

Asn Ser Thr Phe Arg Ser Val Ser Glu Leu Pro Ile Met His Gln Asp
                325                 330                 335

Trp Leu Asn Gly Lys Glu Phe Lys Cys Arg Val Asn Ser Ala Ala Phe
```

```
            340                 345                 350
Pro Ala Pro Ile Glu Lys Thr Ile Ser Lys Thr Lys Gly Arg Pro Lys
            355                 360                 365

Ala Pro Gln Val Tyr Thr Ile Pro Pro Lys Glu Gln Met Ala Lys
        370                 375                 380

Asp Lys Val Ser Leu Thr Cys Met Ile Thr Asp Phe Phe Pro Glu Asp
385                 390                 395                 400

Ile Thr Val Glu Trp Gln Trp Asn Gly Gln Pro Ala Glu Asn Tyr Lys
                405                 410                 415

Asn Thr Gln Pro Ile Met Asp Thr Asp Gly Ser Tyr Phe Val Tyr Ser
            420                 425                 430

Lys Leu Asn Val Gln Lys Ser Asn Trp Glu Ala Gly Asn Thr Phe Thr
        435                 440                 445

Cys Ser Val Leu His Glu Gly Leu His Asn His Thr Glu Lys Ser
    450                 455                 460

Leu Ser His Ser Pro Gly Lys Arg Lys Arg Arg Ser Gly Ser Gly Ala
465                 470                 475                 480

Pro Val Lys Gln Thr Leu Asn Phe Asp Leu Leu Lys Leu Ala Gly Asp
                485                 490                 495

Val Glu Ser Asn Pro Gly Pro Met Ala Thr Gly Ser Arg Thr Ser Leu
            500                 505                 510

Leu Leu Ala Phe Gly Leu Leu Cys Leu Pro Trp Leu Gln Glu Gly Ser
        515                 520                 525

Ala Gln Ile Val Leu Thr Gln Ser Pro Ala Ile Met Ser Ala Ser Pro
    530                 535                 540

Gly Glu Lys Val Thr Ile Thr Cys Ser Ala Thr Ser Ser Val Ser Tyr
545                 550                 555                 560

Ile His Trp Phe Gln Gln Lys Pro Gly Thr Ser Pro Lys Leu Trp Ile
                565                 570                 575

Tyr Ser Thr Ser Asn Leu Ala Ser Gly Val Pro Val Arg Phe Ser Gly
            580                 585                 590

Ser Gly Ser Gly Thr Ser Tyr Ser Leu Thr Ile Ser Arg Met Glu Ala
        595                 600                 605

Glu Asp Ala Ala Thr Tyr Tyr Cys Gln Gln Arg Ser Ser Tyr Pro Pro
    610                 615                 620

Thr Phe Gly Gly Gly Thr Lys Leu Glu Ile Lys Arg Ala Asp Ala Ala
625                 630                 635                 640

Pro Thr Val Ser Ile Phe Pro Pro Ser Ser Glu Gln Leu Thr Ser Gly
                645                 650                 655

Gly Ala Ser Val Val Cys Phe Leu Asn Asn Phe Tyr Pro Lys Asp Ile
            660                 665                 670

Asn Val Lys Trp Lys Ile Asp Gly Ser Glu Arg Gln Asn Gly Val Leu
        675                 680                 685

Asn Ser Trp Thr Asp Gln Asp Ser Lys Asp Ser Thr Tyr Ser Met Ser
    690                 695                 700

Ser Thr Leu Thr Leu Thr Lys Asp Glu Tyr Glu Arg His Asn Ser Tyr
705                 710                 715                 720

Thr Cys Glu Ala Thr His Lys Thr Ser Thr Ser Pro Ile Val Lys Ser
                725                 730                 735

Phe Asn Arg Asn Glu Cys
            740

<210> SEQ ID NO 3
```

```
<211> LENGTH: 2241
<212> TYPE: DNA
<213> ORGANISM: Mus musculus

<400> SEQUENCE: 3
atggcgacgg gttcaagaac ttccctactt cttgcatttg gcctgctttg tttgccgtgg       60
ttacaggagg gctcggcaca agttactcta aaagagtctg gccctgggat attgaggccc      120
tcacagaccc tcgatctgac ttgttctttc tctgggtttt cactgagcac ttctggtctg      180
agtgtaggct ggattcgtca gccttcaggg aagggtctgg agtggctggc acacatttgg      240
tgggatgatg tgaagtactt taacccatcc ctgaagagca gactcacaat ctccaaggat      300
agctccagaa accaggtgtt cctcaagatc accagtgtgg acactgcaga tagtgccaca      360
taccactgta ctcgaggacc tctgggtcac ggatttgact actggggcca agggactctg      420
gtcactgtct ctgccgctaa aacgacaccc ccatctgtct atccactggc ccctggatct      480
gctgcccaaa ctaactccat ggtgaccctg ggatgcctgg tcaagggcta tttccctgag      540
ccagtgacag tgacctggaa ctctggatcc ctgtccagcg gtgtgcacac cttcccagct      600
gtcctgcagt ctgacctcta cactctgagc agctcagtga ctgtcccctc cagcacctgg      660
cccagcgaga ccgtcacctg caacgttgcc cacccggcca gcagcaccaa ggtggacaag      720
aaaattgtgc ccagggattg tggttgtaag ccttgcatat gtacagtccc agaagtatca      780
tctgtcttca tcttcccccc aaagcccaag gatgtgctca ccattactct gactcctaag      840
gtcacgtgtg ttgtggtaga catcagcaag gatgatcccg aggtccagtt cagctggttt      900
gtagatgatg tggaggtgca cacagctcag acgcaacccc gggaggagca gttcaacagc      960
actttccgct cagtcagtga acttcccatc atgcaccagg actggctcaa tggcaaggag     1020
ttcaaatgca gggtcaacag tgcagctttc cctgccccca tcgagaaaac catctccaaa     1080
accaaaggca gaccgaaggc tccgcaggtg tacaccattc cacctcccaa ggagcagatg     1140
gccaaggata aagtcagtct gacctgcatg ataacagact tcttccctga agacattact     1200
gtggagtggc agtggaatgg gcagccagcg gagaactaca agaacactca gcccatcatg     1260
gacacagatg gctcttactt cgtctacagc aagctcaatg tgcagaagag caactgggag     1320
gcaggaaata ctttcacctg ctctgtgtta catgagggcc tgcacaacca ccatactgag     1380
aagagcctct cccactctcc tggtaaacga aaaagaagat caggttcggg tgcgccagta     1440
aagcagacat taaactttga tttgctgaaa cttgcaggtg atgtagagtc aaatccaggt     1500
ccaatggcaa cagggagccg aacctctctg ctccttgctt tcgggctcct ttgcctaccg     1560
tggctccaag agggctcggc agatgttgtg atgacccaaa ctccactctc cctgcctgtc     1620
agtcttggag atcaagcctt catctcttgc agatctagtc agagccttgt acacagtgat     1680
ggaaacagct acttacattg gtacctgcag aagccaggcc agtctccaaa gctcctgatc     1740
tacaaagttt ccaaccgatt ttctggggtc ccagacaggt tcagtggcag tggatcaggg     1800
acagatttca cactcaagat cagcagagtg gaggctgagg atctgggact ttatttctgc     1860
tctcaaacta cacatgttcc ttggacgttc ggtggaggca ccaagctgga aatcaaacgg     1920
gcagatgctg caccaactgt atccatcttc ccaccatcca gtgagcagtt aacatctgga     1980
ggtgcctcag tcgtgtgctt cttgaacaac ttctacccca agacatcaa tgtcaagtgg     2040 aagattgatg gcagtgaacg acaaaatggc gtcctgaaca gttggactga tcaggacagc     2100
aaagacagca cctacagcat gagcagcacc ctcacgttga ccaaggacga gtatgaacga     2160
cataacagct atacctgtga ggccactcac aagacatcaa cttcacccat tgtcaagagc     2220
```
ttcaacagga atgagtgtta g                                              2241

<210> SEQ ID NO 4
<211> LENGTH: 746
<212> TYPE: PRT
<213> ORGANISM: Mus musculus

<400> SEQUENCE: 4

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Val Thr Leu Lys Glu
            20                  25                  30

Ser Gly Pro Gly Ile Leu Arg Pro Ser Gln Thr Leu Asp Leu Thr Cys
        35                  40                  45

Ser Phe Ser Gly Phe Ser Leu Ser Thr Ser Gly Leu Ser Val Gly Trp
    50                  55                  60

Ile Arg Gln Pro Ser Gly Lys Gly Leu Glu Trp Leu Ala His Ile Trp
65                  70                  75                  80

Trp Asp Asp Val Lys Tyr Phe Asn Pro Ser Leu Lys Ser Arg Leu Thr
                85                  90                  95

Ile Ser Lys Asp Ser Ser Arg Asn Gln Val Phe Leu Lys Ile Thr Ser
            100                 105                 110

Val Asp Thr Ala Asp Ser Ala Thr Tyr His Cys Thr Arg Gly Pro Leu
        115                 120                 125

Gly His Gly Phe Asp Tyr Trp Gly Gln Gly Thr Leu Val Thr Val Ser
    130                 135                 140

Ala Ala Lys Thr Thr Pro Pro Ser Val Tyr Pro Leu Ala Pro Gly Ser
145                 150                 155                 160

Ala Ala Gln Thr Asn Ser Met Val Thr Leu Gly Cys Leu Val Lys Gly
                165                 170                 175

Tyr Phe Pro Glu Pro Val Thr Val Thr Trp Asn Ser Gly Ser Leu Ser
            180                 185                 190

Ser Gly Val His Thr Phe Pro Ala Val Leu Gln Ser Asp Leu Tyr Thr
        195                 200                 205

Leu Ser Ser Ser Val Thr Val Pro Ser Ser Thr Trp Pro Ser Glu Thr
    210                 215                 220

Val Thr Cys Asn Val Ala His Pro Ala Ser Ser Thr Lys Val Asp Lys
225                 230                 235                 240

Lys Ile Val Pro Arg Asp Cys Gly Cys Lys Pro Cys Ile Cys Thr Val
                245                 250                 255

Pro Glu Val Ser Ser Val Phe Ile Phe Pro Pro Lys Pro Lys Asp Val
            260                 265                 270

Leu Thr Ile Thr Leu Thr Pro Lys Val Thr Cys Val Val Val Asp Ile
        275                 280                 285

Ser Lys Asp Asp Pro Glu Val Gln Phe Ser Trp Phe Val Asp Asp Val
    290                 295                 300

Glu Val His Thr Ala Gln Thr Gln Pro Arg Glu Glu Gln Phe Asn Ser
305                 310                 315                 320

Thr Phe Arg Ser Val Ser Glu Leu Pro Ile Met His Gln Asp Trp Leu
                325                 330                 335

Asn Gly Lys Glu Phe Lys Cys Arg Val Asn Ser Ala Ala Phe Pro Ala
            340                 345                 350

Pro Ile Glu Lys Thr Ile Ser Lys Thr Lys Gly Arg Pro Lys Ala Pro
        355                 360                 365
```

Gln Val Tyr Thr Ile Pro Pro Lys Glu Gln Met Ala Lys Asp Lys
    370             375                 380

Val Ser Leu Thr Cys Met Ile Thr Asp Phe Phe Pro Glu Asp Ile Thr
385                 390                 395                 400

Val Glu Trp Gln Trp Asn Gly Gln Pro Ala Glu Asn Tyr Lys Asn Thr
                405                 410                 415

Gln Pro Ile Met Asp Thr Asp Gly Ser Tyr Phe Val Tyr Ser Lys Leu
            420                 425                 430

Asn Val Gln Lys Ser Asn Trp Glu Ala Gly Asn Thr Phe Thr Cys Ser
        435                 440                 445

Val Leu His Glu Gly Leu His Asn His His Thr Glu Lys Ser Leu Ser
450                 455                 460

His Ser Pro Gly Lys Arg Lys Arg Arg Ser Gly Ser Gly Ala Pro Val
465                 470                 475                 480

Lys Gln Thr Leu Asn Phe Asp Leu Leu Lys Leu Ala Gly Asp Val Glu
                485                 490                 495

Ser Asn Pro Gly Pro Met Ala Thr Gly Ser Arg Thr Ser Leu Leu Leu
            500                 505                 510

Ala Phe Gly Leu Leu Cys Leu Pro Trp Leu Gln Glu Gly Ser Ala Asp
        515                 520                 525

Val Val Met Thr Gln Thr Pro Leu Ser Leu Pro Val Ser Leu Gly Asp
530                 535                 540

Gln Ala Phe Ile Ser Cys Arg Ser Ser Gln Ser Leu Val His Ser Asp
545                 550                 555                 560

Gly Asn Ser Tyr Leu His Trp Tyr Leu Gln Lys Pro Gly Gln Ser Pro
                565                 570                 575

Lys Leu Leu Ile Tyr Lys Val Ser Asn Arg Phe Ser Gly Val Pro Asp
            580                 585                 590

Arg Phe Ser Gly Ser Gly Ser Gly Thr Asp Phe Thr Leu Lys Ile Ser
        595                 600                 605

Arg Val Glu Ala Glu Asp Leu Gly Leu Tyr Phe Cys Ser Gln Thr Thr
    610                 615                 620

His Val Pro Trp Thr Phe Gly Gly Gly Thr Lys Leu Glu Ile Lys Arg
625                 630                 635                 640

Ala Asp Ala Ala Pro Thr Val Ser Ile Phe Pro Pro Ser Ser Glu Gln
                645                 650                 655

Leu Thr Ser Gly Gly Ala Ser Val Val Cys Phe Leu Asn Asn Phe Tyr
            660                 665                 670

Pro Lys Asp Ile Asn Val Lys Trp Lys Ile Asp Gly Ser Glu Arg Gln
        675                 680                 685

Asn Gly Val Leu Asn Ser Trp Thr Asp Gln Asp Ser Lys Asp Ser Thr
    690                 695                 700

Tyr Ser Met Ser Ser Thr Leu Thr Leu Thr Lys Asp Glu Tyr Glu Arg
705                 710                 715                 720

His Asn Ser Tyr Thr Cys Glu Ala Thr His Lys Thr Ser Thr Ser Pro
                725                 730                 735

Ile Val Lys Ser Phe Asn Arg Asn Glu Cys
            740                 745

<210> SEQ ID NO 5
<211> LENGTH: 324
<212> TYPE: DNA
<213> ORGANISM: Homo sapiens

<400> SEQUENCE: 5

```
tcttctgaac tgactcagga ccctgttgtg tctgtggcct tgggacagac agtcaggatc      60
acatgccaag agacagcct cagaacctat catgcaagct ggtaccagca gaagccaaga      120
caggcccctg tacttgtcat ctatgatgaa acaaccggc cctcagggat cccagaccga      180
ttctctggct ccacctcagg aaacacagct tccttgacca tcactggggc tcaggcggaa      240
gatgaggctg actattactg taactcccgg gacagcagtg gtaaccgtct ggtattcggc      300
ggagggacca agctgaccgt ccta                                            324
```

<210> SEQ ID NO 6
<211> LENGTH: 108
<212> TYPE: PRT
<213> ORGANISM: Homo sapiens

<400> SEQUENCE: 6

```
Ser Ser Glu Leu Thr Gln Asp Pro Val Val Ser Val Ala Leu Gly Gln
1               5                   10                  15
Thr Val Arg Ile Thr Cys Gln Gly Asp Ser Leu Arg Thr Tyr His Ala
            20                  25                  30
Ser Trp Tyr Gln Gln Lys Pro Arg Gln Ala Pro Val Leu Val Ile Tyr
        35                  40                  45
Asp Glu Asn Asn Arg Pro Ser Gly Ile Pro Asp Arg Phe Ser Gly Ser
    50                  55                  60
Thr Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Asn Arg
                85                  90                  95
Leu Val Phe Gly Gly Gly Thr Lys Leu Thr Val Leu
            100                 105
```

<210> SEQ ID NO 7
<211> LENGTH: 372
<212> TYPE: DNA
<213> ORGANISM: Homo sapiens

<400> SEQUENCE: 7

```
caggtgcagc tacagcagtg gggcgcagga ctgttgaagc cttcggagac cctgtccctc      60
acttgcgatg tctatggtgg gtccttcagt ggttactact ggagttggat ccgccagccc     120
ccagggaagg gctggagtg gattggggaa atcaatcata gtggaagcac caactacaac     180
ccgtccctca ggagtcgagt caccatatca gtagacacgt ccaagaatca gttctccctg     240
aagctgaggt ctgtgaccgc cgcggacacg gctgtgtatt actgtgcgag aggctttatg     300
gttcggggaa ttatgtggaa ctactactac atggacgtct ggggcaaagg gaccacggtc     360
accgtctccc ca                                                         372
```

<210> SEQ ID NO 8
<211> LENGTH: 124
<212> TYPE: PRT
<213> ORGANISM: Homo sapiens

<400> SEQUENCE: 8

```
Gln Val Gln Leu Gln Gln Trp Gly Ala Gly Leu Leu Lys Pro Ser Glu
1               5                   10                  15
Thr Leu Ser Leu Thr Cys Asp Val Tyr Gly Gly Ser Phe Ser Gly Tyr
            20                  25                  30
```

```
Tyr Trp Ser Trp Ile Arg Gln Pro Gly Lys Gly Leu Glu Trp Ile
            35                  40                  45
Gly Glu Ile Asn His Ser Gly Ser Thr Asn Tyr Asn Pro Ser Leu Arg
 50                  55                  60
Ser Arg Val Thr Ile Ser Val Asp Thr Ser Lys Asn Gln Phe Ser Leu
 65                  70                  75                  80
Lys Leu Arg Ser Val Thr Ala Ala Asp Thr Ala Val Tyr Tyr Cys Ala
                 85                  90                  95
Arg Gly Phe Met Val Arg Gly Ile Met Trp Asn Tyr Tyr Met Asp
                100                 105                 110
Val Trp Gly Lys Gly Thr Thr Val Thr Val Ser Pro
            115                 120
```

<210> SEQ ID NO 9
<211> LENGTH: 348
<212> TYPE: DNA
<213> ORGANISM: Mus musculus

<400> SEQUENCE: 9

```
cagatccagt tggtgcagtc tggacctgag gtgaagaagc ctggagagac agtcaagatc    60
tcctgcaagg cttctggtta taagttcaca gactattcaa ttcactgggt gaagcaggtt   120
ccaggaaagg gtttaaagtg gatgggctgg atagacactg agactggtga gtcaacatat   180
gcagatgact tcaggggacg gtttgacttc tctttggaaa cttctgtcag cactgcctct   240
ttggagatca caaacctcaa aaatgacgac acgactacat attttgtgc tagatgggga   300
tcgggccttg cttattgggg ccaagggact ctggtcactg tctctgca                348
```

<210> SEQ ID NO 10
<211> LENGTH: 96
<212> TYPE: PRT
<213> ORGANISM: Mus musculus

<400> SEQUENCE: 10

```
Gln Ile Gln Leu Val Gln Ser Gly Pro Glu Val Lys Lys Pro Gly Glu
 1               5                  10                  15
Thr Val Lys Ile Ser Cys Lys Ala Ser Gly Tyr Lys Phe Thr Asp Tyr
                 20                  25                  30
Ser Ile His Trp Val Lys Gln Val Pro Gly Lys Gly Leu Lys Trp Met
            35                  40                  45
Gly Trp Ile Asp Thr Glu Thr Gly Glu Ser Thr Tyr Ala Asp Asp Phe
 50                  55                  60
Arg Gly Arg Phe Asp Phe Ser Leu Glu Thr Ser Val Ser Thr Ala Ser
 65                  70                  75                  80
Ser Gly Leu Ala Tyr Trp Gly Gln Gly Thr Leu Val Thr Val Ser Ala
                 85                  90                  95
```

<210> SEQ ID NO 11
<211> LENGTH: 336
<212> TYPE: DNA
<213> ORGANISM: Mus musculus

<400> SEQUENCE: 11

```
gatgctgtgc tgacccagac tccactcact ttgtcggtta ccagtggaca accagcctcc    60
atctcttgca agtcaagtca gagcctctta gatagtgatg gaaagacata tttgagttgg   120
ttgttacaga ggccaggcca gtctccaaag tgcctgatct atctggtgtc taaactggac   180
tctggagtcc ctgacaggtt cactggcagt ggatcaggga cagatttcac actgaaaatc   240
```

```
aacagagtgg aggctgagga tttgggagtt tattgttgct ggcaaggaac acacttgtgc    300
accttcggag gggggaccaa gctggagata aaacgg                              336
```

<210> SEQ ID NO 12
<211> LENGTH: 112
<212> TYPE: PRT
<213> ORGANISM: Mus musculus

<400> SEQUENCE: 12

Asp Ala Val Leu Thr Gln Thr Pro Leu Thr Leu Ser Val Thr Ser Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Ser Trp Leu Leu Gln Arg Pro Gly Gln Ser
        35                  40                  45

Pro Lys Cys Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Asn Arg Val Glu Ala Glu Asp Leu Gly Val Tyr Cys Cys Trp Gln Gly
                85                  90                  95

Thr His Leu Cys Thr Phe Gly Gly Gly Thr Lys Leu Glu Ile Lys Arg
            100                 105                 110

<210> SEQ ID NO 13
<211> LENGTH: 114
<212> TYPE: PRT
<213> ORGANISM: Mus musculus

<400> SEQUENCE: 13

Gln Val Gln Leu Gln Gln Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ser Ile Gly Gly Gly Ser Tyr Thr Tyr Ala Ala Tyr Pro Asp
    50                  55                  60

Ser Val Lys Gly Arg Phe Thr Ile Ser Arg Asp Asn Ala Lys Asn Asn
65                  70                  75                  80

Leu Tyr Leu Gln Met Ser Ser Leu Arg Ser Glu Asp Thr Ala Leu Phe
                85                  90                  95

Tyr Cys Val Arg Leu Tyr Gly Thr Ser Pro Trp Phe Asp Tyr Trp Gly
            100                 105                 110

Gln Gly

<210> SEQ ID NO 14
<211> LENGTH: 109
<212> TYPE: PRT
<213> ORGANISM: Mus musculus

<400> SEQUENCE: 14

Asp Ile Gln Met Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

```
Ile His Trp Tyr Gln Gln Arg Thr Asn Gly Ser Pro Arg Leu Leu Ile
            35                  40                  45

Ala Ala Ala Tyr Ser Ala Ser Glu Ser Tyr Ala Pro Ser Arg Phe Ser
 50                  55                  60

Gly Ser Arg Ser Gly Thr Asp Ala Thr Leu Ser Ile Asn Ser Val Glu
 65                  70                  75                  80

Ser Glu Asp Ile Ala Asp Tyr Tyr Cys Gln Gln Ser Asn Ser Trp Pro
                 85                  90                  95

Leu Thr Phe Gly Ala Gly Thr Lys Leu Glu Ile Lys Arg
            100                 105
```

<210> SEQ ID NO 15
<211> LENGTH: 26
<212> TYPE: PRT
<213> ORGANISM: Artificial Sequence
<220> FEATURE:
<223> OTHER INFORMATION: synthetic peptide

<400> SEQUENCE: 15

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala
            20                  25
```

<210> SEQ ID NO 16
<211> LENGTH: 32
<212> TYPE: PRT
<213> ORGANISM: Artificial Sequence
<220> FEATURE:
<223> OTHER INFORMATION: synthetic peptide

<400> SEQUENCE: 16

```
Arg Lys Arg Arg Ser Gly Ser Gly Ala Pro Val Lys Gln Thr Leu Asn
 1               5                  10                  15

Phe Asp Leu Leu Lys Leu Ala Gly Asp Val Glu Ser Asn Pro Gly Pro
                 20                  25                  30
```

<210> SEQ ID NO 17
<211> LENGTH: 147
<212> TYPE: PRT
<213> ORGANISM: Mus musculus

<400> SEQUENCE: 17

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Gln Ile Gln Leu Val Gln
            20                  25                  30

Ser Gly Pro Glu Leu Lys Lys Pro Gly Glu Thr Val Lys Ile Ser Cys
        35                  40                  45

Lys Ala Ser Gly Tyr Pro Phe Thr Asn Tyr Gly Met Asn Trp Val Lys
 50                  55                  60

Gln Ala Pro Gly Lys Gly Leu Lys Trp Met Gly Trp Ile Asn Thr Tyr
 65                  70                  75                  80

Thr Gly Glu Pro Ala Cys Ala Asp Asp Phe Arg Gly Arg Phe Ala Ile
                 85                  90                  95

Ser Leu Glu Thr Ser Ala Arg Thr Ala Tyr Leu Gln Ile Asn Asn Leu
            100                 105                 110

Ile Asn Glu Asp Thr Ala Thr Tyr Phe Cys Ala Arg Thr Gly Gly Gly
        115                 120                 125
```

Arg Tyr Asn Tyr Gly Met Asp Tyr Trp Gly Gln Gly Thr Ser Val Thr
    130                 135                 140

Val Ser Ser
145

<210> SEQ ID NO 18
<211> LENGTH: 7
<212> TYPE: PRT
<213> ORGANISM: Mus musculus

<400> SEQUENCE: 18

Gly Tyr Pro Phe Thr Asn Tyr
1               5

<210> SEQ ID NO 19
<211> LENGTH: 5
<212> TYPE: PRT
<213> ORGANISM: Mus musculus

<400> SEQUENCE: 19

Asn Tyr Gly Met Asn
1               5

<210> SEQ ID NO 20
<211> LENGTH: 6
<212> TYPE: PRT
<213> ORGANISM: Mus musculus

<400> SEQUENCE: 20

Asn Thr Tyr Thr Gly Glu
1               5

<210> SEQ ID NO 21
<211> LENGTH: 17
<212> TYPE: PRT
<213> ORGANISM: Mus musculus

<400> SEQUENCE: 21

Trp Ile Asn Thr Tyr Thr Gly Glu Pro Ala Cys Ala Asp Asp Phe Arg
1               5                   10                  15

Gly

<210> SEQ ID NO 22
<211> LENGTH: 12
<212> TYPE: PRT
<213> ORGANISM: Mus musculus

<400> SEQUENCE: 22

Thr Gly Gly Gly Arg Tyr Asn Tyr Gly Met Asp Tyr
1               5                   10

<210> SEQ ID NO 23
<211> LENGTH: 12
<212> TYPE: PRT
<213> ORGANISM: Mus musculus

<400> SEQUENCE: 23

Thr Gly Gly Gly Arg Tyr Asn Tyr Gly Met Asp Tyr
1               5                   10

<210> SEQ ID NO 24
<211> LENGTH: 239
<212> TYPE: PRT
<213> ORGANISM: Mus musculus

<400> SEQUENCE: 24

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ile Val Leu Thr Gln
            20                  25                  30

Ser Pro Ala Ile Met Ser Ala Ser Pro Gly Glu Lys Val Thr Ile Thr
        35                  40                  45

Cys Ser Ala Thr Ser Ser Val Ser Tyr Ile His Trp Phe Gln Gln Lys
    50                  55                  60

Pro Gly Thr Ser Pro Lys Leu Trp Ile Tyr Ser Thr Ser Asn Leu Ala
65                  70                  75                  80

Ser Gly Val Pro Val Arg Phe Ser Gly Ser Gly Ser Gly Thr Ser Tyr
                85                  90                  95

Ser Leu Thr Ile Ser Arg Met Glu Ala Glu Asp Ala Ala Thr Tyr Tyr
            100                 105                 110

Cys Gln Gln Arg Ser Ser Tyr Pro Pro Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 25
<211> LENGTH: 10
<212> TYPE: PRT
<213> ORGANISM: Mus musculus

<400> SEQUENCE: 25

Ser Ala Thr Ser Ser Val Ser Tyr Ile His
1               5                   10

<210> SEQ ID NO 26
<211> LENGTH: 7
<212> TYPE: PRT
<213> ORGANISM: Mus musculus

<400> SEQUENCE: 26

Ser Thr Ser Asn Leu Ala Ser
1               5

<210> SEQ ID NO 27
<211> LENGTH: 9
<212> TYPE: PRT
<213> ORGANISM: Mus musculus

<400> SEQUENCE: 27

Gln Gln Arg Ser Ser Tyr Pro Pro Thr

<210> SEQ ID NO 28
<211> LENGTH: 145
<212> TYPE: PRT
<213> ORGANISM: Mus musculus

<400> SEQUENCE: 28

Met Ala Thr Gly Ser Arg Thr Ser Leu Leu Ala Phe Gly Leu Leu
1               5                   10                  15

Cys Leu Pro Trp Leu Gln Glu Gly Ser Ala Gln Val Thr Leu Lys Glu
            20                  25                  30

Ser Gly Pro Gly Ile Leu Arg Pro Ser Gln Thr Leu Asp Leu Thr Cys
        35                  40                  45

Ser Phe Ser Gly Phe Ser Leu Ser Thr Ser Gly Leu Ser Val Gly Trp
    50                  55                  60

Ile Arg Gln Pro Ser Gly Lys Gly Leu Glu Trp Leu Ala His Ile Trp
65                  70                  75                  80

Trp Asp Asp Val Lys Tyr Phe Asn Pro Ser Leu Lys Ser Arg Leu Thr
                85                  90                  95

Ile Ser Lys Asp Ser Ser Arg Asn Gln Val Phe Leu Lys Ile Thr Ser
            100                 105                 110

Val Asp Thr Ala Asp Ser Ala Thr Tyr His Cys Thr Arg Gly Pro Leu
        115                 120                 125

Gly His Gly Phe Asp Tyr Trp Gly Gln Gly Thr Leu Val Thr Val Ser
    130                 135                 140

Ala
145

<210> SEQ ID NO 29
<211> LENGTH: 9
<212> TYPE: PRT
<213> ORGANISM: Mus musculus

<400> SEQUENCE: 29

Gly Phe Ser Leu Ser Thr Ser Gly Leu
1               5

<210> SEQ ID NO 30
<211> LENGTH: 7
<212> TYPE: PRT
<213> ORGANISM: Mus musculus

<400> SEQUENCE: 30

Thr Ser Gly Leu Ser Val Gly
1               5

<210> SEQ ID NO 31
<211> LENGTH: 5
<212> TYPE: PRT
<213> ORGANISM: Mus musculus

<400> SEQUENCE: 31

Trp Trp Asp Asp Val
1               5

<210> SEQ ID NO 32
<211> LENGTH: 16
<212> TYPE: PRT
<213> ORGANISM: Mus musculus

```
<400> SEQUENCE: 32

His Ile Trp Trp Asp Asp Val Lys Tyr Pro Asn Pro Ser Leu Lys Ser
1               5                   10                  15

<210> SEQ ID NO 33
<211> LENGTH: 9
<212> TYPE: PRT
<213> ORGANISM: Mus musculus

<400> SEQUENCE: 33

Gly Pro Leu Gly His Gly Phe Asp Tyr
1               5

<210> SEQ ID NO 34
<211> LENGTH: 9
<212> TYPE: PRT
<213> ORGANISM: Mus musculus

<400> SEQUENCE: 34

Gly Pro Leu Gly His Gly Phe Asp Tyr
1               5

<210> SEQ ID NO 35
<211> LENGTH: 139
<212> TYPE: PRT
<213> ORGANISM: Mus musculus

<400> SEQUENCE: 35

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Val Val Met Thr Gln
                20                  25                  30

Thr Pro Leu Ser Leu Pro Val Ser Leu Gly Asp Gln Ala Phe Ile Ser
            35                  40                  45

Cys Arg Ser Ser Gln Ser Leu Val His Ser Asp Gly Asn Ser Tyr Leu
    50                  55                  60

His Trp Tyr Leu Gln Lys Pro Gly Gln Ser Pro Lys Leu Leu Ile Tyr
65                  70                  75                  80

Lys Val Ser Asn Arg Phe Ser Gly Val Pro Asp Arg Phe Ser Gly Ser
                85                  90                  95

Gly Ser Gly Thr Asp Phe Thr Leu Lys Ile Ser Arg Val Glu Ala Glu
            100                 105                 110

Asp Leu Gly Leu Tyr Phe Cys Ser Gln Thr Thr His Val Pro Trp Thr
        115                 120                 125

Phe Gly Gly Gly Thr Lys Leu Glu Ile Lys Arg
    130                 135

<210> SEQ ID NO 36
<211> LENGTH: 16
<212> TYPE: PRT
<213> ORGANISM: Mus musculus

<400> SEQUENCE: 36

Arg Ser Ser Gln Ser Leu Val His Ser Asp Gly Asn Ser Tyr Leu His
1               5                   10                  15

<210> SEQ ID NO 37
<211> LENGTH: 7
<212> TYPE: PRT
<213> ORGANISM: Mus musculus
```

```
<400> SEQUENCE: 37

Lys Val Ser Asn Arg Phe Ser
1               5

<210> SEQ ID NO 38
<211> LENGTH: 9
<212> TYPE: PRT
<213> ORGANISM: Mus musculus

<400> SEQUENCE: 38

Ser Gln Thr Thr His Val Pro Trp Thr
1               5

<210> SEQ ID NO 39
<211> LENGTH: 7
<212> TYPE: PRT
<213> ORGANISM: Homo sapiens

<400> SEQUENCE: 39

Gly Gly Ser Phe Ser Gly Tyr
1               5

<210> SEQ ID NO 40
<211> LENGTH: 5
<212> TYPE: PRT
<213> ORGANISM: Homo sapiens

<400> SEQUENCE: 40

Gly Tyr Tyr Trp Ser
1               5

<210> SEQ ID NO 41
<211> LENGTH: 5
<212> TYPE: PRT
<213> ORGANISM: Homo sapiens

<400> SEQUENCE: 41

Asn His Ser Gly Ser
1               5

<210> SEQ ID NO 42
<211> LENGTH: 16
<212> TYPE: PRT
<213> ORGANISM: Homo sapiens

<400> SEQUENCE: 42

Glu Ile Asn His Ser Gly Ser Thr Asn Tyr Asn Pro Ser Leu Arg Ser
1               5                   10                  15

<210> SEQ ID NO 43
<211> LENGTH: 16
<212> TYPE: PRT
<213> ORGANISM: Homo sapiens

<400> SEQUENCE: 43

Gly Phe Met Val Arg Gly Ile Met Trp Asn Tyr Tyr Tyr Met Asp Val
1               5                   10                  15

<210> SEQ ID NO 44
<211> LENGTH: 16
<212> TYPE: PRT
<213> ORGANISM: Homo sapiens

<400> SEQUENCE: 44
```

Gly Phe Met Val Arg Gly Ile Met Trp Asn Tyr Tyr Met Asp Val
1               5                   10                  15

<210> SEQ ID NO 45
<211> LENGTH: 7
<212> TYPE: PRT
<213> ORGANISM: Mus musculus

<400> SEQUENCE: 45

Gly Tyr Lys Phe Thr Asp Tyr
1               5

<210> SEQ ID NO 46
<211> LENGTH: 5
<212> TYPE: PRT
<213> ORGANISM: Mus musculus

<400> SEQUENCE: 46

Asp Tyr Ser Ile His
1               5

<210> SEQ ID NO 47
<211> LENGTH: 6
<212> TYPE: PRT
<213> ORGANISM: Mus musculus

<400> SEQUENCE: 47

Asp Thr Glu Thr Gly Glu
1               5

<210> SEQ ID NO 48
<211> LENGTH: 17
<212> TYPE: PRT
<213> ORGANISM: Mus musculus

<400> SEQUENCE: 48

Trp Ile Asp Thr Glu Thr Gly Glu Ser Thr Tyr Ala Asp Asp Phe Arg
1               5                   10                  15
Gly

<210> SEQ ID NO 49
<211> LENGTH: 7
<212> TYPE: PRT
<213> ORGANISM: Mus musculus

<400> SEQUENCE: 49

Trp Gly Ser Gly Leu Ala Tyr
1               5

<210> SEQ ID NO 50
<211> LENGTH: 7
<212> TYPE: PRT
<213> ORGANISM: Mus musculus

<400> SEQUENCE: 50

Trp Gly Ser Gly Leu Ala Tyr
1               5

<210> SEQ ID NO 51
<211> LENGTH: 16
<212> TYPE: PRT
<213> ORGANISM: Mus musculus

<400> SEQUENCE: 51

```
Lys Ser Ser Gln Ser Leu Leu Asp Ser Asp Gly Lys Thr Tyr Leu Ser
1               5                   10                  15
```

<210> SEQ ID NO 52
<211> LENGTH: 7
<212> TYPE: PRT
<213> ORGANISM: Mus musculus

<400> SEQUENCE: 52

```
Leu Val Ser Lys Leu Asp Ser
1               5
```

<210> SEQ ID NO 53
<211> LENGTH: 8
<212> TYPE: PRT
<213> ORGANISM: Mus musculus

<400> SEQUENCE: 53

```
Trp Gln Gly Thr His Leu Cys Thr
1               5
```

<210> SEQ ID NO 54
<211> LENGTH: 342
<212> TYPE: RNA
<213> ORGANISM: Mus musculus

<400> SEQUENCE: 54

| | | |
|---|---|---|
| caggugcagc ugcagcaguc cggcggcggc cuggugaagc ccggcggcuc ccugaagcug | 60 |
| uccugcgccg ccuccggcuu caccuucucc uccuacggca uguccugggu gcggcagacc | 120 |
| cccgagaagc ggcuggagug gguggccacc uccaucggcg gcggcccuca caccuacgcc | 180 |
| gccuacccccg acuccgugaa gggccgguuc accaucuccc gggacaacgc caagaacaac | 240 |
| cuguaccugc agaugccucc ccugcggucc gaggacaccg cccuguucua cugcgugcgg | 300 |
| cuguacggca ccuccccccug guucgacuac uggggccagg gc | 342 |

<210> SEQ ID NO 55
<211> LENGTH: 342
<212> TYPE: DNA
<213> ORGANISM: Mus musculus

<400> SEQUENCE: 55

| | | |
|---|---|---|
| caggtgcagc tgcagcagtc cggcggcggc ctggtgaagc ccggcggctc cctgaagctg | 60 |
| tcctgcgccg cctccggctt caccttctcc tcctacggca tgtcctgggt gcggcagacc | 120 |
| cccgagaagc ggctggagtg ggtggccacc tccatcggcg gcggctccta cacctacgcc | 180 |
| gcctaccccg actccgtgaa gggccggttc accatctccc gggacaacgc caagaacaac | 240 |
| ctgtacctgc agatgtcctc cctgcggtcc gaggacaccg ccctgttcta ctgcgtgcgg | 300 |
| ctgtacggca cctccccctg gttcgactac tggggccagg gc | 342 |

<210> SEQ ID NO 56
<211> LENGTH: 7
<212> TYPE: PRT
<213> ORGANISM: Mus musculus

<400> SEQUENCE: 56

```
Gly Phe Thr Phe Ser Ser Tyr
1               5
```

<210> SEQ ID NO 57
<211> LENGTH: 5

-continued

<212> TYPE: PRT
<213> ORGANISM: Mus musculus

<400> SEQUENCE: 57

Ser Tyr Gly Met Ser
1               5

<210> SEQ ID NO 58
<211> LENGTH: 8
<212> TYPE: PRT
<213> ORGANISM: Mus musculus

<400> SEQUENCE: 58

Ile Gly Gly Gly Ser Tyr Thr Tyr
1               5

<210> SEQ ID NO 59
<211> LENGTH: 19
<212> TYPE: PRT
<213> ORGANISM: Mus musculus

<400> SEQUENCE: 59

Thr Ser Ile Gly Gly Gly Ser Tyr Thr Tyr Ala Ala Tyr Pro Asp Ser
1               5                   10                  15

Val Lys Gly

<210> SEQ ID NO 60
<211> LENGTH: 10
<212> TYPE: PRT
<213> ORGANISM: Mus musculus

<400> SEQUENCE: 60

Leu Tyr Gly Thr Ser Pro Trp Phe Asp Tyr
1               5                   10

<210> SEQ ID NO 61
<211> LENGTH: 10
<212> TYPE: PRT
<213> ORGANISM: Mus musculus

<400> SEQUENCE: 61

Leu Tyr Gly Thr Ser Pro Trp Phe Asp Tyr
1               5                   10

<210> SEQ ID NO 62
<211> LENGTH: 327
<212> TYPE: RNA
<213> ORGANISM: Mus musculus

<400> SEQUENCE: 62
gacauccaga ugacccaguc ccccgccauc cuguccgugu cccccggcga gcggugucc        60 uucuccugcc gggccuccca guccaucggc accuccaucc acugguacca gcagcggacc      120
aacggcuccc cccggcugcu gaucgccgcc gccuacccg ccuccgaguc cuacgccccc       180
ucccgguucu ccggcucccg guccggcacc gacgccaccc uguccaucaa cuccguggag      240
uccgaggaca ucgccgacua cuacugccag cagucaacu ccuggcccu gaccuucggc        300 gccggcacca agcuggagau caagcgg                                          327

<210> SEQ ID NO 63
<211> LENGTH: 327
<212> TYPE: DNA
<213> ORGANISM: Mus musculus

```
<400> SEQUENCE: 63
gacatccaga tgacccagtc ccccgccatc ctgtccgtgt ccccggcga gcgggtgtcc         60 ttctcctgcc gggcctccca gtccatcggc acctccatcc actggtacca gcagcggacc       120
aacggctccc cccggctgct gatcgccgcc gcctactccg cctccgagtc ctacgccccc       180
tcccggttct ccggctcccg gtccggcacc gacgccaccc tgtccatcaa ctccgtggag       240
tccgaggaca tcgccgacta ctactgccag cagtccaact cctggcccct gaccttcggc       300
gccggcacca agctggagat caagcgg                                           327

<210> SEQ ID NO 64
<211> LENGTH: 11
<212> TYPE: PRT
<213> ORGANISM: Mus musculus

<400> SEQUENCE: 64

Arg Ala Ser Gln Ser Ile Gly Thr Ser Ile His
1               5                   10

<210> SEQ ID NO 65
<211> LENGTH: 8
<212> TYPE: PRT
<213> ORGANISM: Mus musculus

<400> SEQUENCE: 65

Ala Ala Tyr Ser Ala Ser Glu Ser
1               5

<210> SEQ ID NO 66
<211> LENGTH: 9
<212> TYPE: PRT
<213> ORGANISM: Mus musculus

<400> SEQUENCE: 66

Gln Gln Ser Asn Ser Trp Pro Leu Thr
1               5
```